United States Patent
Haswani et al.

(10) Patent No.: US 9,827,204 B2
(45) Date of Patent: *Nov. 28, 2017

(54) IMMEDIATE RELEASE ABUSE-DETERRENT GRANULATED DOSAGE FORMS

(71) Applicant: CIMA LABS INC., Brooklyn Park, MN (US)

(72) Inventors: Dinesh K. Haswani, Plymouth, MN (US); Derek V. Moe, Mound, MN (US); Victoria A. O'Neill, Wayzata, MN (US); Randal A. Seburg, Maple Grove, MN (US); Manuel A. Vega Zepeda, Minnetonka, MN (US)

(73) Assignee: Cima Labs Inc., Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/210,760

(22) Filed: Jul. 14, 2016

(65) Prior Publication Data

US 2016/0317457 A1 Nov. 3, 2016

Related U.S. Application Data

(63) Continuation of application No. PCT/US2015/064403, filed on Dec. 8, 2015.

(60) Provisional application No. 62/088,901, filed on Dec. 8, 2014.

(51) Int. Cl.
| | |
|---|---|
| *A61K 9/50* | (2006.01) |
| *A61K 9/28* | (2006.01) |
| *A61K 31/00* | (2006.01) |
| *A61K 9/20* | (2006.01) |
| *A61K 31/136* | (2006.01) |
| *A61K 31/165* | (2006.01) |
| *A61K 31/137* | (2006.01) |
| *A61K 31/437* | (2006.01) |
| *A61K 31/485* | (2006.01) |
| *A61K 31/515* | (2006.01) |
| *A61K 31/5513* | (2006.01) |
| *A61K 47/48* | (2006.01) |
| *A61K 31/167* | (2006.01) |
| *A61K 31/554* | (2006.01) |

(52) U.S. Cl.
CPC .......... *A61K 9/5078* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2886* (2013.01); *A61K 9/5073* (2013.01); *A61K 31/00* (2013.01); *A61K 31/136* (2013.01); *A61K 31/137* (2013.01); *A61K 31/165* (2013.01); *A61K 31/167* (2013.01); *A61K 31/437* (2013.01); *A61K 31/485* (2013.01); *A61K 31/515* (2013.01); *A61K 31/554* (2013.01); *A61K 31/5513* (2013.01); *A61K 47/4823* (2013.01); *A61K 47/48046* (2013.01); *A61K 47/48176* (2013.01)

(58) Field of Classification Search
CPC .. A61K 31/485; A61K 31/135; A61K 31/137; A61K 31/165; A61K 31/437; A61K 31/4458; A61K 31/515; A61K 31/5513; A61K 31/554; A61K 9/2081; A61K 9/5026; A61K 9/5078; A61K 2300/00; A61K 31/167; A61K 31/192; A61K 9/2054

See application file for complete search history.

(56) References Cited

U.S. PATENT DOCUMENTS

| | | | |
|---|---|---|---|
| 7,375,083 B2 | 5/2008 | Mickle et al. | |
| 7,658,939 B2 | 2/2010 | Oshlack et al. | |
| 7,682,633 B2 | 3/2010 | Matthews et al. | |
| 2003/0068375 A1* | 4/2003 | Wright | A61K 9/2013 424/468 |
| 2012/0231716 A1 | 9/2012 | Janssen et al. | |
| 2013/0034503 A1 | 2/2013 | Howard et al. | |
| 2015/0118303 A1* | 4/2015 | Haswani | A61K 31/4402 424/465 |

FOREIGN PATENT DOCUMENTS

| | | |
|---|---|---|
| WO | WO 2005/056619 | 6/2005 |
| WO | WO2008024490 A2 | 2/2008 |
| WO | WO 2013/077851 | 5/2013 |
| WO | WO 2013128276 A2 * | 9/2013 ............. A61K 45/06 |
| WO | WO2013128276 A2 | 9/2013 |
| WO | WO2015066172 A1 | 5/2015 |
| WO | WO2015120201 A1 | 8/2015 |

* cited by examiner

*Primary Examiner* — Mark V Stevens
(74) *Attorney, Agent, or Firm* — Baker Hostetler LLP

(57) ABSTRACT

Described are immediate release oral dosage forms that contain abuse-deterrent features. In particular, the disclosed dosage forms provide deterrence of abuse by ingestion of multiple individual doses. In addition, the disclosed dosage forms provide protection from overdose in the event of accidental or intentional ingestion of multiple individual doses.

33 Claims, 37 Drawing Sheets

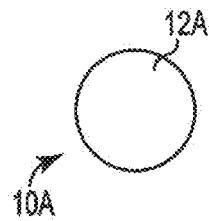
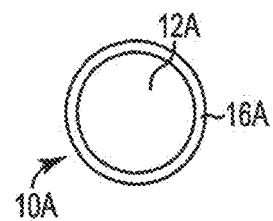
Fig. 1A
Fig. 1B
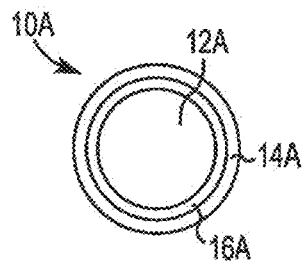
Fig. 1C
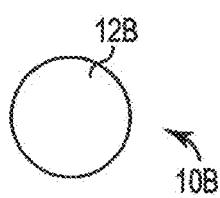
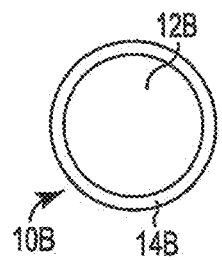
Fig. 2A
Fig. 2B
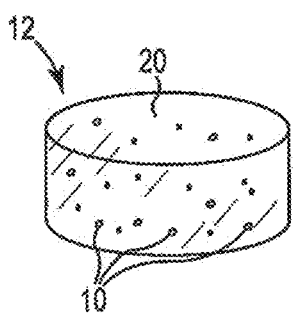
Fig. 3

PK of the test and reference Hydrocodone / APAP products after administration of 6 tablets

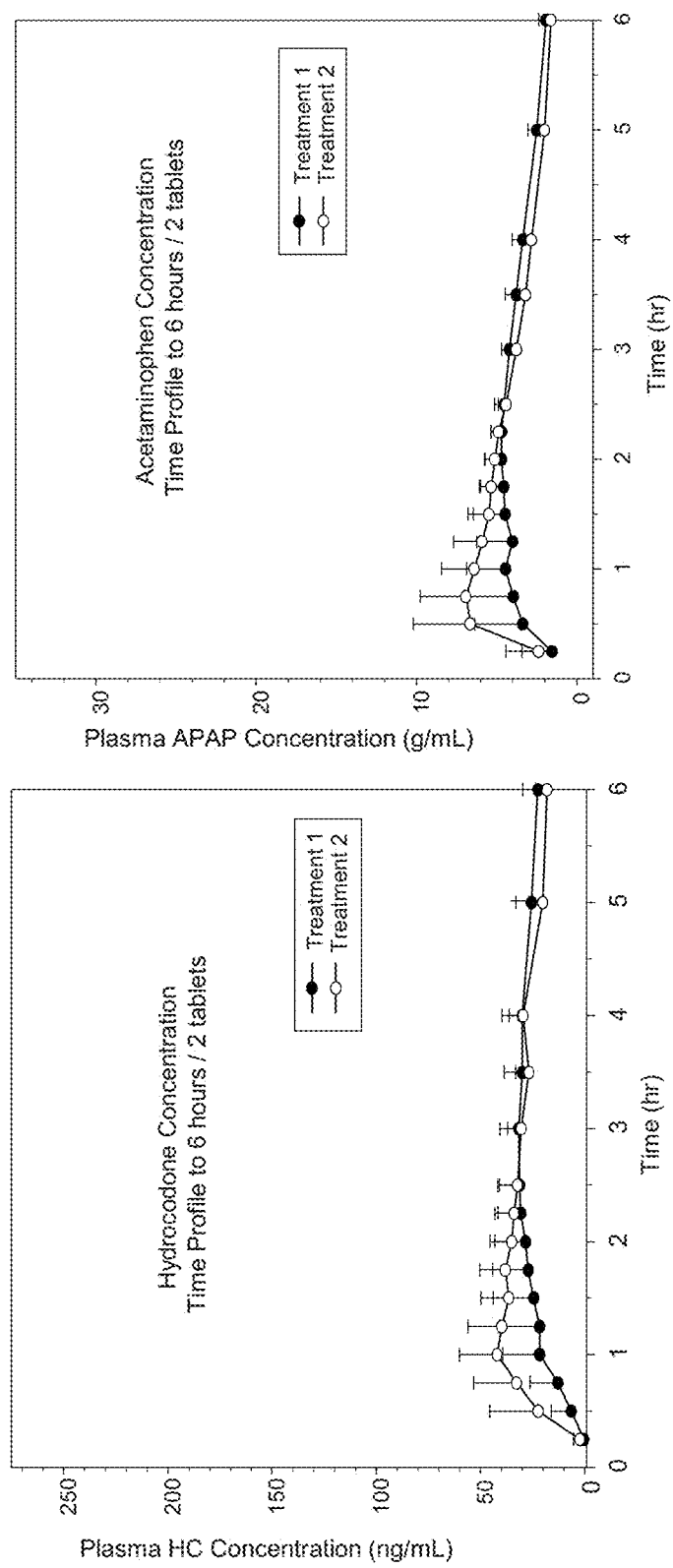

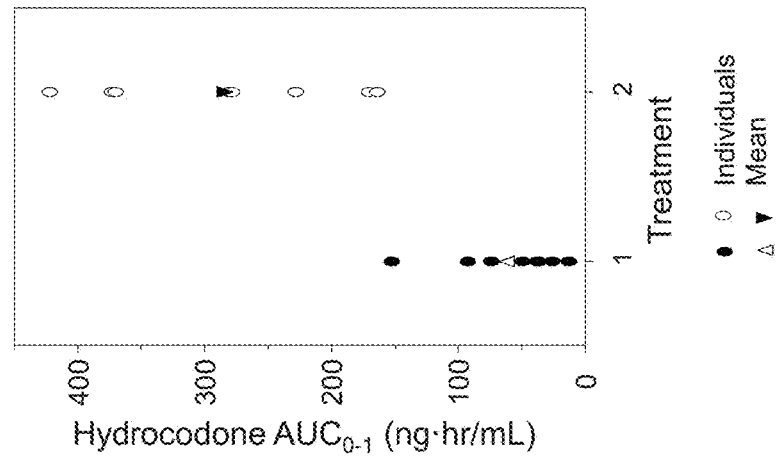
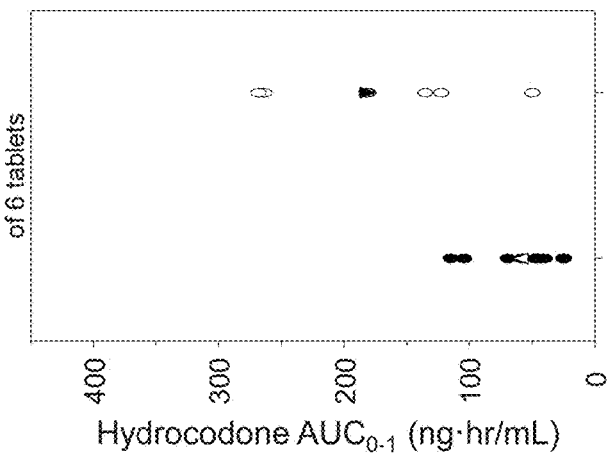
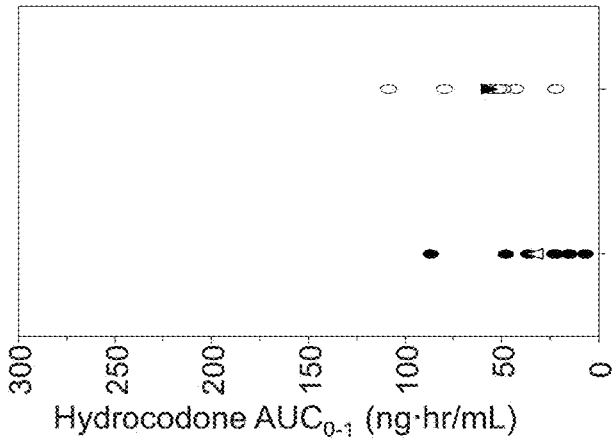

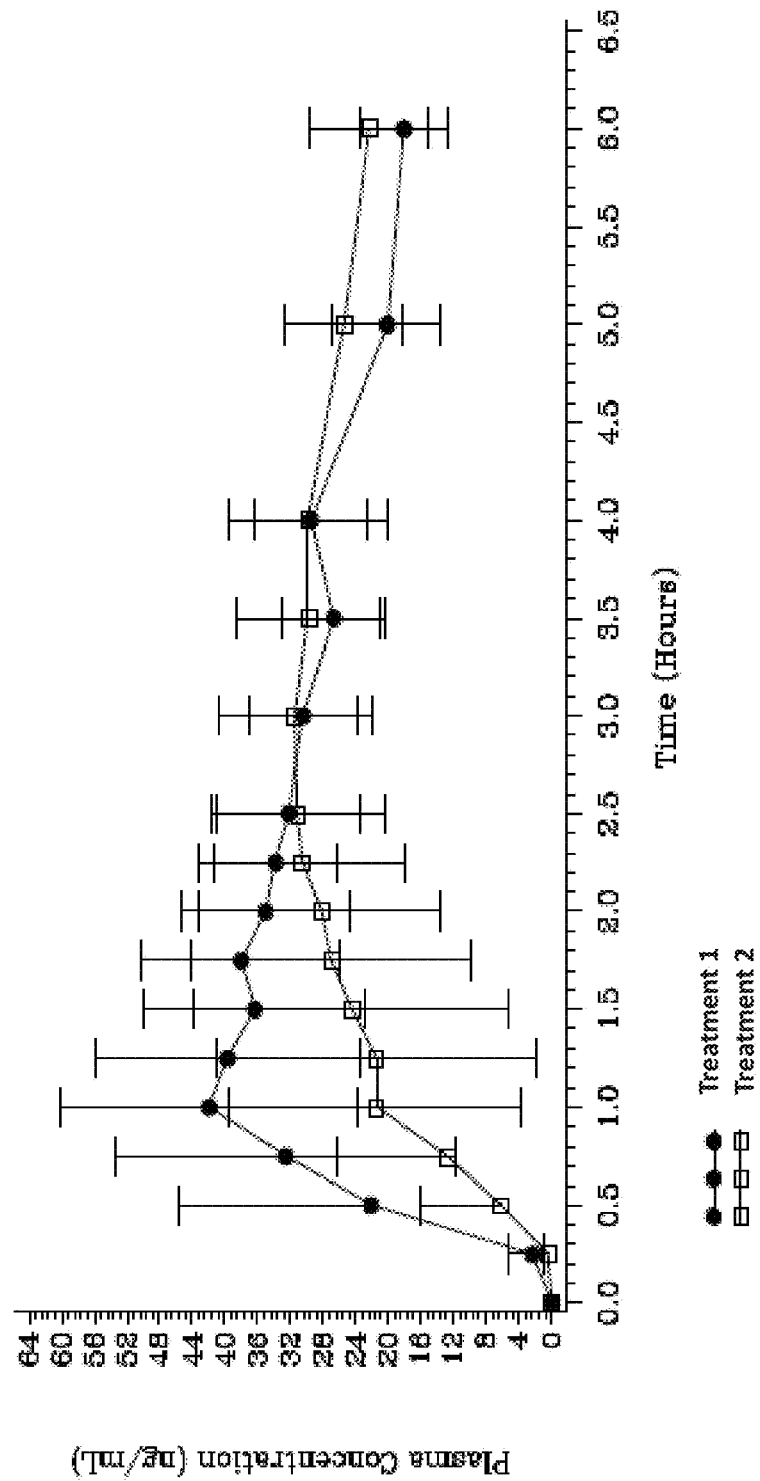

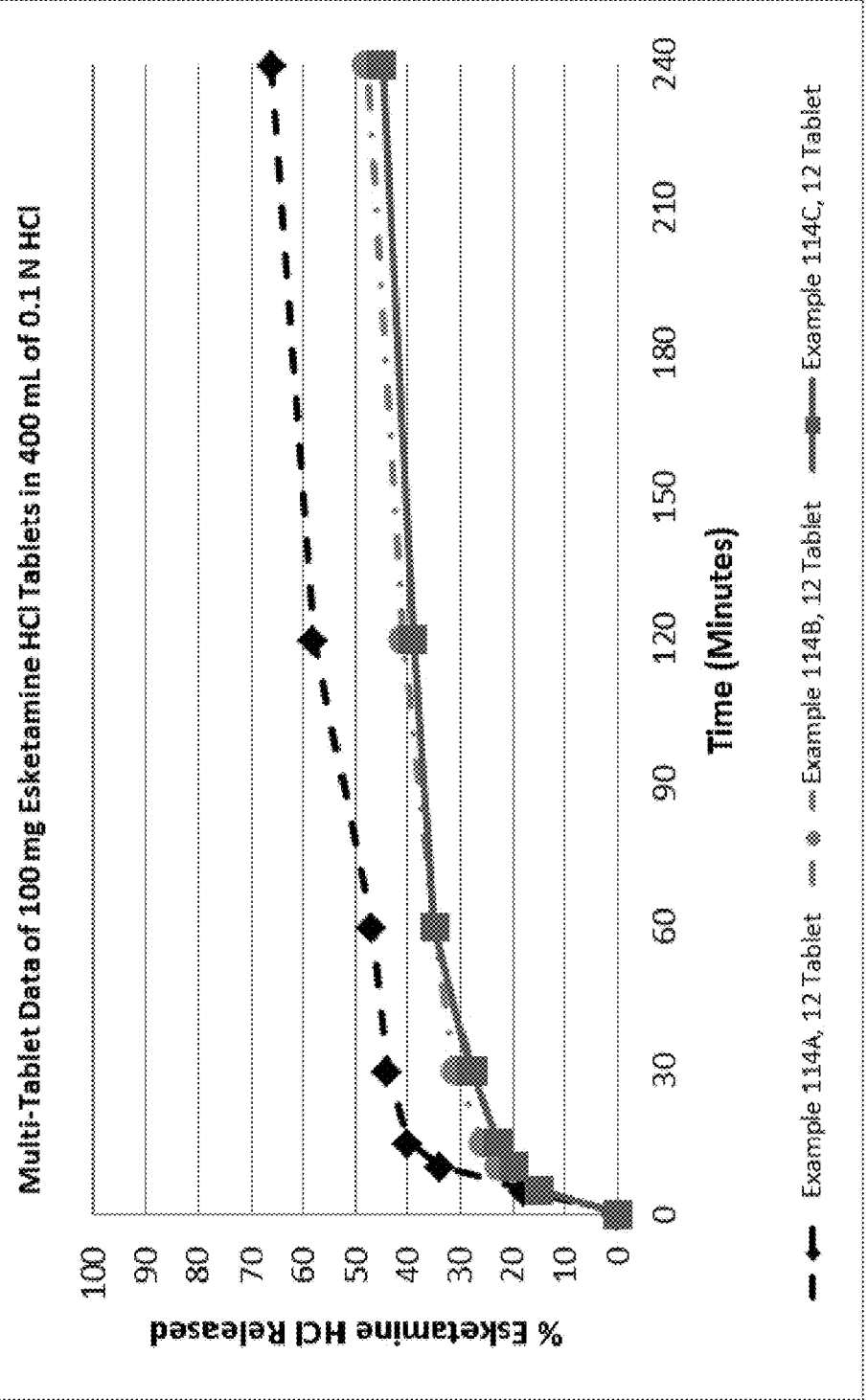

IMMEDIATE RELEASE ABUSE-DETERRENT GRANULATED DOSAGE FORMS

CROSS REFERENCE TO RELATED APPLICATIONS

This application is a continuation of PCT/US2015/064403, filed on Dec. 8, 2015, which claims the benefit of U.S. Provisional Application No. 62/088,901, filed Dec. 8, 2014, the entire contents of both of which are incorporated herein by reference.

FIELD OF THE INVENTION

The present invention relates to the field of oral dosage forms that contain abuse-deterrent features, in particular including immediate release dosage forms that contain a drug that is commonly susceptible to abuse.

BACKGROUND

Pharmaceutical products, including both prescription and over-the-counter pharmaceutical products, while useful for improving health of a person in need, are also susceptible to intentional and unintentional abuse and overdosing. Examples of commonly abused active pharmaceutical ingredients include psychoactive drugs, anxiolytics, sedative hypnotics, stimulants, depressants, and analgesics such as narcotic analgesics, among others. A complete list of specific drug compounds that are commonly abused would be lengthy; a short listing of some classes of drugs commonly abused includes opioids and morphine derivatives, barbiturates, amphetamines, ketamine, and other drugs that can cause psychological or physical dependence.

Some common techniques for intentionally abusing a drug begin with an abuser obtaining a solid dosage form such as an orally administered tablet or capsule, and crushing the solid dosage form into a powder. The powder may be administered by an abuser by nasal insufflation (i.e., "snorting") to introduce the drug to the abuser's bloodstream intranasally. Alternately, the crushed dosage form may be combined with a solvent that is capable of dissolving the drug (active pharmaceutical ingredient, or "API"), and the solvent with the dissolved drug may be injected directly into an abuser's bloodstream.

Alternatively, with immediate release oral dosage forms, an abuser might simply ingest multiple units (e.g., tablets) of the dosage form together, e.g., simultaneously. Each one of the multiple dosage form units—immediately releases an amount of drug to produce a short-term concentration spike of the drug in the user's bloodstream and a desired "high" in the user.

The pharmaceutical industry has identified various mechanisms of adapting drug compositions and oral dosage forms that can be useful to discourage abuse of oral dosage forms. Pharmaceutical companies have studied dosage forms that contain a nasal irritant or an effervescent agent, which can cause irritation or pain in a nasal passage if the dosage form is crushed and then snorted, thus discouraging abuse by nasal insufflation. Pharmaceutical companies studied adding gelling polymers to dosage forms to prevent abuse by injection. If the dosage form is crushed to a powder and combined with a small amount of solvent, the gelling polymer can cause the combination to take the form of a highly viscous liquid or gel that cannot be administered by injection. Another possible abuse deterrent may be addition of an emetic agent which can deter abuse by causing emesis on ingestion of multiple doses. Another abuse deterrent involves adding an antagonist of an API to a dosage form that will substantially block the effect of the drug.

Although the pharmaceutical industry has identified of a variety of abuse deterrent (sometimes referred to as "abuse-resistant") features useful with oral dosage forms, there is continuing need to improve and identify new abuse deterrent features to inhibit or prevent abuse or overdosing of active pharmaceutical ingredients.

SUMMARY

The following description relates to oral dosage forms that are useful for immediate release of an active pharmaceutical ingredient or "API."

The dosage form can be designed to release the API as desired in an immediate release dosage form, and can also include one or a combination of feature that will prevent or deter abuse of the API. The abuse deterrent features described herein can be included singly or in any combination in an immediate release dosage form.

As a first type of abuse deterrent feature, a dosage form as described can include a gelling polymer to prevent or compromise abuse practices wherein the dosage form is crushed and then combined with a small amount of a solvent to produce a liquid composition that contains a concentrated amount of API and that can be delivered to an abuser using a syringe. The gelling polymer can be any polymer useful to achieve this functionality, and can be placed in the dosage form at any location to allow the gelling polymer to perform as described and still allow immediate release of the API. A gelling polymer can be included in a core of a coated of core-shell particle or in a matrix of a dosage form that suspends the core-shell particles. The core may contain any amount of gelling polymer, such as from 0 to 100 percent gelling polymer based on a total weight of the core. Alternately, the core in a core-shell particle may comprise a filler, e.g., up to 100 percent filler, such as a sugar sphere or microcrystalline cellulose sphere (up to 100 percent microcrystalline cellulose spheres such as those available under the trade name Celphere®).

Another type of abuse deterrent feature can be a wax that alone or with other ingredients, e.g., the gelling polymer, is effective in compromising abuse practices wherein a dosage form is crushed and combined with a solvent to produce a liquid composition that can be abused by nasal insufflation or delivered to an abuser using a syringe. The wax can additionally inhibit or prevent an abuser from grinding the dosage form into a powder because upon grinding the wax will smear as opposed to fracturing or powdering. Similar to the gelling polymer, wax can be included in a dosage form at any location that allows the wax to function as an abuse deterrent feature while not interfering with an immediate release profile of the API. For example, a wax can be included in a core of a coated particle. A core may contain any amount of wax, such as from 0 to 100 percent wax based on a total weight of the core, such as up to 50, 75, or 80 weight percent wax based on a total weight of the core.

Still another type of abuse deterrent feature can be a filler or binder that alone or in combination with other ingredients can compromise abuse practices wherein a dosage form is being crushed and combined with a small amount of a solvent to produce a liquid composition that can be delivered to an abuser using a syringe. The filler or binder can inhibit or prevent an abuser from grinding the dosage form into a powder because upon grinding, the polymeric filler or binder will smear as opposed to fracturing or powdering. The filler or binder can be included in a dosage form in any manner and location that allows the filler or binder to function as an abuse deterrent feature while not interfering with an immediate release profile of the API. For example, a filler or binder can be included in a core of a coated particle. A core may contain any amount of polymeric filler or binder such as from 0 to 100 percent filler or binder on a total weight of the core, or up to 50, 75, or 80 weight percent filler or binder based on a total weight of the core.

Yet another type of abuse deterrent feature can be a film layer that surrounds or covers API in a dosage form and that is optionally resistant to being dissolved by one or more of the solvents commonly used by abusers to dissolve an API for injection, including water and $C_1$-$C_4$ alcohols such as ethanol, methanol, and mixtures thereof. The film layer may be prepared from any film material that is disposed as a continuous layer on a coated particle at a location to enclose and surround the API. Examples of film layers can optionally and preferably provide properties of a solvent-resistant film, which is a film that is slow or difficult to dissolve in a limited or small volume of one the solvents commonly used by abusers to dissolve API of a dosage form. To access an API of a dosage form an abuser may grind the dosage form and combine the ground dosage form with a solvent (as described) in an attempt to produce a solution that contains the concentrated API and the solvent, and that may be efficiently injected or snorted. By being slow to dissolve or insoluble in one or more of water, or a $C_1$-$C_4$ alcohol such as ethanol, methanol, etc., a solvent-resistant film layer that surrounds API of a dosage form can prevent an abuser from easily accessing and so manipulating the API.

In exemplary embodiments, an immediate release dosage form can include these features in a coated particle, such as a core-shell particle. An exemplary core-shell particle can include a core and one or more layers surrounding the core. For such a core-shell particle, the API may be included in the core, or in one or more layers surrounding the core, or in both the core and one or more layers surrounding the core. The dosage form may additionally contain core-shell particles that do not include the API in either the core, or in any layer surrounding the core. The core can include any one or more of: a gelling polymer, wax, binder, or filler, alone or in combination. Alternately, the core may comprise a microcrystalline cellulose or sugar sphere.

A film layer may surround and enclose the core, or an API-containing layer that is disposed around the core. The film layer may preferably be a solvent-resistant film in the form of a continuous coating that covers the core, which contains API, or that covers an API-containing layer or coating disposed around the core, or that covers a core that has no API-containing layer or coating disposed around the core and contains no API.

According to other various embodiments, a coated particle as described herein can be useful in a dosage form that includes one or more optional abuse deterrent features, and a matrix such as a compressed matrix that is formed to allow for immediate release of the API present in the coated particles. An exemplary matrix composition may comprise additional gelling polymer, disintegrant, or both additional gelling polymer and disintegrant. The expression "additional gelling polymer" as used above means an amount of gelling polymer that is in addition to an amount of gelling polymer present in the coated particles. The additional gelling polymer may be the same or different in nature, chemistry, molecular weight, etc., as compared to the gelling polymer that is included in the coated particles. A disintegrant as a component of the matrix may be useful to facilitate release of the API of the dosage form, e.g., API present in the coated particles.

The active pharmaceutical ingredient included in the dosage form, especially in the coated particle surrounded by a film layer (e.g., a solvent resistant film), can be any active pharmaceutical ingredient desired to be administered orally, and may in particular be a type of active pharmaceutical ingredient that is commonly susceptible to abuse. Examples of active pharmaceutical ingredients that are considered to be commonly susceptible to abuse include psychoactive drugs, tranquilizers, sedative hypnotics, anxiolytics, stimulants, depressants, and narcotic analgesics, among others. Certain more specific classes of drugs commonly abused includes opioids, barbiturates, benzodiazepines, amphetamines, as well as many other drugs that are known to cause psychological or physical dependence.

Dosage forms of the present description can be useful as immediate release dosage forms, and may also include abuse deterrent features as described. The abuse deterrent features can discourage or prevent abuse by nasal insufflation, by injection, and can also be effective to prevent or significantly limit the success of abuse by the common methods (especially with immediate release oral dosage forms) of orally taking multiple dosage form units together. The final mode of abuse (sometimes referred to herein as "multi-tablet dosing") is often particularly difficult to deter, especially in immediate release oral dosage forms, making these described dosage forms particularly useful as abuse-deterrent oral immediate release dosage forms.

Embodiments of the described dosage forms can be effective in the absence of other types of abuse deterrent features such as nasal irritants, emetic agents, buttering agents, and effervescent agents, to inhibit nasal insufflation or other forms of abuse, or the inclusion of drug antagonists of the subject drug.

In one aspect, the invention relates to an immediate release dosage form that includes core-shell particles. The core-shell particles include: an inner core containing a gelling polymer; at least one layer surrounding the core, the at least one layer including a film layer surrounding the core; and an active pharmaceutical ingredient. The active pharmaceutical ingredient is also surrounded by the film layer that surrounds the core.

In another aspect, the invention relates to an immediate release dosage form that includes core-shell particles. The core-shell particles include a core and an active pharmaceutical layer surrounding the core. The active pharmaceutical layer contains an active pharmaceutical ingredient. The core contains less than 5 weight percent of a total amount of the active pharmaceutical ingredient in the core-shell particles.

In yet another aspect the invention relates to an immediate release dosage form that contains core-shell particles. The core-shell particles include: a core and an active pharmaceutical ingredient. The dosage form further includes a matrix. The matrix includes disintegrant and an additional amount of gelling polymer.

In still another aspect, the invention relates to an immediate release dosage form that includes two types of core-shell particles. One type of core-shell particles includes a core and an active pharmaceutical layer surrounding the core as discussed above. The core of these particles optionally contains less than 5 weight percent of the total amount of the API in that core-shell particle, and in some instances contains less than 1 weight percent of the total amount of the API in that core-shell particle, or even contains no significant amount of the API. The other type of core shell particles comprise the core, but do not contain an active pharmaceutical layer surrounding the core.

BRIEF DESCRIPTION OF THE DRAWINGS

FIGS. 1A, 1B, and 1C illustrate embodiments of core-shell particles as described, in cross section.

FIGS. 2A and 2B illustrate embodiments of core-shell particles as described, in cross section.

FIG. 3 is a perspective view of an embodiment of a dosage form as described.

FIGS. 21a and 21b show two plots comparing pharmacokinetics of the test hydrocodone/acetaminophen formulation to a marketed/conventional hydrocodone/acetaminophen (FIG. 21a showing plasma levels of hydrocodone, and FIG. 21b showing plasma levels of acetaminophen), as a function of time following simultaneous administration to healthy naltrexone-blocked human male subjects of two hydrocodone bitartrate/acetaminophen tablets (10 mg/tablet hydrocodone bitartrate and 325 mg acetaminophen).

FIGS. 25a, 25b, and 25c show plots comparing the area under curve (AUC) of hydrocodone for of the test hydrocodone/acetaminophen formulation (Treatment 1) to a marketed/conventional hydrocodone/acetaminophen (Treatment 2) indicating hydrocodone exposure after 2 hours post-dose for simultaneous administration of 2 tablets (FIG. 25a), 6 tablets (FIG. 25b) and 10 tablets (FIG. 25c).

FIG. 26 shows a plot comparing pharmacokinetics of the test hydrocodone/acetaminophen formulation (Treatment 2) to a marketed/conventional hydrocodone/acetaminophen (Treatment 1), showing mean (±SD) plasma concentration-time profiles of hydrocodone over 6 hours following administration to healthy naltrexone-blocked human male subjects of 2 tablets of hydrocodone bitartrate/acetaminophen (10 mg/tablet hydrocodone bitartrate and 325 mg/tablet acetaminophen).

FIG. 39 shows plots of multiple tablet dissolution (12 tablets) of Esketamine HCl tablets prepared according to Examples 114A, 114B and 114C (100 mg/tablet Esketamine HCl) in 0.1 N HCl as a function of time.

DETAILED DESCRIPTION

Figure 4:
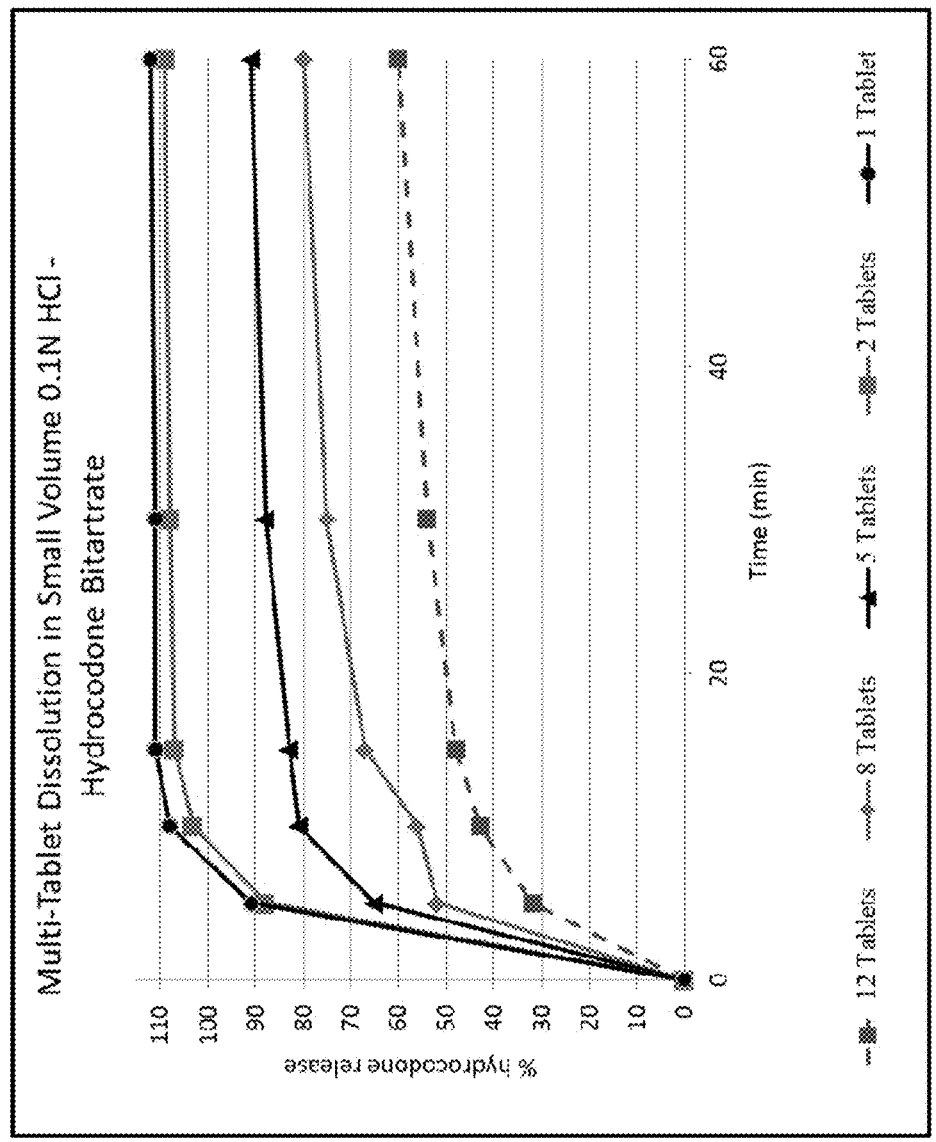
FIG. 4 shows a plot of multiple tablet oral abuse resistance (supratherapeutic dosing)—dissolution of hydrocodone bitartrate in 0.1N HCl media as a function of time.
Figure 5:
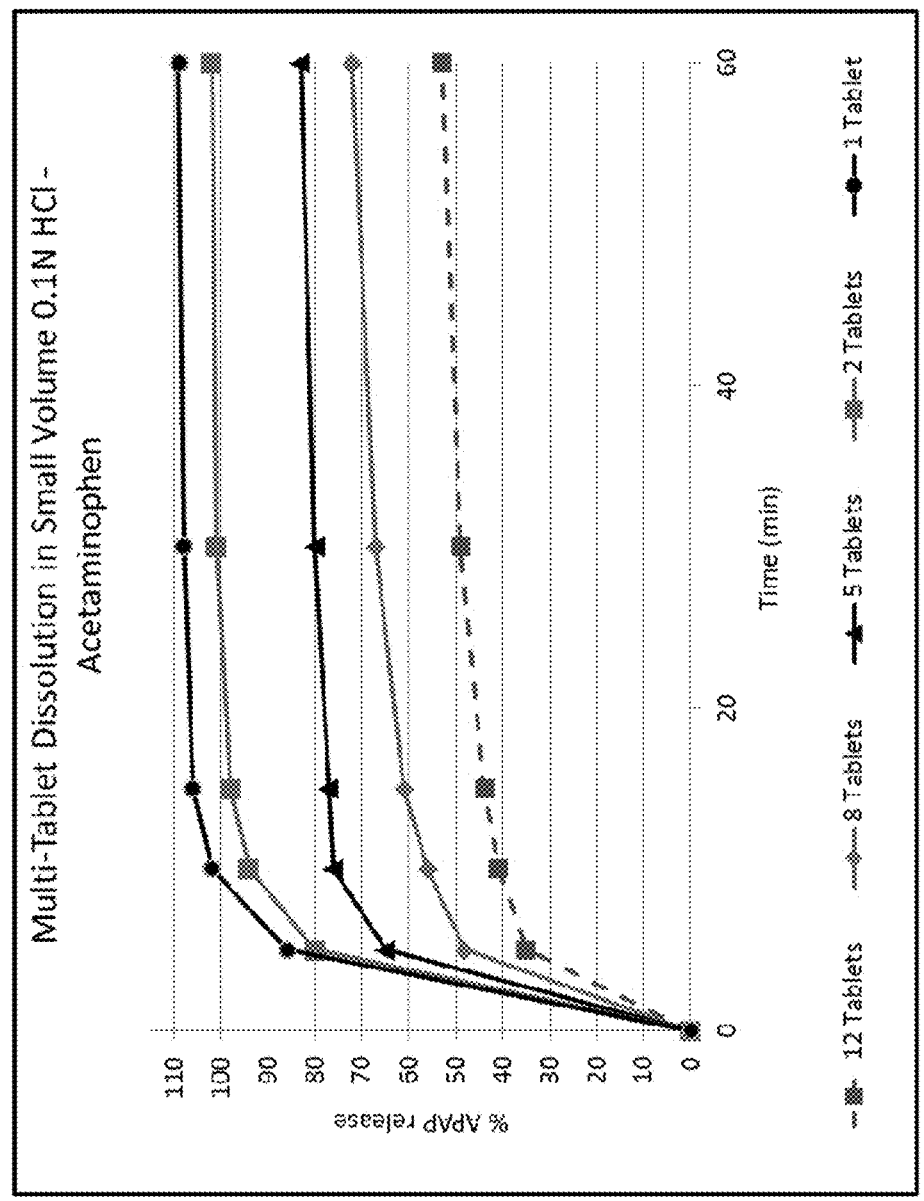
FIG. 5 shows a plot of multiple tablet oral abuse resistance (supratherapeutic dosing)—dissolution of acetaminophen in 0.1N HCl media as a function of time.
Figure 6:
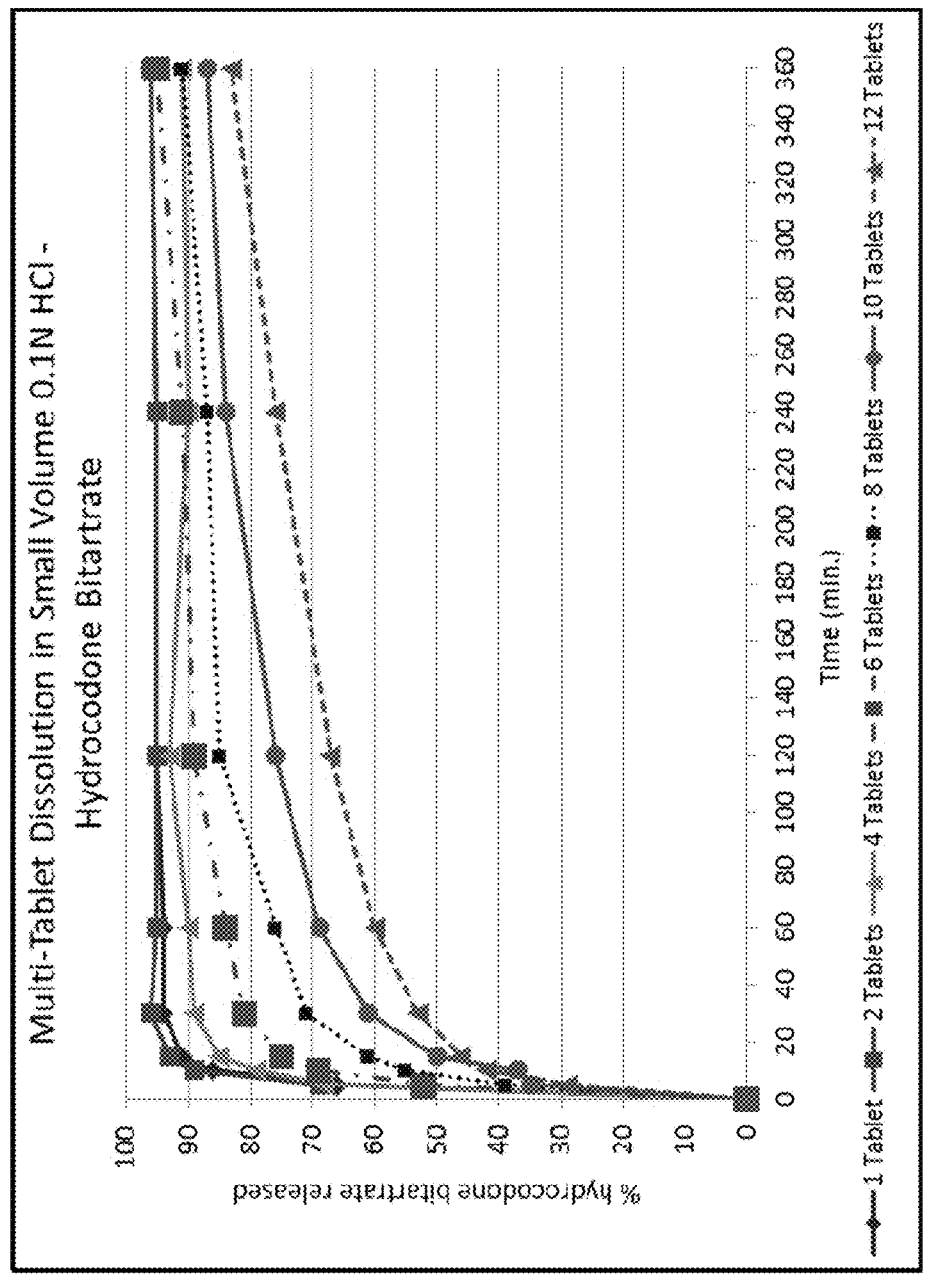
FIG. 6 shows a plot of multiple tablet oral abuse resistance (supratherapeutic dosing)—dissolution of hydrocodone bitartrate in 0.1N HCl media as a function of time.
Figure 7:
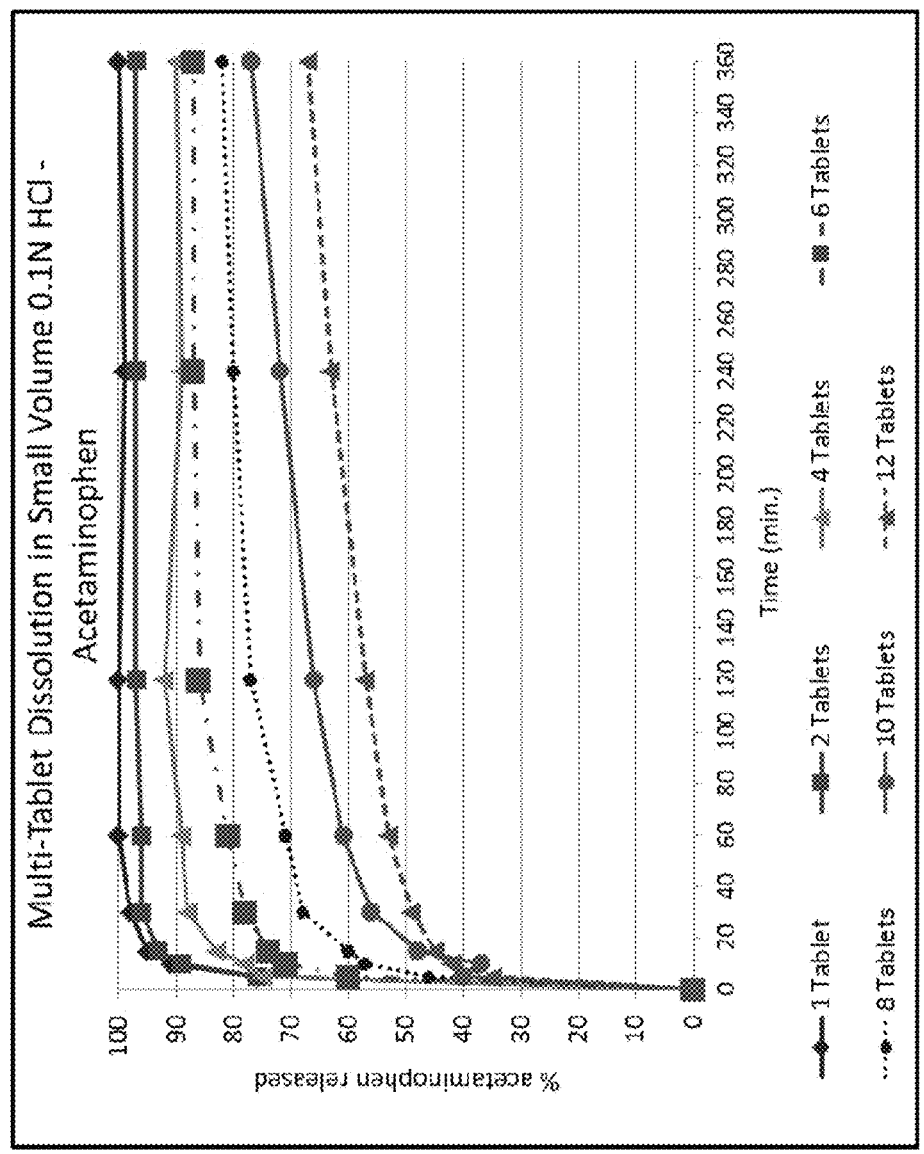
FIG. 7 shows a plot of multiple tablet oral abuse resistance (supratherapeutic dosing)—dissolution of acetaminophen in 0.1N HCl media as a function of time.
Figure 8:
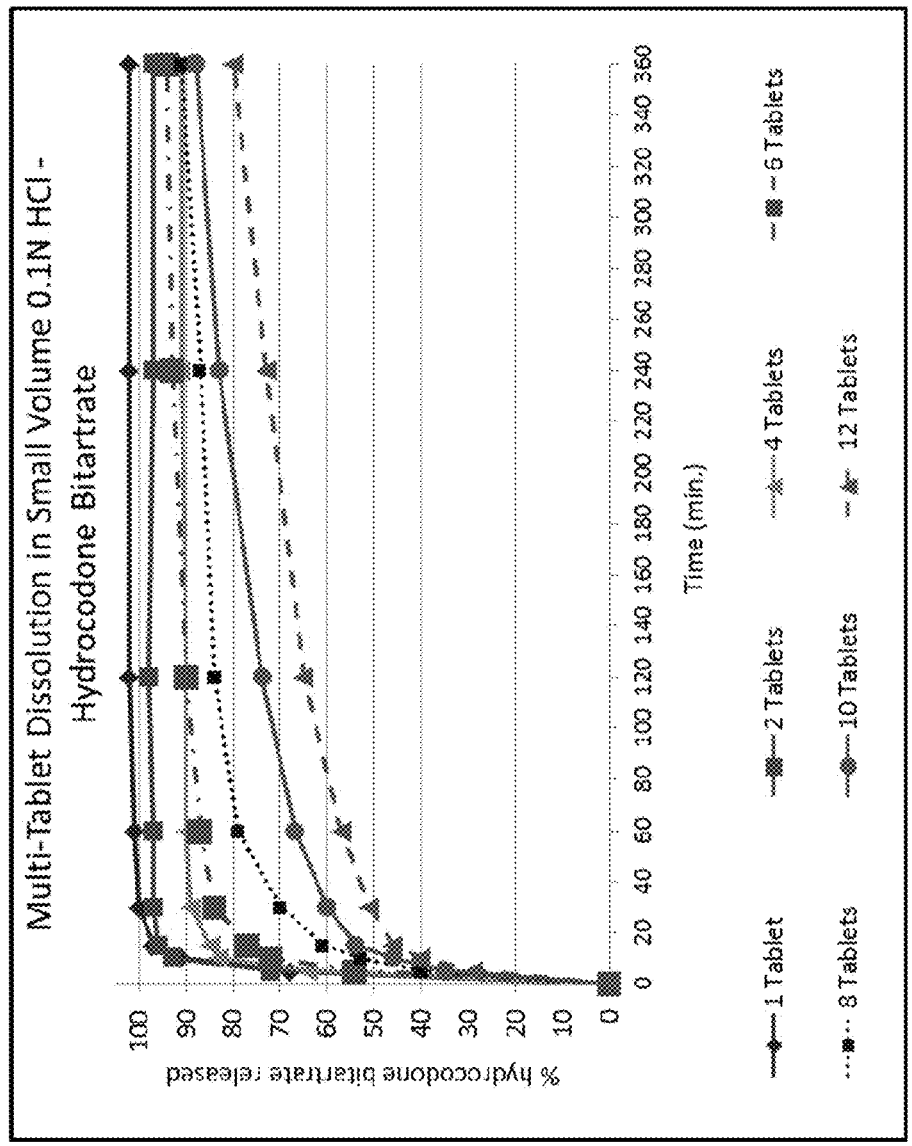
FIG. 8 shows a plot of multiple tablet oral abuse resistance (supratherapeutic dosing)—dissolution of hydrocodone bitartrate in 0.1N HCl media as a function of time.
Figure 9:
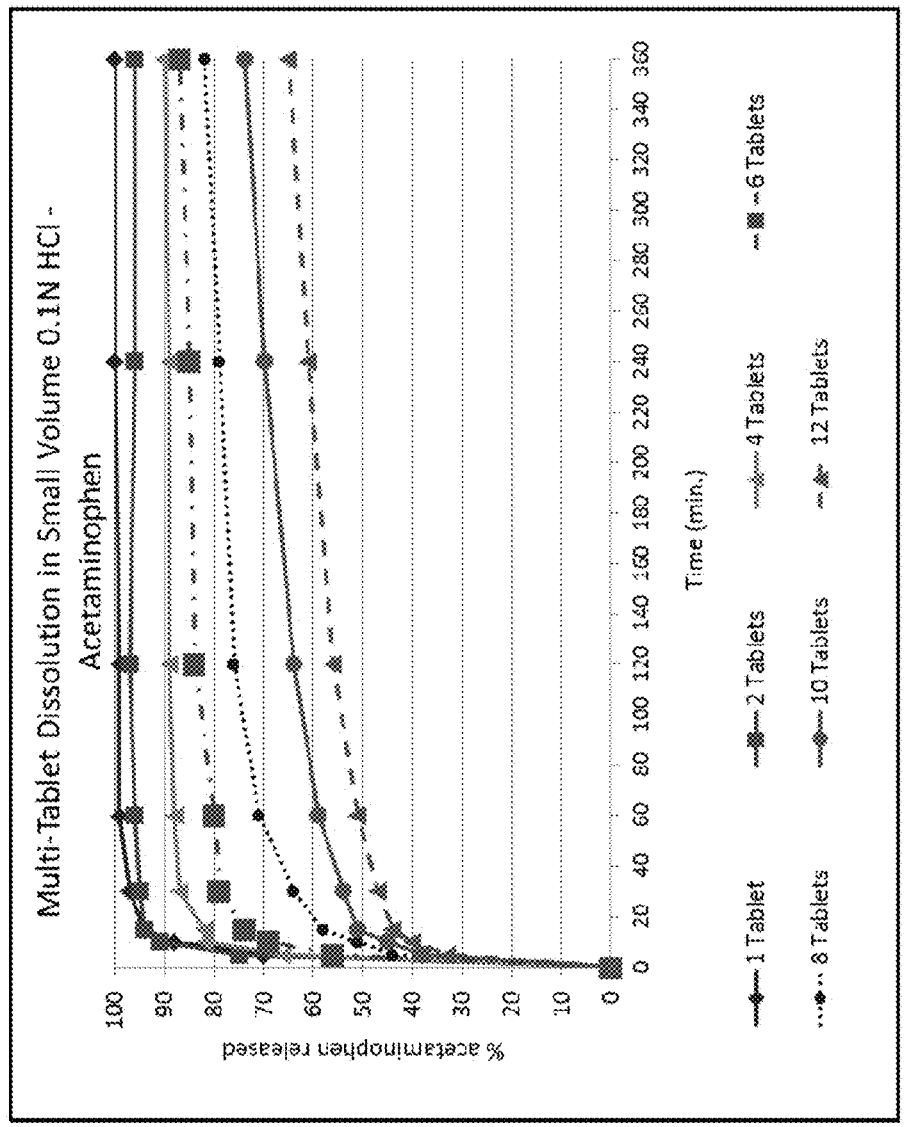
FIG. 9 shows a plot of multiple tablet oral abuse resistance (supratherapeutic dosing)—dissolution of acetaminophen in 0.1N HCl media as a function of time.

The present description relates to immediate release dosage forms that include one or more abuse deterrent features for reducing the potential for a) parenteral abuse, b) abuse by nasal insufflation ("snorting"), and c) abuse by simultaneous oral ingestion of multiple oral dosage form units (tablets or capsules) of a drug. These abuse deterrent features are achieved by preparing the dosage form to include certain structural features and certain ingredients that have now been determined to effectively prevent an abuser from realizing the intended biological effect of the drug abuse by using certain presently-common methods used to abuse the API. Advantageously, a dosage form prepared to contain one or more of the described abuse deterrent features, as a deterrent to abuse of one or more API that is commonly susceptible to abuse, can still be constructed to provide immediate release of the one or more API upon normal therapeutic use by oral ingestion.

As used herein, expressions such as "abuse deterrent" and "preventing" or "deterring" or "inhibiting" practices and processes associated with the abuse and overdose of drugs, relate to features of the claimed formulations that provide significant physical and chemical impediments to these practices and processes. The objective in such deterrence includes both making abuse practices significantly more difficult to carry out, and making any product resulting from an attempt to carry out such abuse practices on the claimed formulations significantly less desirable, less profitable, and less abusable to the potential abuser.

The term "immediate release" refers to a dosage form that upon oral ingestion by a human releases substantially all of a contained active pharmaceutical ingredient into a gastrointestinal tract for biological uptake in a short time. In vitro methods of measuring a release profile of a dosage form, for the purpose of determining whether a dosage form exhibits an immediate release or extended release dissolution profile, are known in the pharmaceutical arts. By such methods, examples of immediate release dosage forms as described herein can be measured to be capable of releasing substantially all of a total amount of at least one type of active pharmaceutical ingredient (e.g., an API commonly susceptible to abuse) contained in the dosage form (e.g., at least 75, 80, or 90 weight percent of the total amount of the API in a dosage form) into a solution (e.g., acidic aqueous solution) of a suitable pH within 240 minutes, e.g., in less than 180 minutes, less than 90 minutes, or less than 60, 30, 15, or 5 minutes. For example, a release profile of a dosage form of the present description may be measured by a method that exposes the dosage form to a volume of up to 900 milliliters (e.g., 300 milliliters, or 900 milliliters, based on various test methods) of hydrochloric acid (0.01 to 0.1N) (e.g., aqueous hydrochloric acid) at a pH of from 1 to 2, and at a temperature of 37 degrees Celsius. According to some embodiments, the dosage forms described herein, demonstrate not less than 90% of API released in 60 minutes when administered at therapeutic doses, wherein the release profiles may be evaluated, for example, by dissolution in 300 mL of 0.1N HCl media using USP II apparatus at 50 RPM paddle speed and 37° C. A release profile of a dosage form of the present description may alternatively be measured by a method that exposes the dosage form to a volume of up to 900 milliliters (e.g., 300 milliliters, 400 milliliters, or 900 milliliters, based on various test methods) of an aqueous buffer solution (e.g., an acetate buffer solution) at a pH that is representative of the pH conditions of a fed stomach, e.g., at a pH of about 4.5, and at a temperature of 37 degrees Celsius.

The term "extended release" can be defined as not more than 95% release of the API at 60 minutes, wherein the release profiles may be evaluated, for example, by dissolution in 300 mL of 0.1N HCl media using USP II apparatus at 50 RPM paddle speed and 37° C. According to some embodiments, the dosage forms described herein, demonstrate:

not less than 90% of API released in 60 minutes when administered at therapeutic doses; and
not more than 95% release of the API at 60 minutes when administered at supratherapeutic doses;

wherein the release profiles may be evaluated by dissolution in 300 mL of 0.1N HCl media using USP II apparatus at 50 RPM paddle speed and 37° C. In this context, a "supratherapeutic dose" will be understood to correspond to administration of five or more, six or more, seven or more, eight or more, nine or more, ten or more, eleven or more, or twelve or more individual dose units, e.g., tablets, simultaneously. It will also be understood that administering multiple individual dose units simultaneously would reasonably include administering those multiple doses sequentially over a short time interval, e.g., over an interval of less than 60 minutes, less than 30 minutes, less than 15 minutes, less than 5 minutes or less than one minute.

Dosage forms as described can be formulated to provide an immediate release profile of an API, and can also be prepared to include effective or advantageous abuse deterrent features that are effective to deter abuse of the same API (e.g., one that is commonly susceptible to abuse) that exhibits the immediate release profile. The combination of immediate release of an API with broad abuse resistance of the same API for multiple abuse modalities including multi-tablet dosing, as described herein, is not believed to be previously known. More particularly, dosage forms as described herein can provide an immediate release profile of an API, and can at the same time include abuse deterrent features that provide general abuse deterrence or abuse resistance of the same API. The dosage forms can also be more specifically characterized as resistant to certain common methods of abuse, such as 1) abuse by injection (e.g., by steps that include grinding a dosage form and dissolving API of the dosage form), 2) abuse by nasal insufflation (e.g., also by grinding and optionally dissolving API of a dosage form), and 3) abuse by multi-tablet dosing by oral consumption, meaning simultaneous oral ingestion of multiple or excessive quantities of orally administered dosage forms such as tablets or capsules. The third mode of abuse, multi-tablet dosing, is particularly common with immediate release dosage forms and is particularly difficult to defend against by design of a dosage form structure or by formulation. Accordingly, that the presently-described dosage forms can be effective to prevent or deter abuse (or even accidental overdose) by the mode of multi-tablet dosing can be a particularly useful feature of the dosage forms described herein.

In vitro testing of exemplary dosage forms as described herein indicates that exemplary dosage forms provide deterrence against abuse by multi-tablet dosing. More specifically, in vitro testing of exemplary dosage forms was performed by conducting dissolution testing of one or more dosage forms (tablets) in 300 milliliters (or 400 milliliters according to some testing methods) of 0.1N HCL maintained at 37 degrees Celsius using a 50 RPM paddle speed. See, Example 26 (a) and FIGS. 4 and 5 herein. As shown at FIGS. 4, 5, 6, 7, 8 and 9, the amount (percentage per tablet) of API (opioid) or APAP (acetaminophen) released in the media is reduced with an increase in the number of tablets. The data also suggest that the tested dosage forms are effective to prevent increased levels of API uptake in an individual who would accidentally ingest multiple tablets, preventing or reducing the risk of an unintentional overdose of the API. (In FIGS. 4 and 5, the 1 tablet and 2 tablet dosage forms are as prepared in Example 3, infra, and the 5 tablet, 8 tablet, and 12 tablet dosage forms are as prepared in Example 5, infra. The tablets used in FIGS. 6, 7, 8 and 9 are as prepared as per Example 17.)

Figure 14:
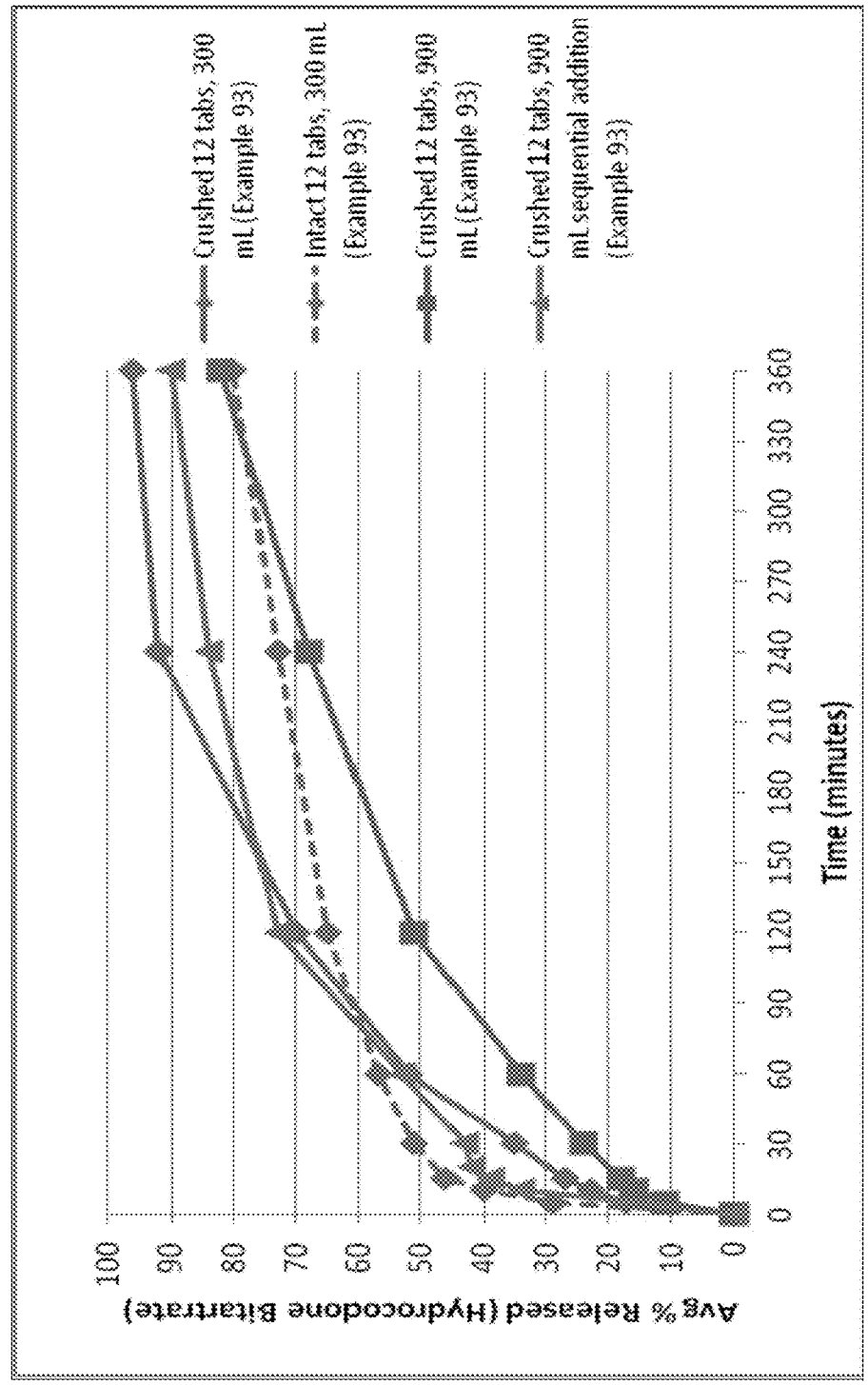
FIG. 14 shows a plot of multiple tablet oral abuse resistance (supratherapeutic dosing)—dissolution of hydrocodone bitartrate from hydrocodone bitartrate/acetaminophen tablets (10/325 mg/tablet of hydrocodone bitartrate/acetaminophen, tested both as intact tablets and crushed tablets) in 0.1N HCl media as a function of time.
Figure 15:
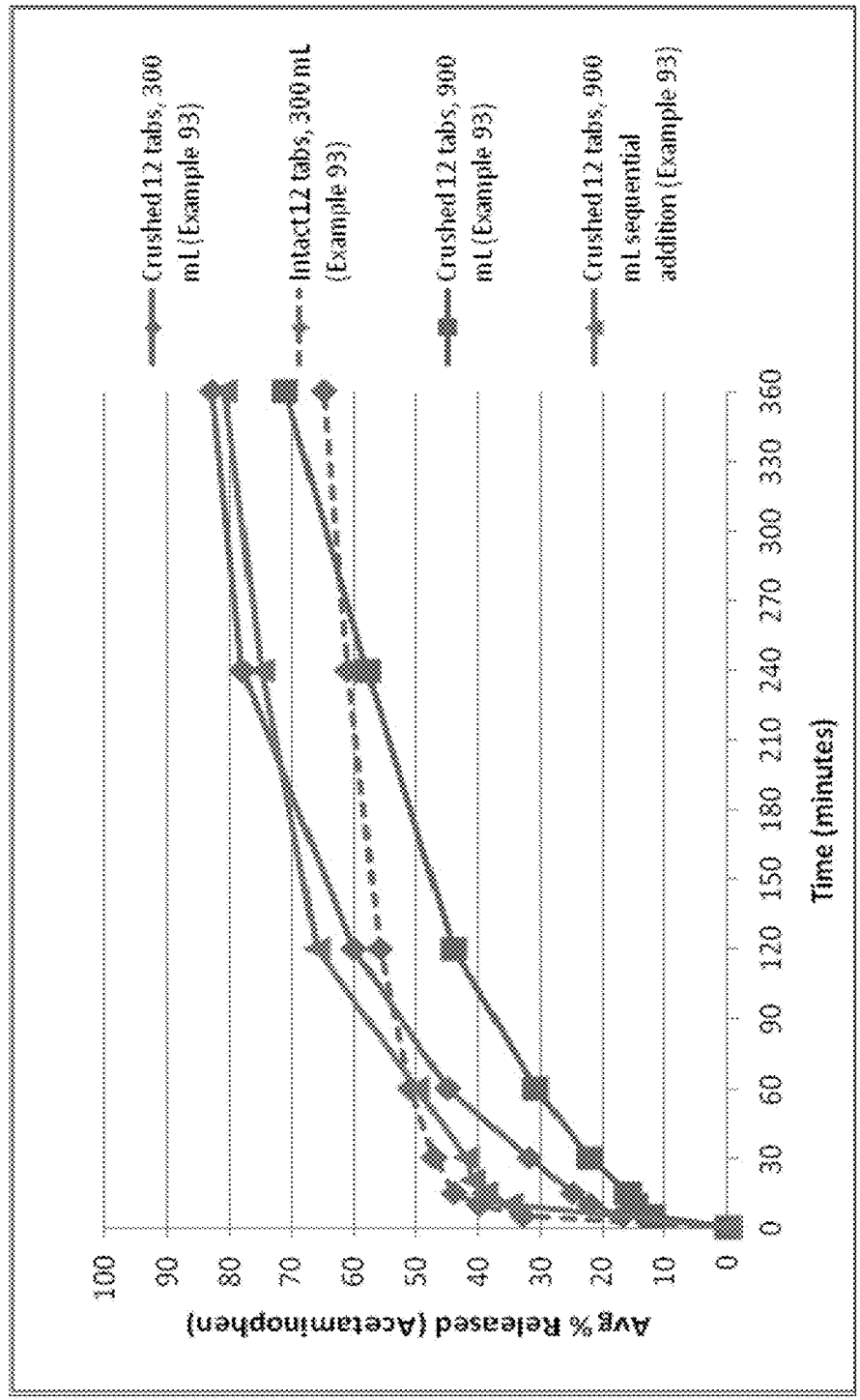
FIG. 15 shows a plot of multiple tablet oral abuse resistance (supratherapeutic dosing)—dissolution of acetaminophen from hydrocodone bitartrate/acetaminophen tablets (10/325 mg/tablet of hydrocodone bitartrate/acetaminophen, tested both as intact tablets and crushed tablets) in 0.1N HCl media as a function of time.
Figure 16:
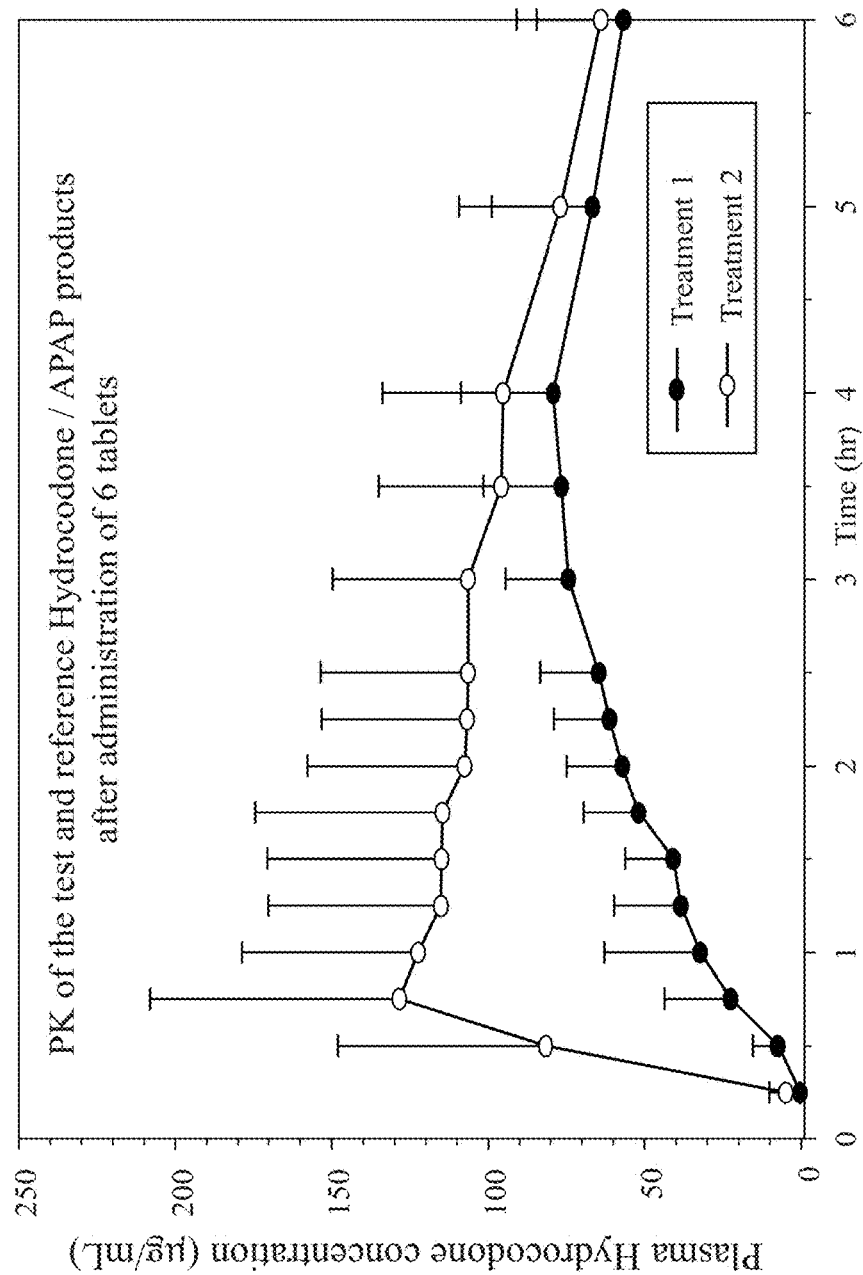
FIG. 16 shows a plot of plasma levels of hydrocodone as a function of time following simultaneous administration to healthy naltrexone-blocked human male subjects of six hydrocodone bitartrate/acetaminophen tablets (10 mg/tablet hydrocodone bitartrate and 325 mg acetaminophen).
Figure 17:
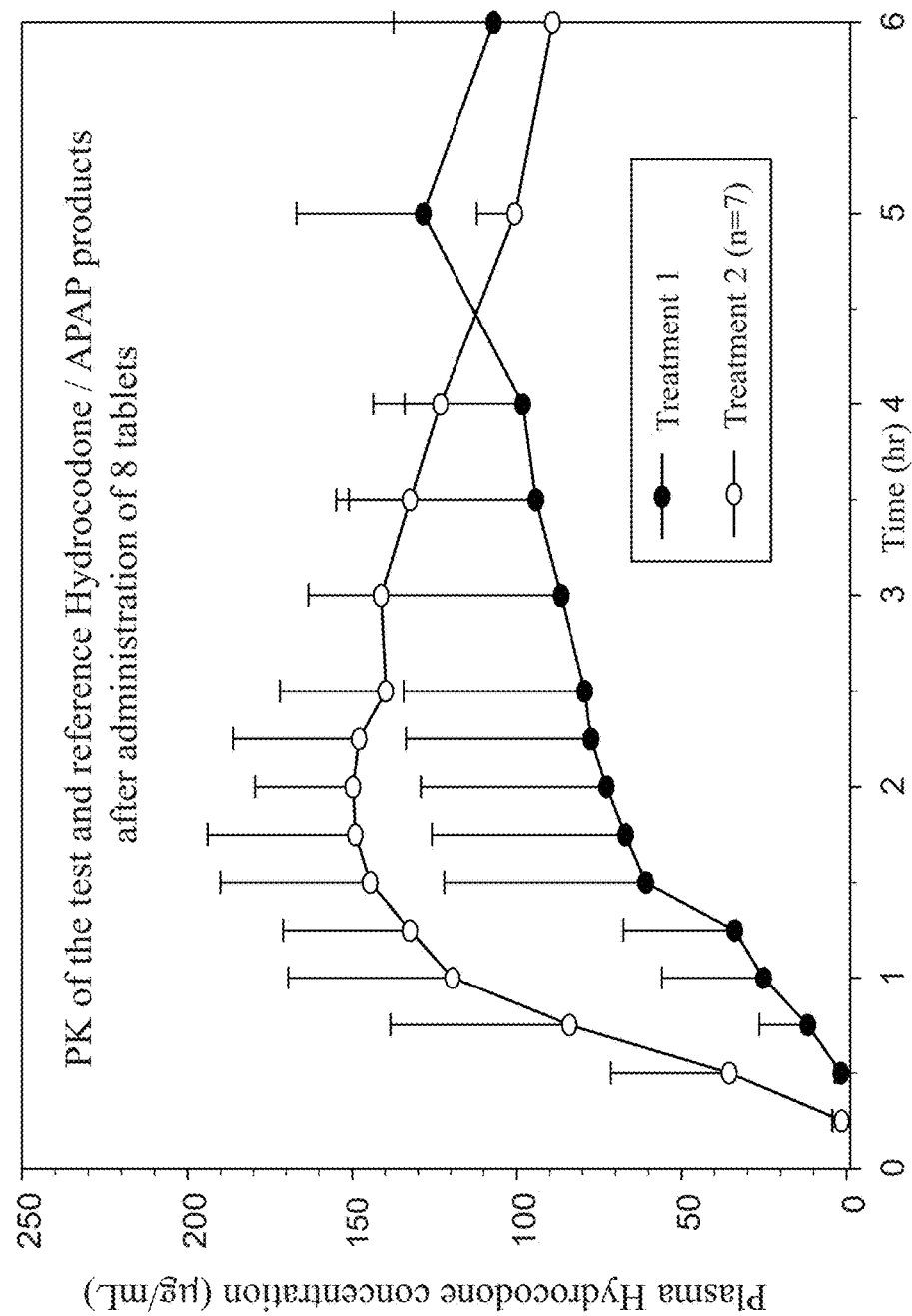
FIG. 17 shows a plot of plasma levels of hydrocodone as a function of time following simultaneous administration to healthy naltrexone-blocked human male subjects of eight hydrocodone bitartrate/acetaminophen tablets (10 mg/tablet hydrocodone bitartrate and 325 mg acetaminophen).
Figure 18:
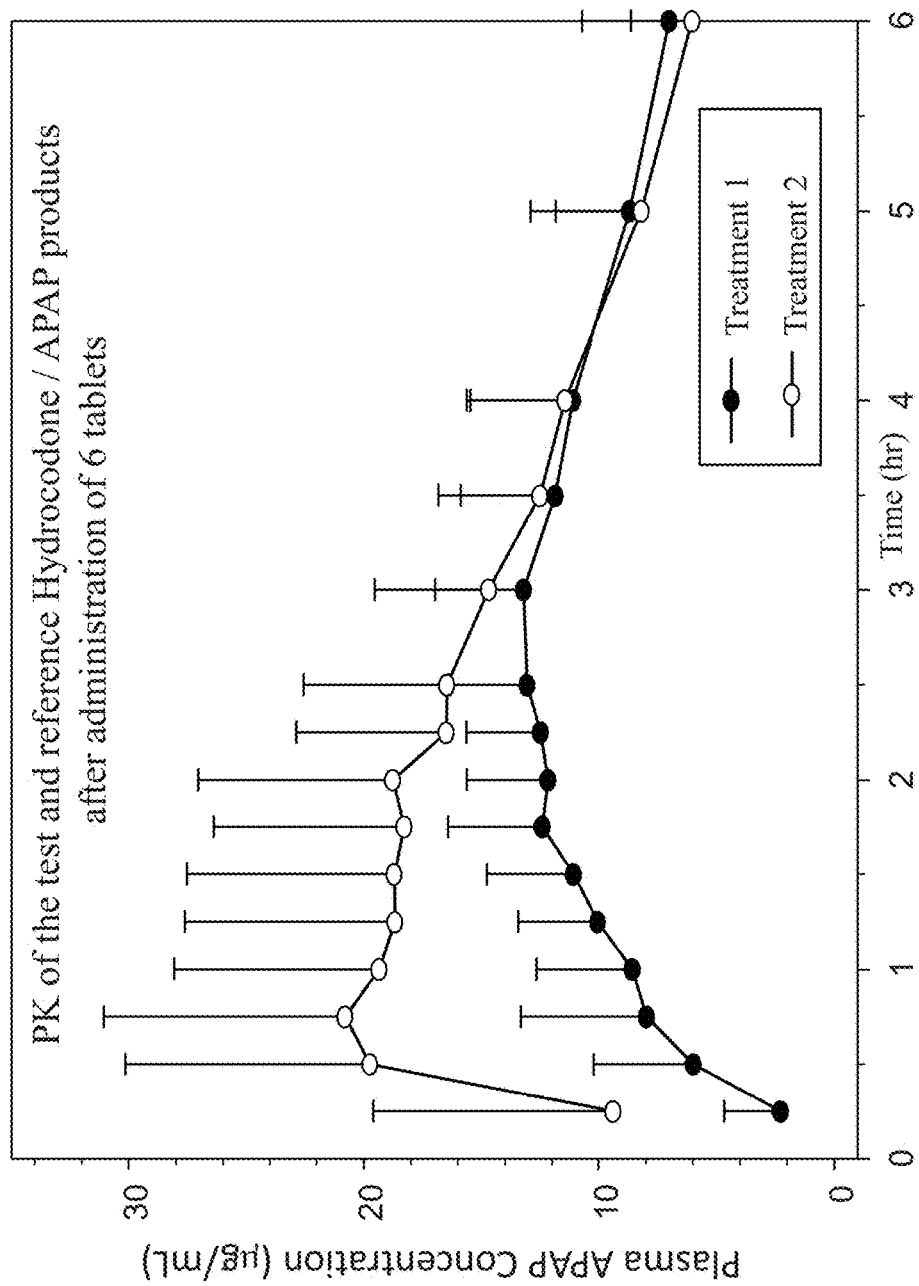
FIG. 18 shows a plot of plasma levels of acetaminophen as a function of time following simultaneous administration to healthy naltrexone-blocked human male subjects of six hydrocodone bitartrate/acetaminophen tablets (10 mg/tablet hydrocodone bitartrate and 325 mg acetaminophen).
Figure 19:
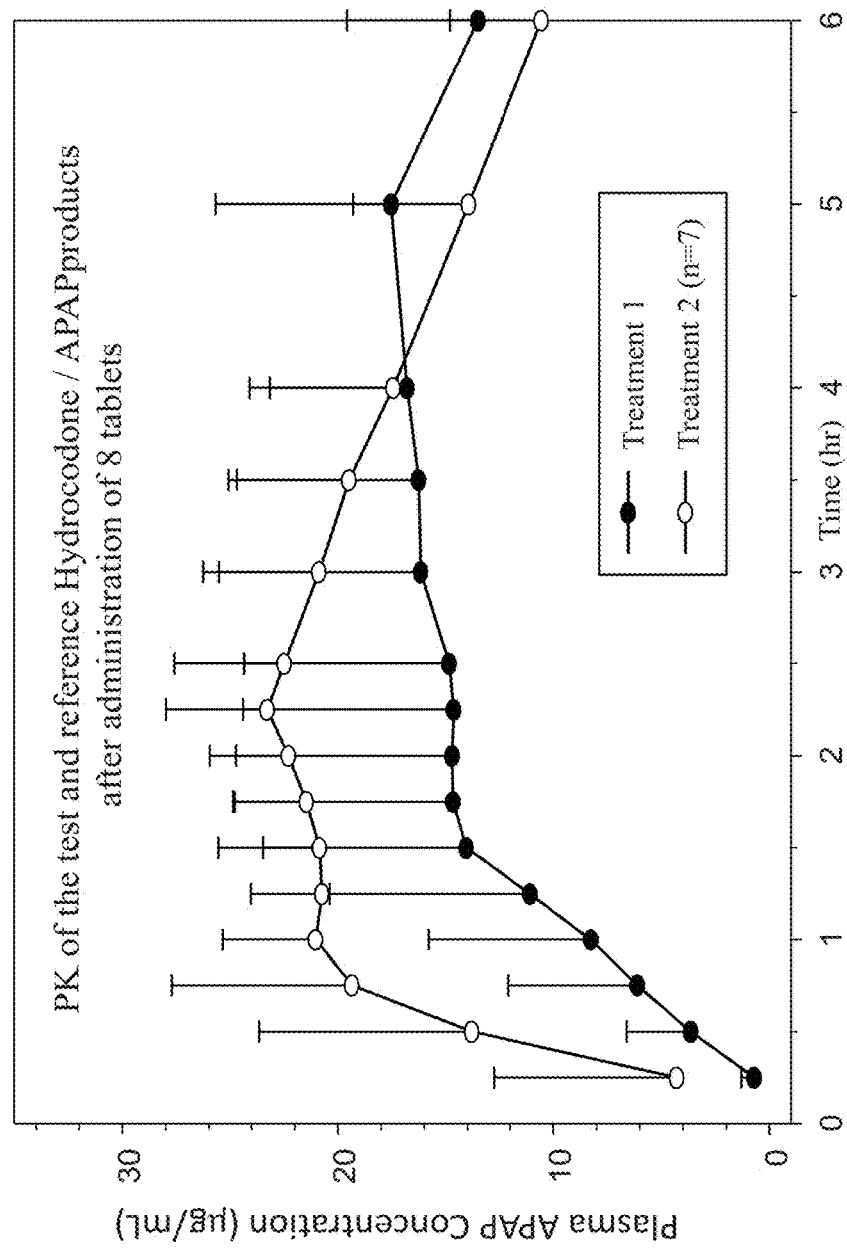
FIG. 19 shows a plot of plasma levels of acetaminophen as a function of time following simultaneous administration to healthy naltrexone-blocked human male subjects of eight hydrocodone bitartrate/acetaminophen tablets (10 mg/tablet hydrocodone bitartrate and 325 mg acetaminophen).
Figure 20B:
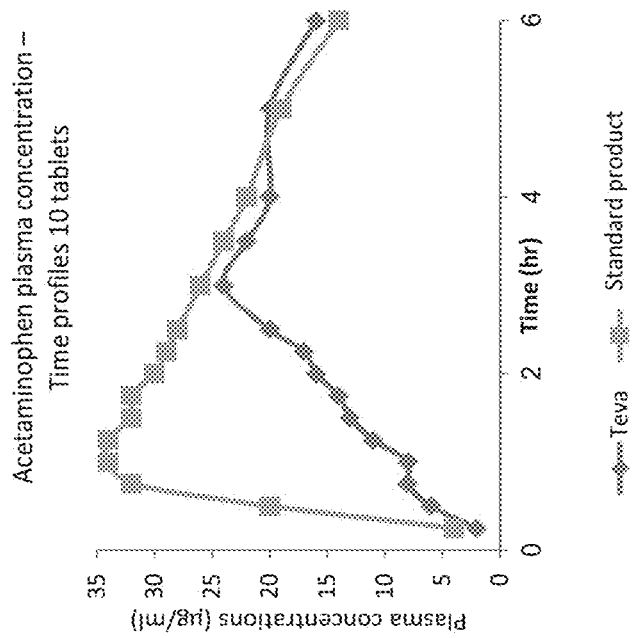
FIGS. 20a and 20b show two plots comparing pharmacokinetics of the test hydrocodone/acetaminophen formulation to a marketed/conventional hydrocodone/acetaminophen (FIG. 20a showing plasma levels of hydrocodone, and FIG. 20b showing plasma levels of acetaminophen), as a function of time following simultaneous administration to healthy naltrexone-blocked human male subjects of ten hydrocodone bitartrate/acetaminophen tablets (10 mg/tablet hydrocodone bitartrate and 325 mg acetaminophen).
Figure 20A:
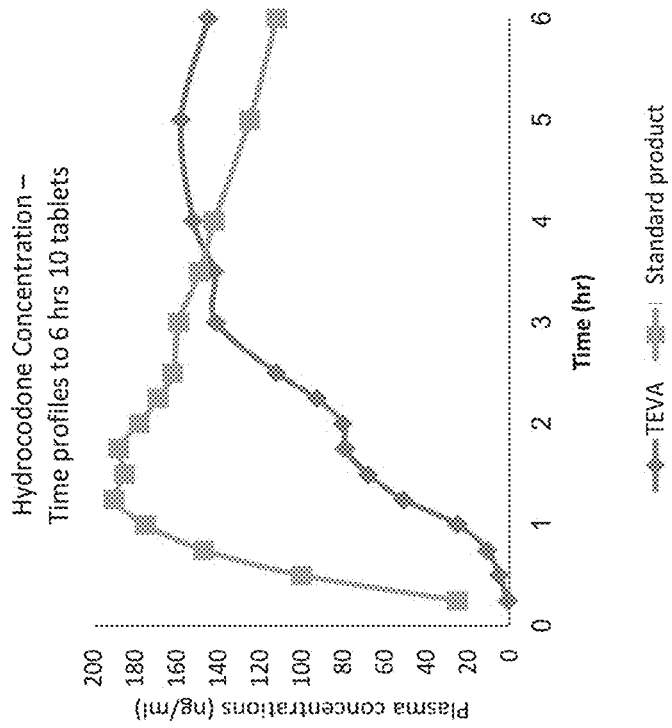
Figures 22A, 22B:
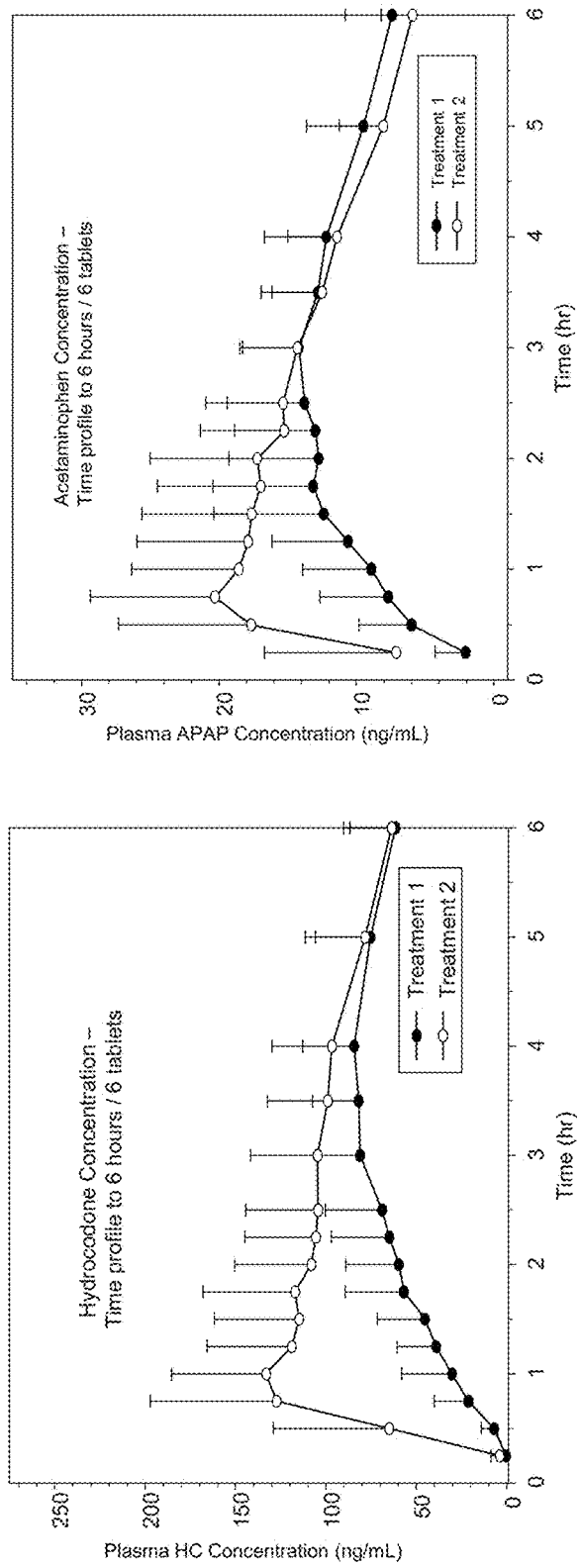
FIGS. 22a and 22b show two plots comparing pharmacokinetics of the test hydrocodone/acetaminophen formulation (Treatment 1) to a marketed/conventional hydrocodone/acetaminophen (Treatment 2), (FIG. 22a showing plasma levels of hydrocodone, and FIG. 22b showing plasma levels of acetaminophen), as a function of time following simultaneous administration to healthy naltrexone-blocked human male subjects of six hydrocodone bitartrate/acetaminophen tablets (10 mg/tablet hydrocodone bitartrate and 325 mg acetaminophen).
Figure 23B:
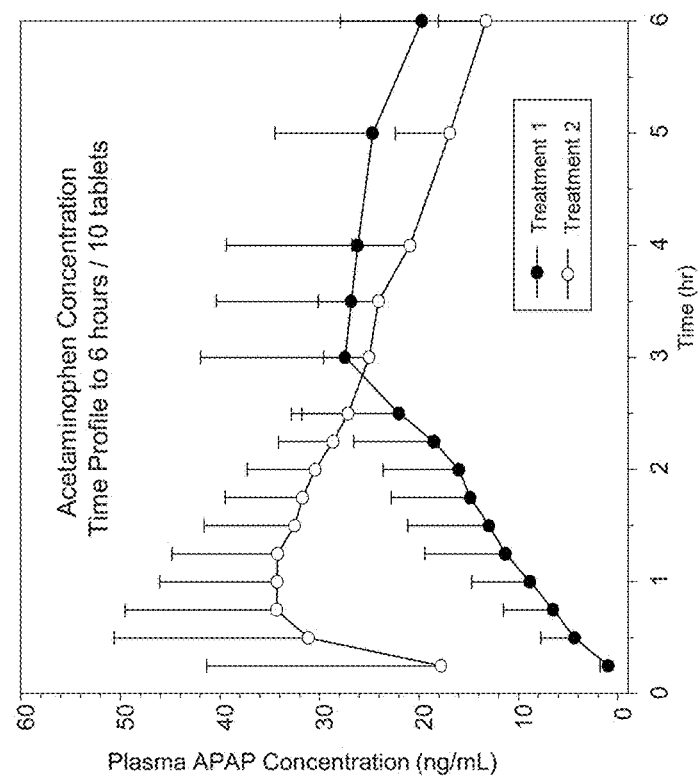
FIGS. 23a and 23b show two plots comparing pharmacokinetics of the test hydrocodone/acetaminophen formulation (Treatment 1) to a marketed/conventional hydrocodone/acetaminophen (Treatment 2), (FIG. 23a showing plasma levels of hydrocodone, and FIG. 23b showing plasma levels of acetaminophen), as a function of time following simultaneous administration to healthy naltrexone-blocked human male subjects of ten hydrocodone bitartrate/acetaminophen tablets (10 mg/tablet hydrocodone bitartrate and 325 mg acetaminophen).
Figure 23A:
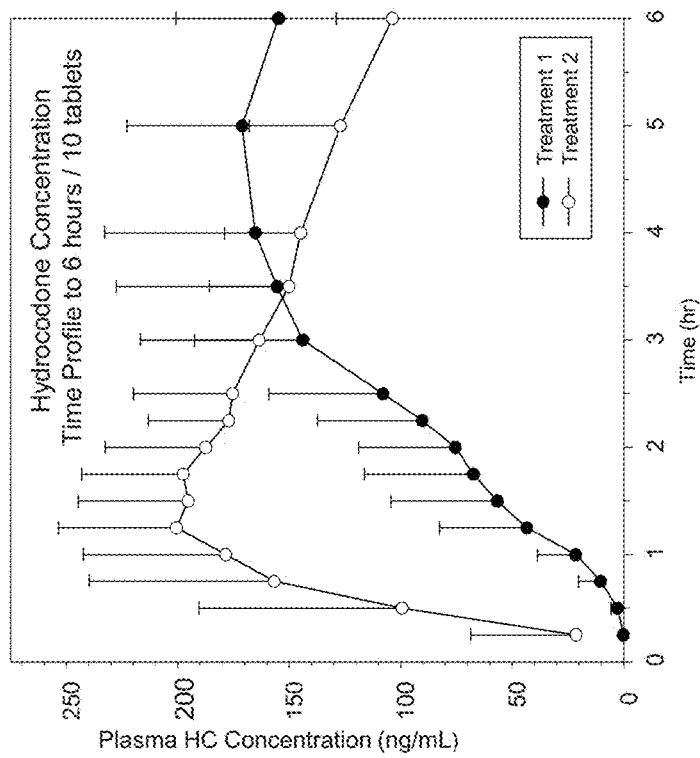
Figure 24C:
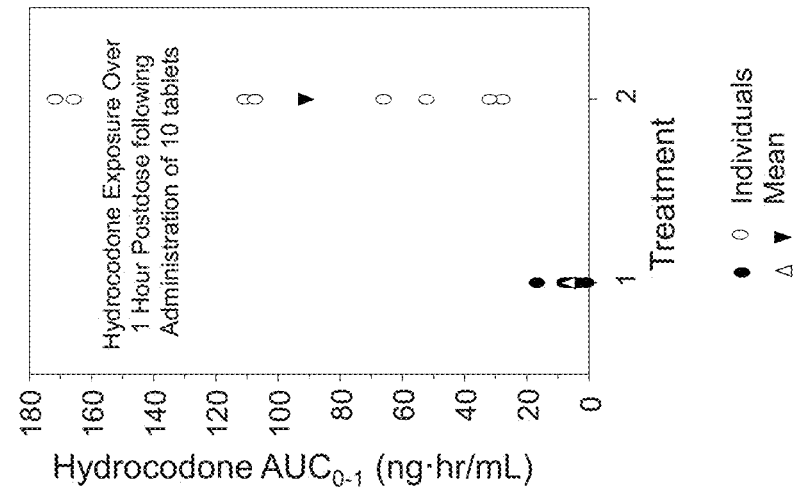
FIGS. 24a, 24b, and 24c show plots comparing the area under curve (AUC) of hydrocodone for of the test hydrocodone/acetaminophen formulation (Treatment 1) to a marketed/conventional hydrocodone/acetaminophen (Treatment 2) indicating hydrocodone exposure after 1 hour post-dose for simultaneous administration of 2 tablets (FIG. 24a), 6 tablets (FIG. 24b) and 10 tablets (FIG. 24c).
Figure 24B:
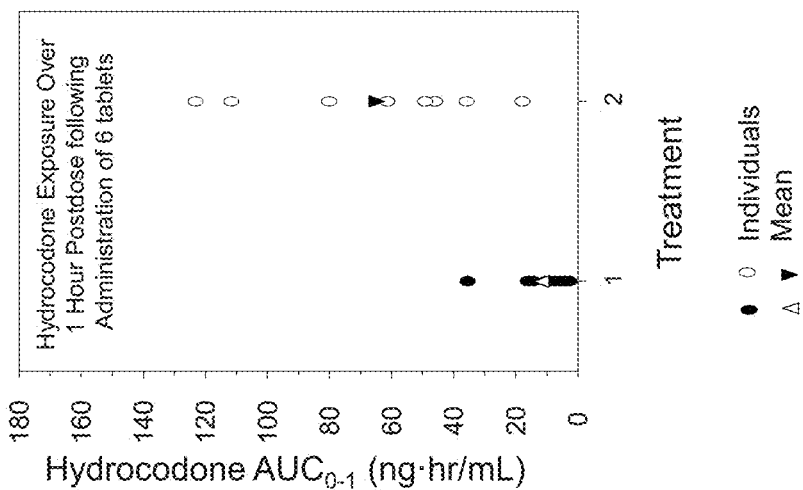
Figure 24A:
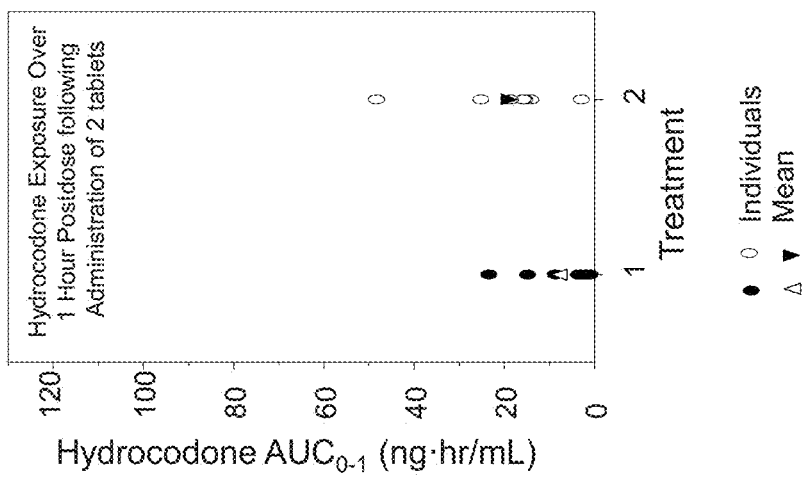
Figure 27:
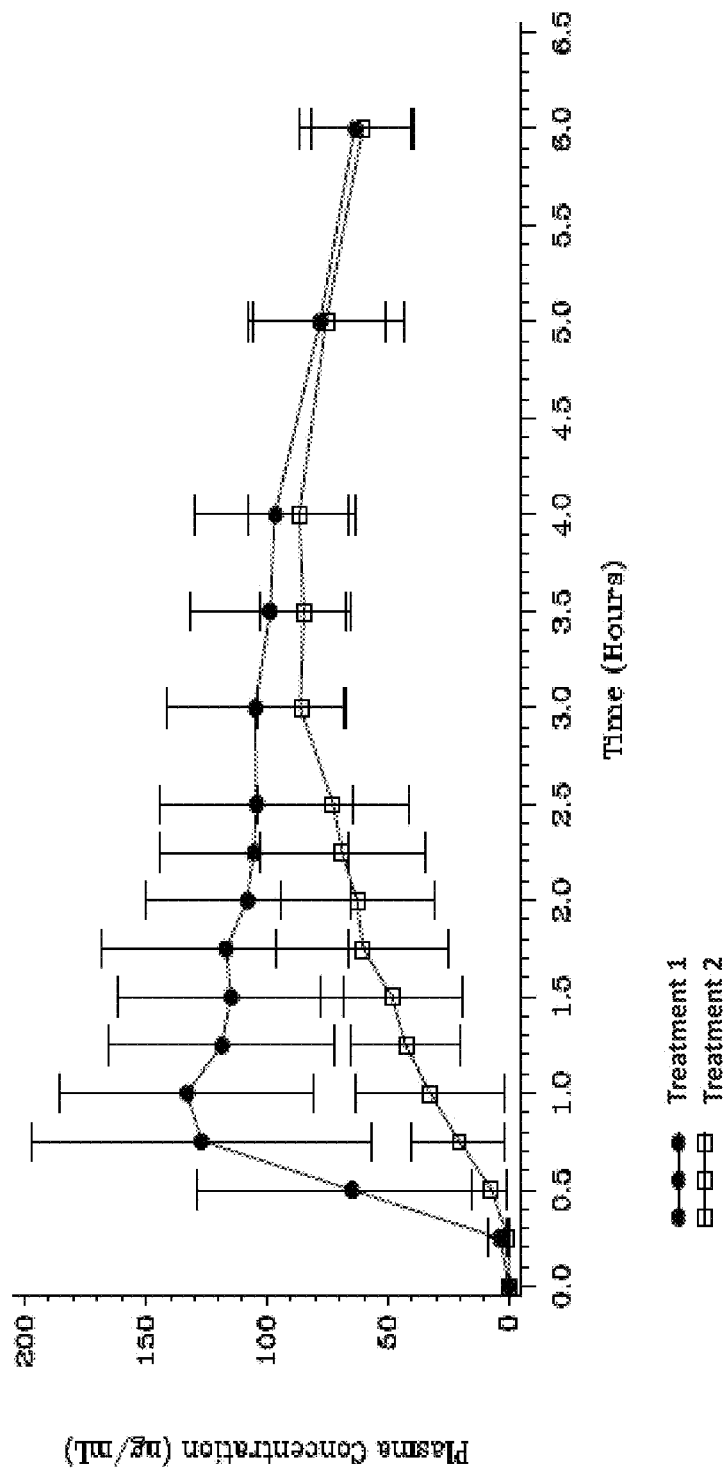
FIG. 27 shows a plot comparing pharmacokinetics of the test hydrocodone/acetaminophen formulation (Treatment 2) to a marketed/conventional hydrocodone/acetaminophen (Treatment 1), showing mean (±SD) plasma concentration-time profiles of hydrocodone over 6 hours following administration to healthy naltrexone-blocked human male subjects of 6 tablets of hydrocodone bitartrate/acetaminophen (10 mg/tablet hydrocodone bitartrate and 325 mg/tablet acetaminophen).
Figure 28:
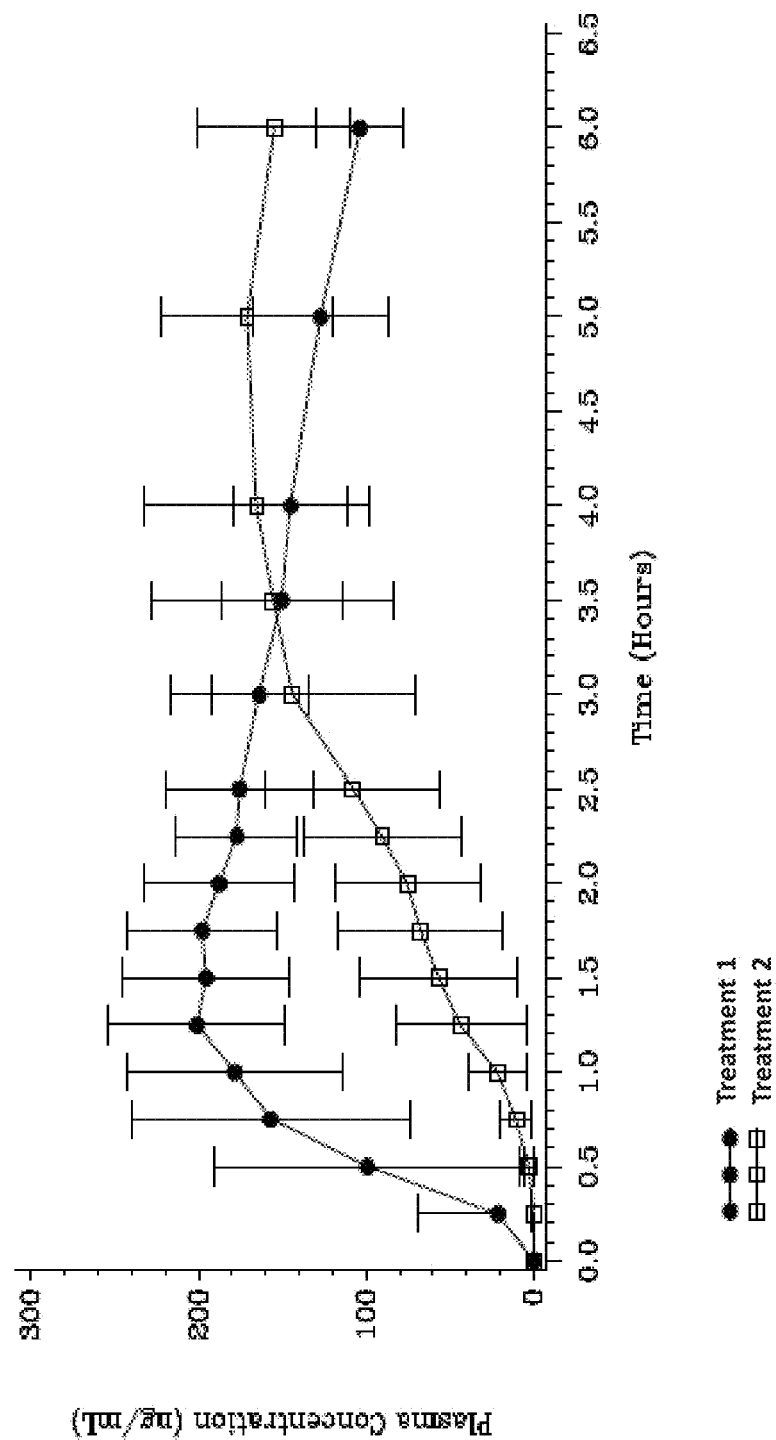
FIG. 28 shows a plot comparing pharmacokinetics of the test hydrocodone/acetaminophen formulation (Treatment 2) to a marketed/conventional hydrocodone/acetaminophen (Treatment 1), showing mean (±SD) plasma concentration-time profiles of hydrocodone over 6 hours following administration to healthy naltrexone-blocked human male subjects of 10 tablets of hydrocodone bitartrate/acetaminophen (10 mg/tablet hydrocodone bitartrate and 325 mg/tablet acetaminophen).
Figure 29:
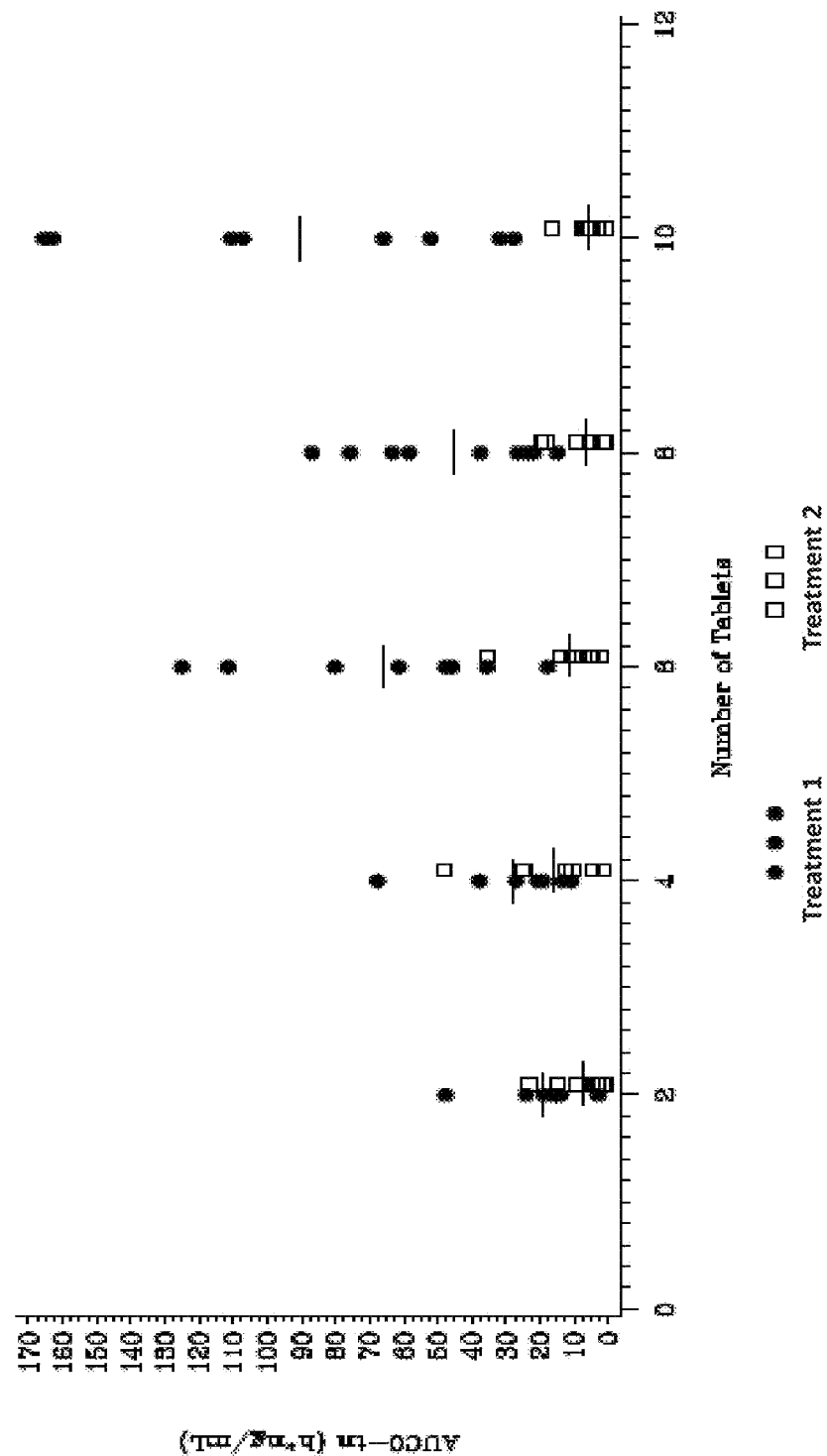
FIG. 29 shows a plot comparing the area under the plasma concentration curve (AUC) of hydrocodone over the first hour ($AUC_{0-1}$) for of the test hydrocodone/acetaminophen formulation (Treatment 2) to a marketed/conventional hydrocodone/acetaminophen (Treatment 1) indicating hydrocodone exposure after 2 hours post-dose for simultaneous administration of 2 tablets, 4 tablets, 6 tablets, 8 tablets and 10 tablets (10 mg/tablet hydrocodone bitartrate and 325 mg/tablet acetaminophen).
Figure 30:
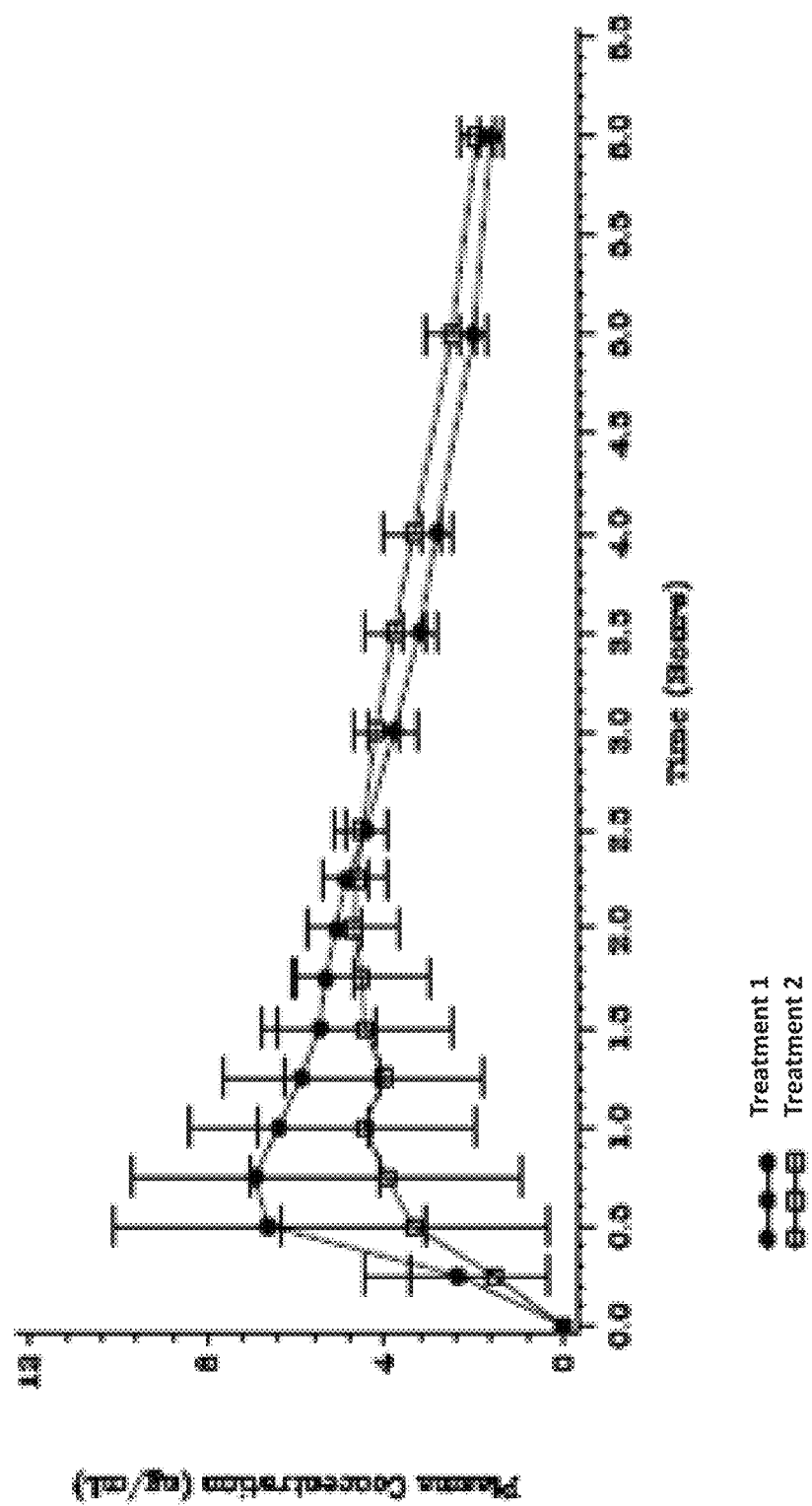
FIG. 30 shows a plot comparing pharmacokinetics of the test hydrocodone/acetaminophen formulation (Treatment 2) to a marketed/conventional hydrocodone/acetaminophen (Treatment 1), showing mean (±SD) plasma concentration-time profiles of acetaminophen over 6 hours following administration to healthy naltrexone-blocked human male subjects of 2 tablets of hydrocodone bitartrate/acetaminophen (10 mg/tablet hydrocodone bitartrate and 325 mg/tablet acetaminophen).
Figure 31:
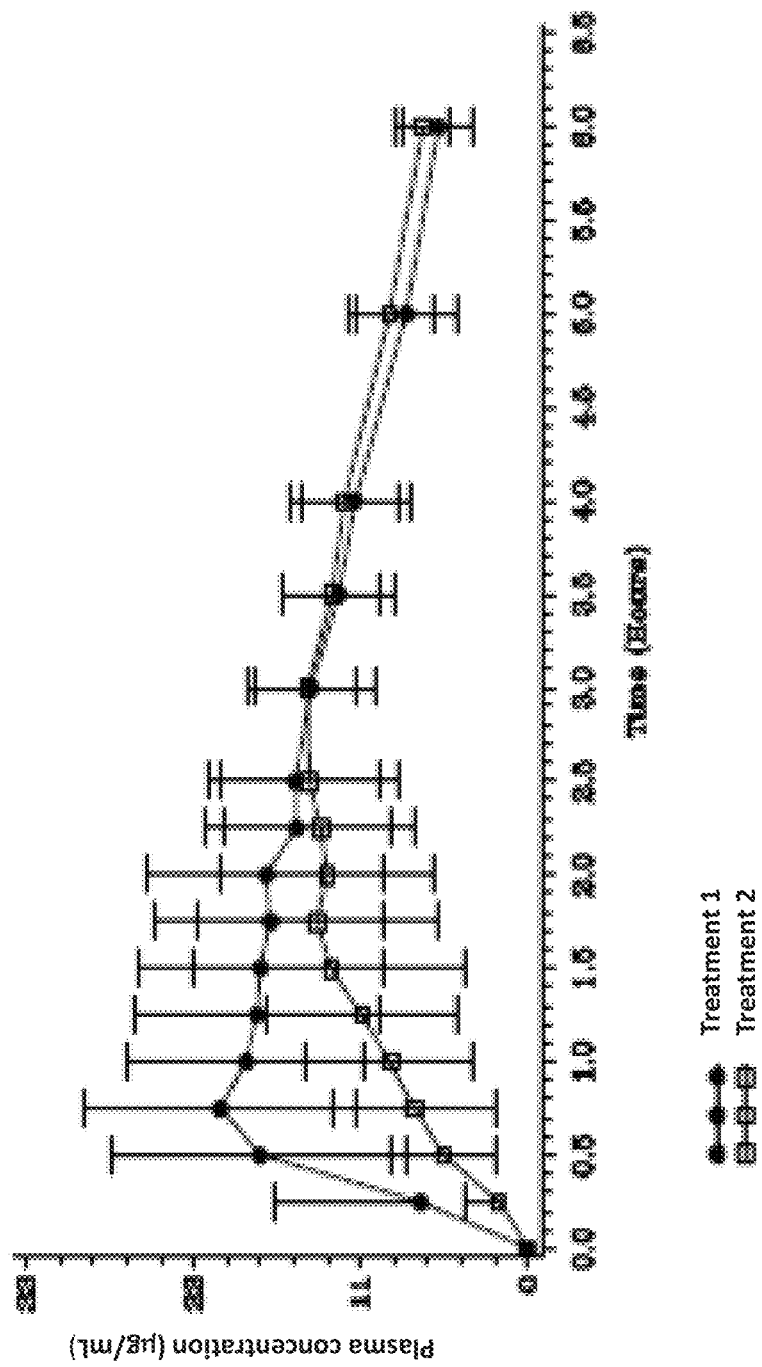
FIG. 31 shows a plot comparing pharmacokinetics of the test hydrocodone/acetaminophen formulation (Treatment 2) to a marketed/conventional hydrocodone/acetaminophen (Treatment 1), showing mean (±SD) plasma concentration-time profiles of acetaminophen over 6 hours following administration to healthy naltrexone-blocked human male subjects of 6 tablets of hydrocodone bitartrate/acetaminophen (10 mg/tablet hydrocodone bitartrate and 325 mg/tablet acetaminophen).
Figure 32:
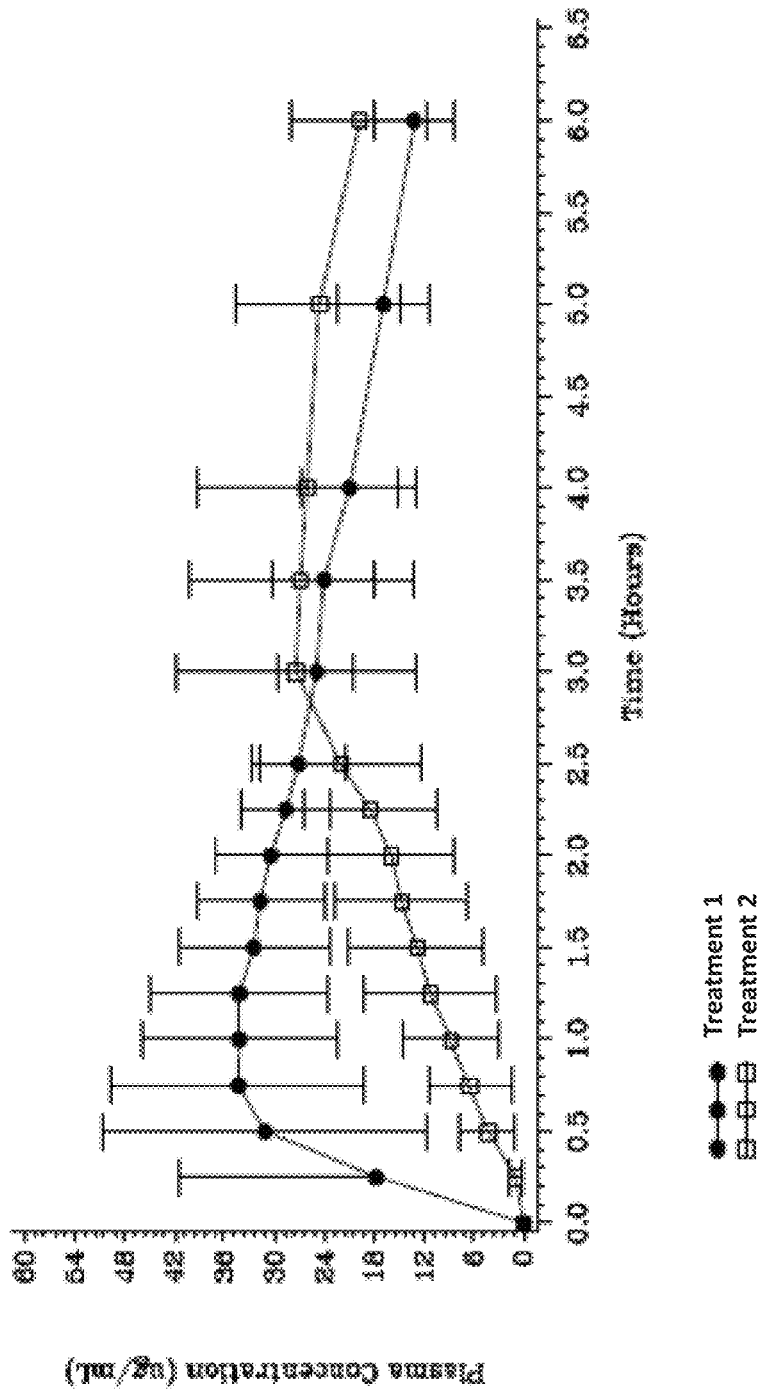
FIG. 32 shows a plot comparing pharmacokinetics of the test hydrocodone/acetaminophen formulation (Treatment 2) to a marketed/conventional hydrocodone/acetaminophen (Treatment 1), showing mean (±SD) plasma concentration-time profiles of acetaminophen over 6 hours following administration to healthy naltrexone-blocked human male subjects of 10 tablets of hydrocodone bitartrate/acetaminophen (10 mg/tablet hydrocodone bitartrate and 325 mg/tablet acetaminophen).
Figure 33:
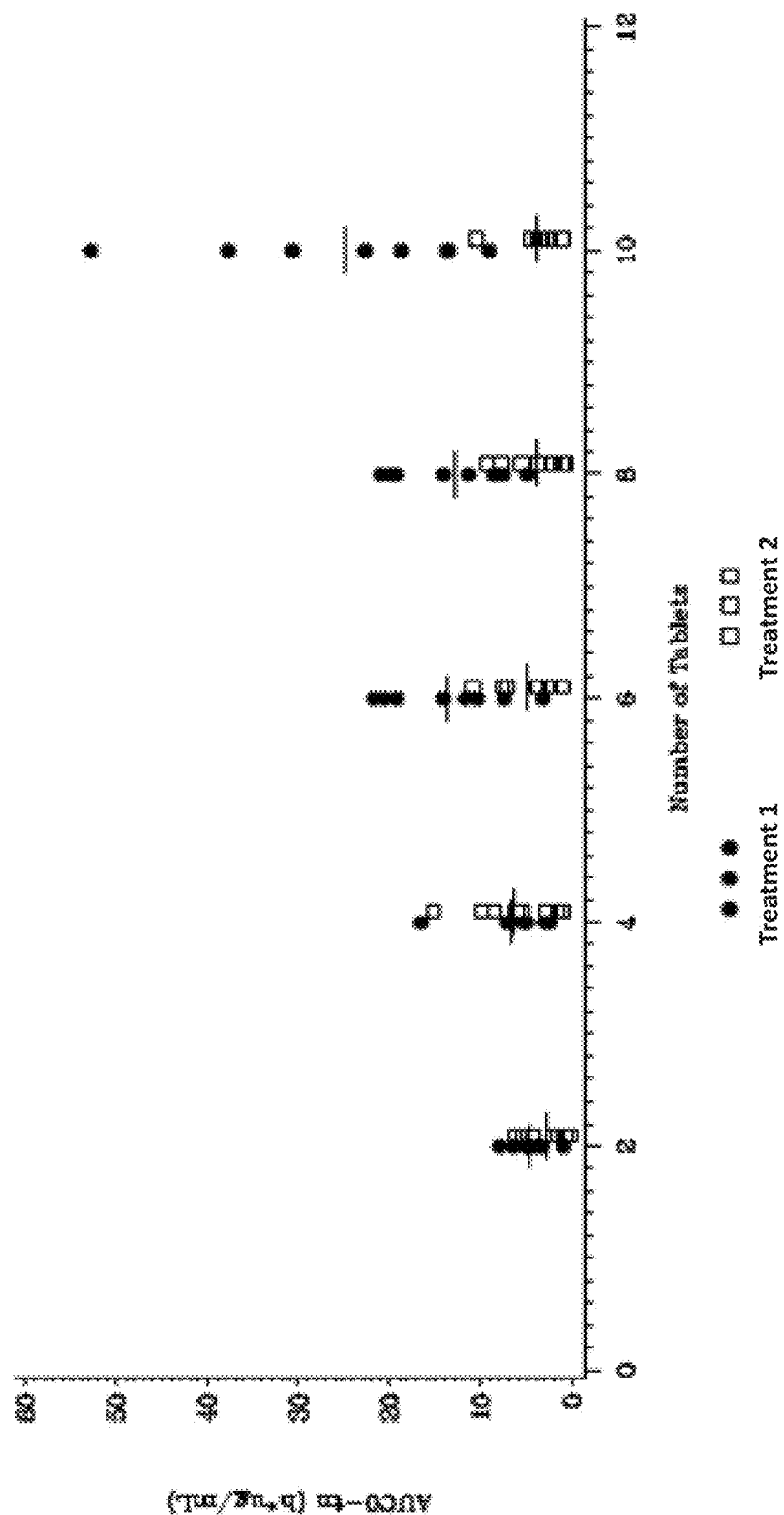
FIG. 33 shows a plot comparing the area under the plasma concentration curve (AUC) of acetaminophen over the first hour ($AUC_{0-1}$) for of the test hydrocodone/acetaminophen formulation (Treatment 2) to a marketed/conventional hydrocodone/acetaminophen (Treatment 1) indicating hydrocodone exposure after 2 hours post-dose for simultaneous administration of 2 tablets, 4 tablets, 6 tablets, 8 tablets and 10 tablets (10 mg/tablet hydrocodone bitartrate and 325 mg/tablet acetaminophen).
Figure 34A:
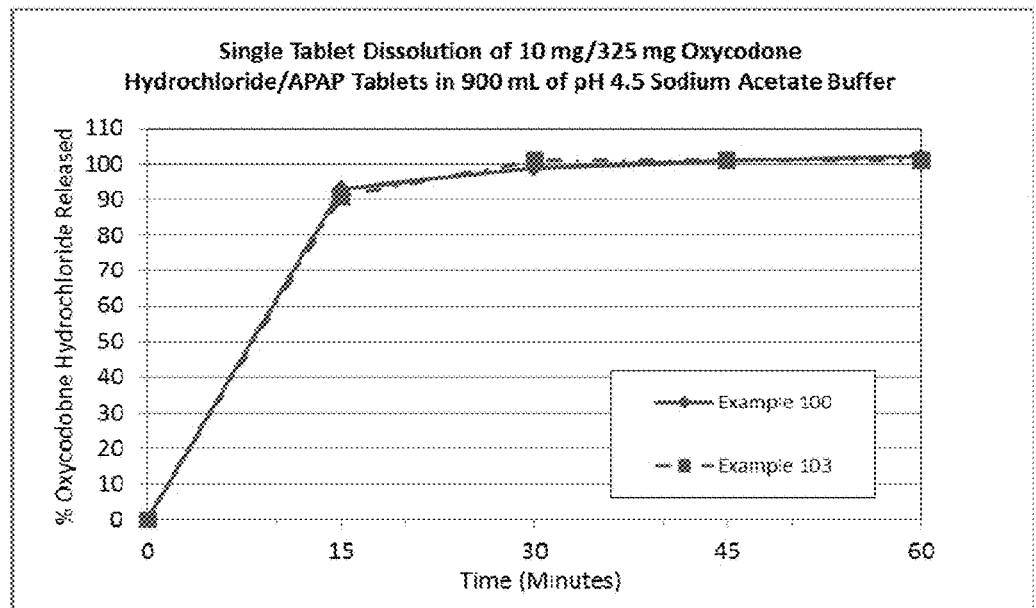
FIGS. 34A and 34B show plots of single tablet dissolution of oxycodone HCl/acetaminophen tablets prepared according to Examples 100 and 103 (10 mg/tablet oxycodone HCl and 325 mg/tablet acetaminophen) in pH 4.5 sodium acetate buffer as a function of time (FIG. 34A showing release of oxycodone HCl, and FIG. 34B showing release of acetaminophen).
Figure 34B:
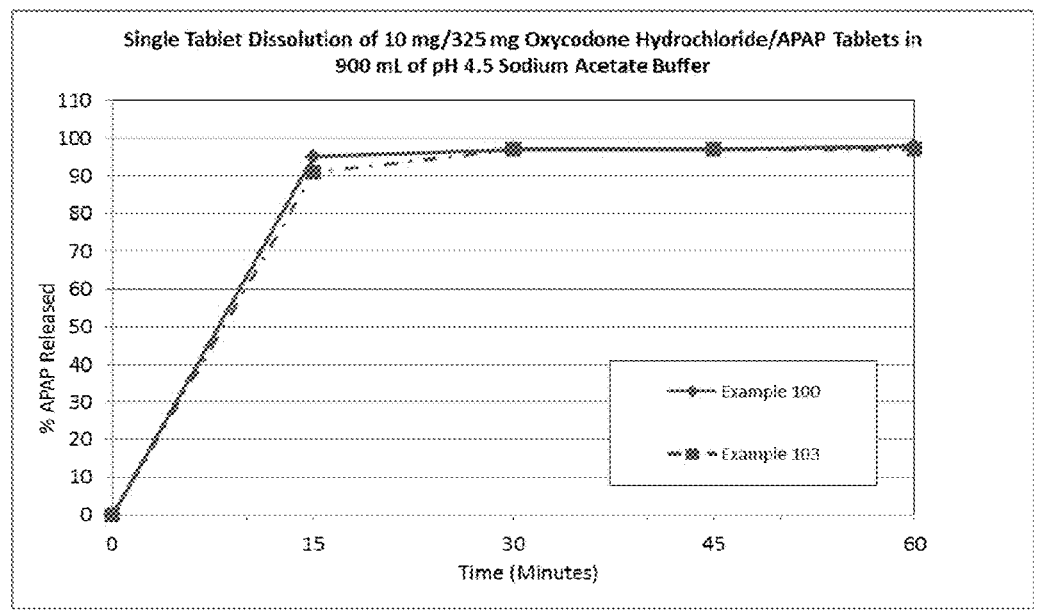
Figure 35A:
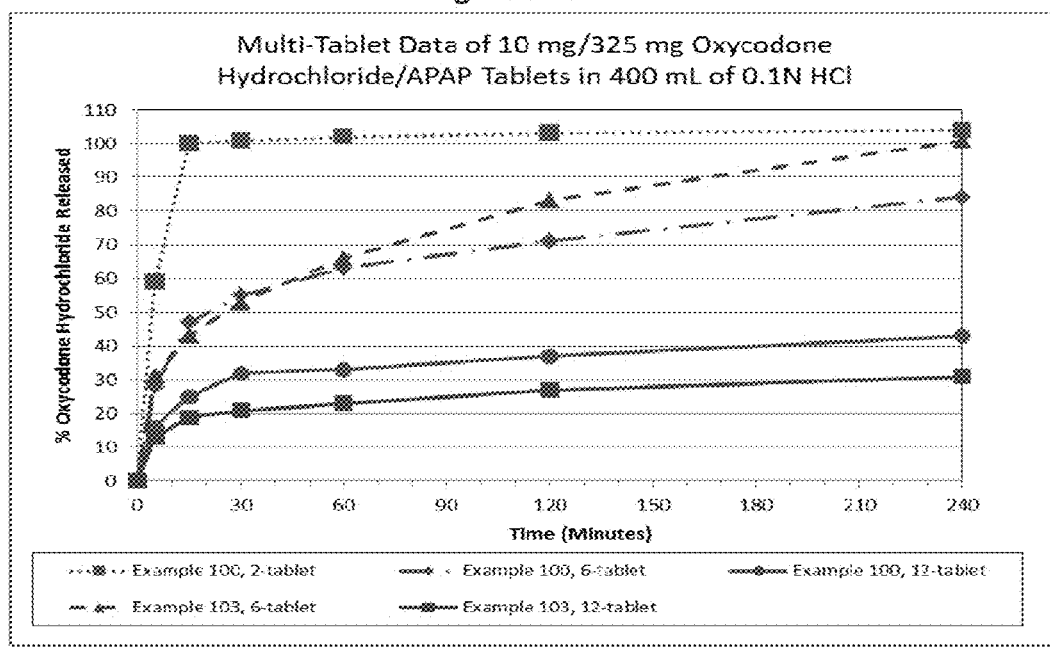
FIGS. 35A and 35B show plots of multiple tablet dissolution of oxycodone HCl/acetaminophen tablets prepared according to Examples 100 (data for release for 2-, 6- and 12-tablets) and 103 (data for 6- and 12-tablets) (10 mg/tablet oxycodone HCl and 325 mg/tablet acetaminophen) in 0.1N HCl as a function of time (FIG. 35A showing release profile for oxycodone HCl, and FIG. 35B showing the release profile for acetaminophen).
Figure 35B:
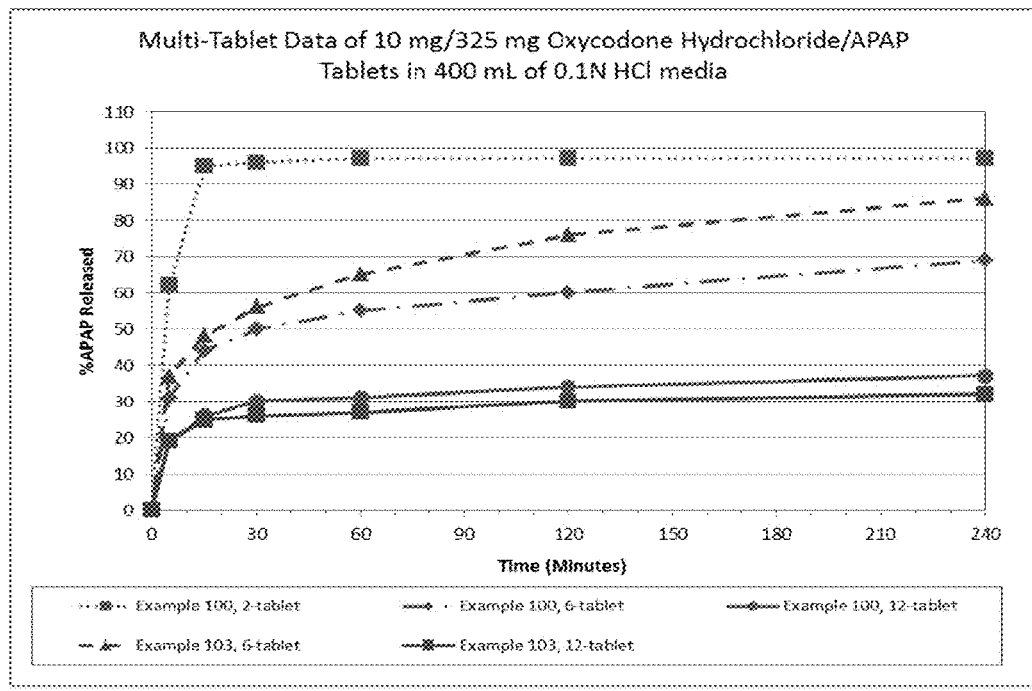
Figure 36A:
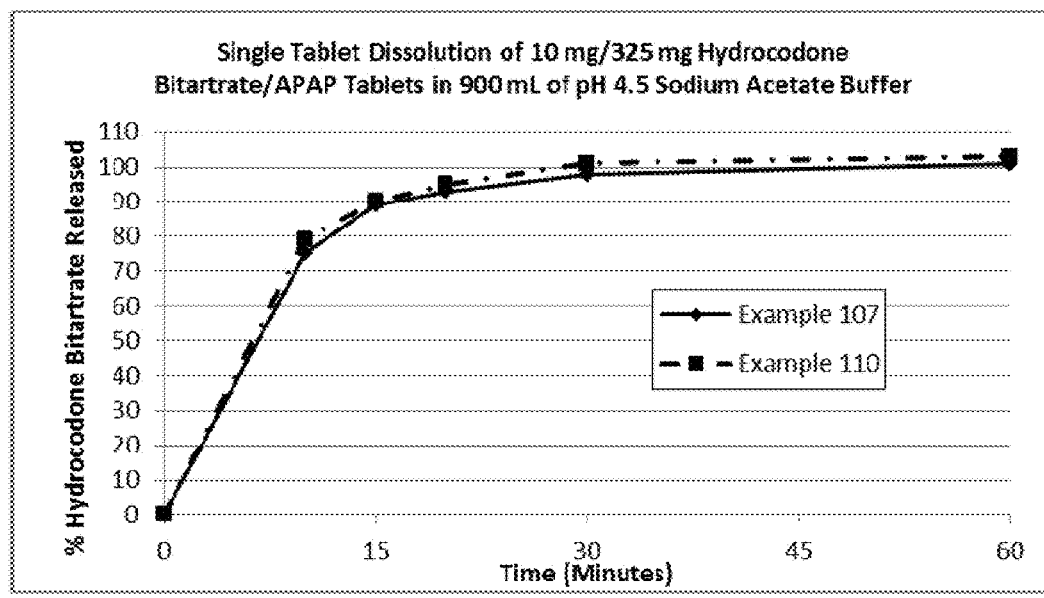
FIGS. 36A and 36B show plots of single tablet dissolution of hydrocodone bitartrate/acetaminophen tablets prepared according to Examples 107 and 110 (10 mg/tablet hydrocodone bitartrate and 325 mg/tablet acetaminophen) in pH 4.5 sodium acetate buffer as a function of time (FIG. 36A showing release of hydrocodone bitartrate, and FIG. 36B showing release of acetaminophen).
Figure 36B:
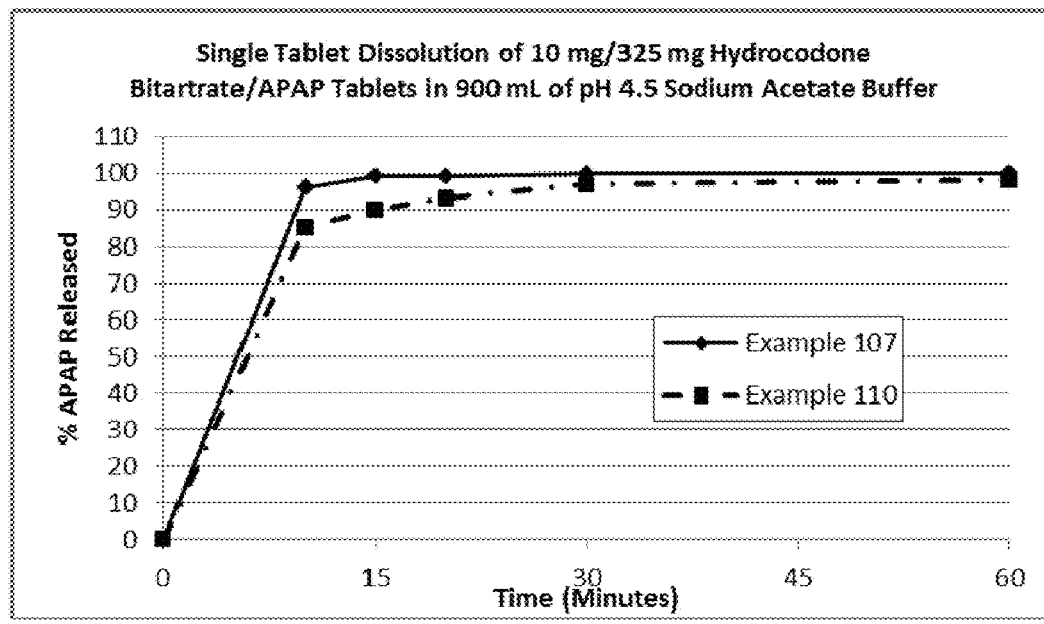
Figure 37A:
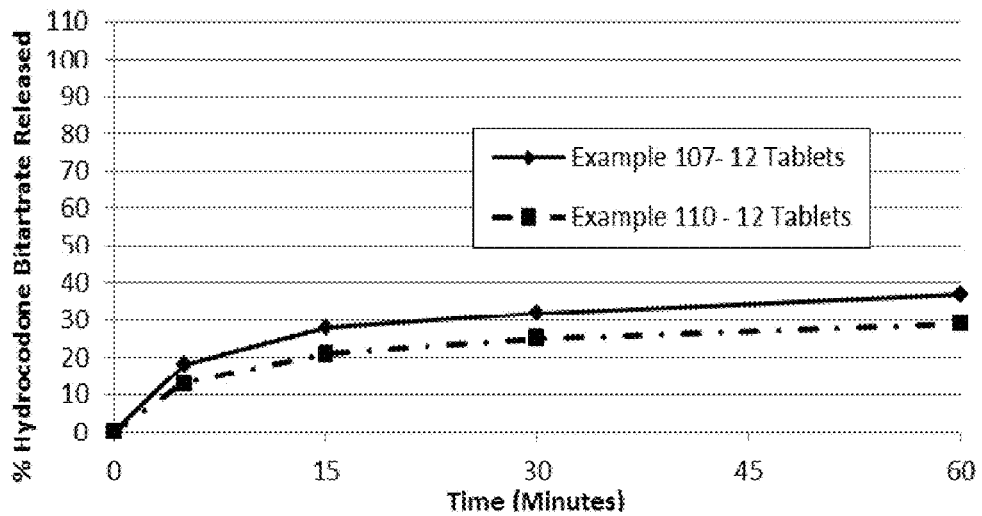
FIGS. 37A and 37B show plots of multiple tablet dissolution (12 tablets) of hydrocodone bitartrate/acetaminophen tablets prepared according to Examples 107 and 110 (10 mg/tablet hydrocodone bitartrate and 325 mg/tablet acetaminophen) in 0.1 N HCl as a function of time (FIG. 37A showing release profiles for hydrocodone bitartrate, and FIG. 37B showing the release profiles for acetaminophen).
Figure 37B:
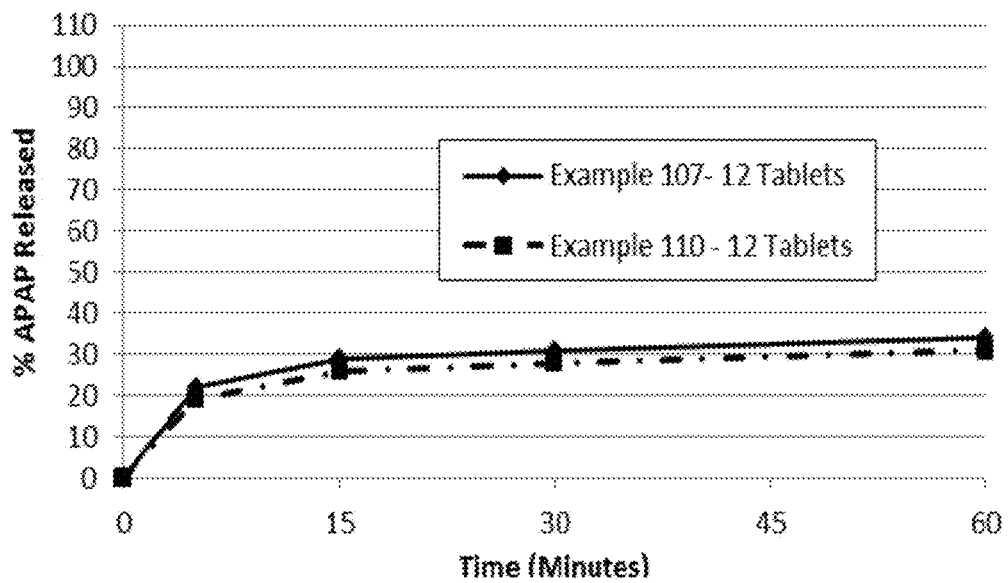
Figure 38:
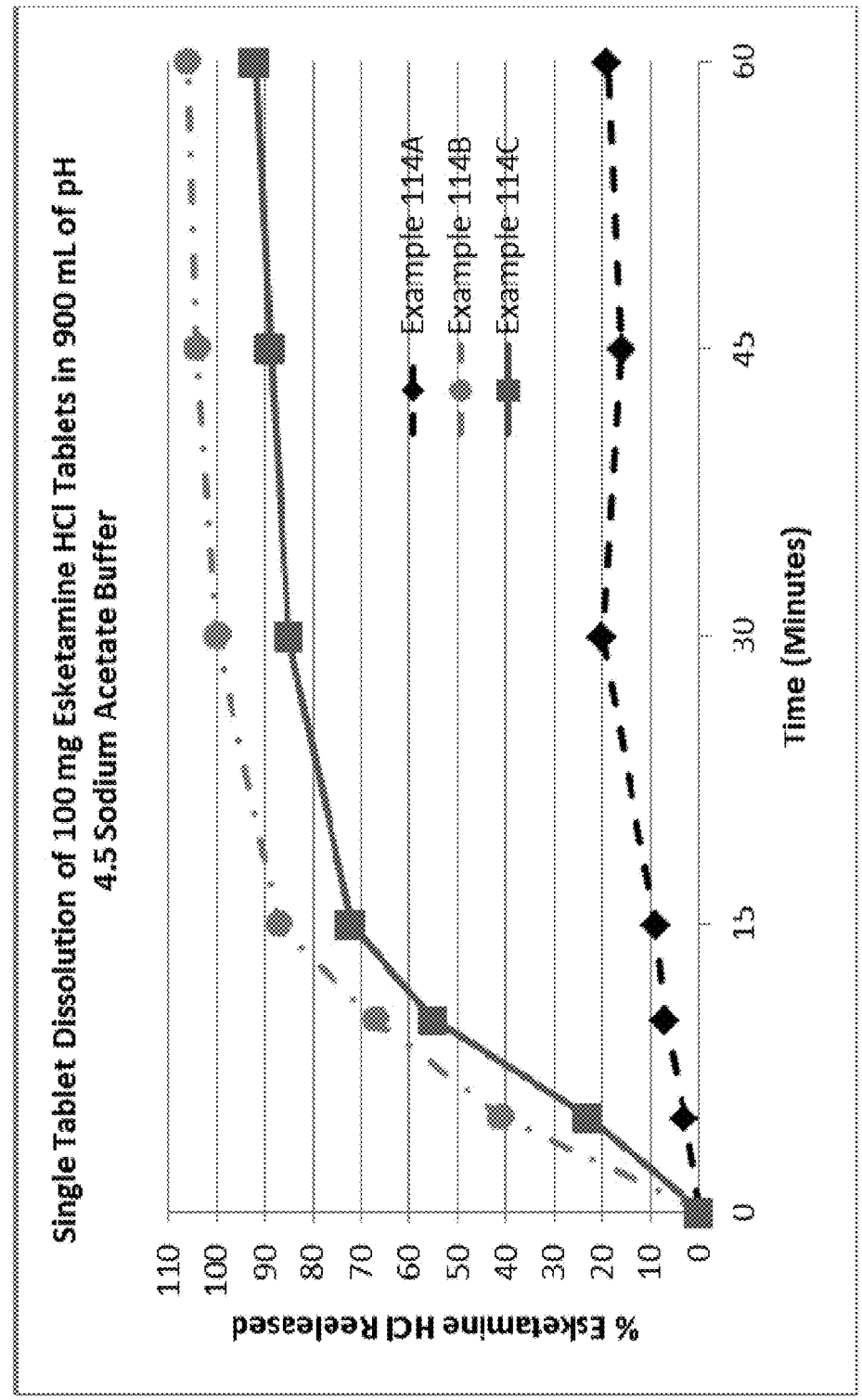
FIG. 38 shows plots of single tablet dissolution of Esketamine HCl tablets prepared according to Examples 114A, 114B and 114C (100 mg/tablet Esketamine HCl) in pH 4.5 sodium acetate buffer as a function of time.

In addition, in vitro testing as described herein indicates that exemplary dosage forms provide deterrence against abuse by multi-tablet dosing, even if the dosage form is crushed prior to administration/testing. Specifically, in vitro testing was performed by conducting dissolution testing of multiple (twelve) crushed tablets according to the same protocol as described above for testing intact tablets (i.e., in 300 or 900 milliliters of 0.1N HCl maintained at 37 degrees Celsius using a 50 RPM paddle speed). See, Example 93 and FIGS. 14-15 herein. As shown in FIGS. 14-15, the percentage of the API (the opioid and APAP) that was released in the media was reduced with an increase in the number of crushed tablets. This data suggests that the dosage forms are effective to prevent increased levels of API uptake in an individual who would ingest multiple crushed tablets, and thereby prevent or reduce the risk of an overdose of the API. The tablets used in Example 94, which provided the data shown in FIGS. 14-15 were prepared as per Example 93.)

In vivo testing in naloxone-blocked healthy human male subjects has been undertaken. This testing was designed to determine if previous in vitro dissolution data utilizing multiple tablets translates to humans. Dose escalation from 2 tablets through 10 tablets was carried out with no safety signals identified.

Preliminary results demonstrated that simultaneous administration of 2 tablets was similar to administration of 2 tablets of a commercially available hydrocodone/acetaminophen combination product (NORCO). The test formulation differentiated from the commercially available hydrocodone/acetaminophen combination product over the first 4 hours for hydrocodone at a dose of ≥6 tablets. Findings were similar for acetaminophen.

Preliminary PK data from an early study for the two through ten tablet cohorts provided the data included herein in FIGS. 16 to 27(*a-c*). In the Figures, "Treatment 1" refers to administration of hydrocodone/acetaminophen (10 mg/325 mg) formulated according to the invention described herein. "Treatment 2" refers to administration of hydrocodone/acetaminophen (10 mg/325 mg) in a conventional commercially available immediate release formulation.

FIGS. 16 to 25(*a-c*) were prepared prior to completion of the study. FIGS. 16 to 19 provide only preliminary data and FIGS. 20 to 25(*a-c*) provide final data from the first phase of this testing. The PK results may suggest that when opioid formulations as described herein are administered as recommended (<2 tablets), those formulations will have properties consistent with an immediate release opioid, but when taken at supra-therapeutic doses (>6 tablets), the formulations will behave more like an extended release opioid formulation.

The final results from the completed study were consistent with the preliminary findings. Following administration of hydrocodone/acetaminophen (10 mg/325 mg) (formulated according to the invention) or a conventional commercially available immediate release formulation (NORCO), overall exposure to hydrocodone and acetaminophen (as assessed by AUC0-∞) was generally comparable. However, early systemic exposure to hydrocodone and acetaminophen was lower and peak concentrations occurred later following administration of the formulation according to the invention—as compared with the conventional formulation. The relative difference between the 2 products' pharmacokinetic profiles became substantially larger as the number of tablets administered was increased. The differences were most notable over the first 1 to 2 hours after dosing and were sustained through approximately 3 to 6 hours after dosing for the increased tablet administrations.

Accordingly, dosage forms as described herein provide a method of preventing or attenuating a short-term concentration spike of the drug in the bloodstream of a patient who is prescribed the drug, or in the bloodstream of an abuser who consumes the drug for recreational purposes, in the event that a patient or the abuser intentionally or unintentionally consumes a supratherapeutic dose of the drug. Thus, dosage forms as described herein can provide a method whereby a drug overdose may be prevented reduced or attenuated, when a patient intentionally or unintentionally consumes a supratherapeutic dose of the drug. Also, in some instances, dosage forms as described herein may provide a greater amount of time for medical intervention in the case of intentional or accidental overdose.

By "supratherapeutic is meant a dose that exceeds what would normally be prescribed for therapy, for example a dose in excess of two, three, four, five, six, seven, eight, nine, ten, eleven or twelve individual dose units (e.g., tablets, capsules, etc.).

As one type of abuse deterrent feature, a dosage form as described can include one or more gelling polymers. A gelling polymer can act as an abuse deterrent feature by compromising abuse practices wherein an active pharmaceutical ingredient of a dosage form is being dissolved in a small volume of solvent or being accessible or easily isolatable if combined with solvent with the gelling polymer also present. A gelling polymer can also deter or prevent abuse of an API in a dosage form by increasing the viscosity of a combination of the ground dosage form with solvent (especially a "small volume" of solvent) to a viscosity that is sufficiently high to prevent the combination or the API from being taken up by and injected using a syringe. A preferred gelling polymer contained in a ground dosage form, when exposed to a limited volume (or "small volume") of solvent such as a $C_{1-4}$ alcohol (e.g., ethanol or methanol) or water, can form a non-injectable mass ranging from an insoluble mass, to a gel, to a viscous slurry, each of which exhibits a viscosity that substantially prevents either uptake by or injection from a needle of a hypodermic syringe.

Suitable gelling polymers include one or a combination of polymers that, as part of a dosage form, upon contact of the dosage form with a small volume of solvent, will absorb the solvent and swell to form a viscous or semi-viscous substance that significantly reduces or minimizes the amount of free solvent that can contain an amount of a solubilized API and that can be drawn into a syringe. The gelled polymer can also reduce the overall amount of drug extractable with the solvent by entrapping the drug in a gel matrix.

The gelling polymer can be present in the dosage form at a location and in an amount that together allow the gelling polymer to produce a viscous gel in the event of an abuser grinding the dosage form and combining the crushed dosage form with a solvent. On the other hand, the gelling polymer, as present in the dosage form, will preferably not interfere with desired dissolution of the dosage form, the desired release (immediate release) of API from the dosage form, or the uptake of the API by a patient ingesting the intact immediate release dosage form for an intended therapeutic purpose. An exemplary location for the gelling polymer is in a coated particle that also includes active pharmaceutical ingredient, such as in a core or in a layer coated to surround the core; wherein an amount of active pharmaceutical ingredient is contained in either the core, or a layer coated to surround the core, or is contained in both. Another exemplary location is within a matrix used to form a compressed tablet, a capsule (e.g., a compressed capsule), a caplet, or another type of dosage form that contains a coated particle that contains active pharmaceutical ingredient. Gelling polymer may also be present, in the core, or in a layer surrounding the core, of a coated particle that does not include an active pharmaceutical ingredient.

The gelling polymer can be present in a dosage form at any desired amount and at any portion of, or location in a dosage form structure. The amount of gelling polymer can be any useful amount, meaning an amount that can produce an abuse-deterrent viscous mixture or gel if the dosage form is crushed, ground, powdered, etc., and mixed with solvent. A useful amount of total gelling polymer in a dosage form may be in a range from 0.5 to 90 weight percent gelling polymer based on a total weight of the dosage form, e.g., from 0.7 to 20, or 2 to 15 weight percent gelling polymer based on total weight of the dosage form.

These amounts of total gelling polymer can be present in one or more locations of the dosage form, to achieve the specified total amount, such as in a portion at a coated particle (e.g., core), a matrix (e.g., compressed matrix) structure that supports and contains the coated particles, or in both the coated particles and the matrix.

A core (uncoated) of a core-shell particle can contain any useful amount of gelling polymer, such as from 0 up to and including 100 percent gelling polymer in a core of a core-shell particle, e.g., from 10 to 95 weight percent gelling polymer based on a total weight of the core, such as from 40 to 85 or 50 to 75 weight percent gelling polymer based on total weight core.

Described in terms of total weight of a dosage form, an amount of gelling polymer present in a core of a core shell polymer may be, e.g., in a range from 0.5 to 15 weight percent gelling polymer (present in the core) per total weight of the dosage form, such as from 1 to 10 weight percent gelling polymer (present in the core) per total weight dosage form. An amount of gelling polymer present in a matrix of a dosage form may be any desired amount, such as an amount in a range from 0.5 to 15 weight percent gelling polymer (as excipient in a matrix) based on a total weight of the dosage form, such as from 1 to 10 weight percent gelling polymer (present as excipient in a matrix) based on total weight dosage form.

A useful gelling polymer can be any polymeric material that exhibits the ability to retain a significant fraction of adsorbed solvent in its molecular structure, e.g., the solvent being a solvent otherwise useful by an abuser to extract API from a dosage form or a crushed or powdered dosage form, the solvent for example being water or a $C_1$ to $C_4$ alcohol such as ethanol or methanol, etc. Examples of gelling polymers include materials that can swell or expand to a very high degree when placed in contact with such a solvent. The swelling or expansion may cause the gelling polymer to experience from a two- to one-thousand-fold volume increase from a dry state. More specific examples of gelling polymers include swellable polymers sometimes referred to as osmopolymers or hydrogels. The gelling polymer may be non-cross-linked, lightly crosslinked, or highly crosslinked. The crosslinking may involve covalent or ionic bonds with the polymer possessing the ability to swell in the presence of a solvent, and when cross-linked will not dissolve in the solvent.

A gelling polymer, upon dissolution or dispersion in an aqueous solution or dispersion (e.g., water) at a concentration of 2% w/w (based on the dry material), creates a solution/dispersion with a viscosity of from about 100 to about 200,000 mPa·s (e.g., 4,000 to 175,000 mPa·s, and 4,000 to 50,000 mPa·s$) as measured at 20 degrees Celsius (+/−0.2 degree Celsius) using the analysis method described in the USP 33 monograph for hypromellose (incorporated herein by reference).

Generally suitable gelling polymers include pharmaceutically acceptable polymers that undergo an increase in viscosity upon contact with a solvent, as described. Various examples of polymers are known to be useful in this manner, generally including natural and synthetic starches (i.e., modified or pregelatinized modified starch), natural and synthetic celluloses, acrylates, and polyalkylene oxides. Examples of natural starches include natural starches include corn starch, potato starch, rice starch, tapioca starch and wheat starch, hydroxypropyl starch such as hydroxypropyl corn starch, hydroxypropyl pea starch and hydropropyl potato starch (derivative of natural starch). Examples of synthetic starches, i.e., modified or pregelatinized modified starch, include acetylated distarch adipate, waxy maize basis, acid-treated maize starch, acid-treated waxy maize starch, distarch phosphate, waxy maize basis, oxidized waxy maize starch, and sodium octenyl succinate starch. Examples of celluloses include carboxymethylcellulose calcium, carboxymethylcellulose sodium, ethycellulose, methylcellulose, cellulose ethers such as hydroxypropyl cellulose, hydroxyethylcellulose, hydroxyethylmethyl cellulose, hydroxypropyl methyl cellulose, carboxymethylcellulose sodium, and low substituted hydroxypropyl cellulose. Examples of acrylates include Eudragit RS, RL, NE, NM. Examples of polyalkylene oxides include polyethylene oxide such as POLYOX N10, N80, N60K, WSR-1105 LEO, or WSR-301 LEO, or WSR-303 LEO.

Accordingly, examples of suitable gelling polymers include polyethylene oxide, polyvinyl alcohol, hydroxypropyl methyl cellulose, hydroxypropyl cellulose, methyl cellulose, hydroxyethylmethylcellulose, sodium carboxymethylcellulose, hydroxyethylcellulose, polyacrylic acid and polyvinyl carboxy polymers such as those commercially available under the trade name Carbopol®, and other high molecular weight polymers capable of attaining a viscosity level effective to prevent uptake in a syringe, if combined with a small volume of solvent as described.

Other examples of suitable gelling polymers can include, if of sufficiently high molecular weight: ethylcellulose, cellulose acetate, cellulose acetate propionate, cellulose acetate butyrate, cellulose acetate phthalate and cellulose triacetate, cellulose ether, cellulose ester, cellulose ester ether, cellulose; acrylic resins comprising copolymers synthesized from acrylic and methacrylic acid esters, for example acrylic acid and methacrylic acid copolymers, methyl methacrylate copolymers, ethoxyethyl methacrylates, cyanoethyl methacrylate, poly(acrylic acid), poly (methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

Exemplary gelling polymers can include natural polymers such as those derived from a plant or animal, as well as polymers prepared synthetically. Examples include polyhydroalkylcellulose having a molecular weight greater than 50,000; poly(hydroxy-alkylmethacrylate) having a molecular weight of from 5,000 to 5,000,000; poly(vinyl-pyrrolidone) having a molecular weight of from 100,000 to 3,000,000; anionic and cationic hydrogels; poly(electrolyte) complexes; poly(vinyl alcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; water-swellable copolymer produced by a dispersion of finely divided copolymer of maleic anhydride with styrene, ethylene, propylene, or isobutylene; water swellable polymer of N-vinyl lactams; and the like.

Other polymers useful as a gelling polymer include pectin having a molecular weight ranging from 30,000 to 300,000;

polysaccharides such as agar, acacia, karaya, tragacanth, algins and guar; polyacrylamides; water-swellable indene maleic anhydride polymers; Goodrite® polyacrylic acid having a molecular weight of 80,000 to 200,000; Polyox® polyethylene oxide polymers having a molecular weight of 100,000 to 7,000,000; starch graft copolymers; Aqua-Keep® acrylate polymers with water absorbability of 400 times its original weight; diesters of polyglucan; a mixture of cross-linked polyvinyl alcohol and poly(-vinyl-2-pyrrolidone); poly(ethylene glycol) having a molecular weight of 4,000 to 100,000.

In various specific embodiments, a gelling polymer may be, or may include, hydroxypropyl methyl cellulose (e.g., Hypromellose or HPMC), and hydroxy methyl cellulose, methyl cellulose, hydroxyethylmethyl cellulose, and sodium carboxymethyl cellulose. The hydroxypropyl methyl cellulose can have a molecular weight ranging from 10,000 to 1,500,000. Examples of suitable, commercially available hydroxypropyl methylcellulose polymers include HPMC K100M, Methocel K100LV and Methocel K4M.

A specific class of gelling polymer is the class of carbomer polymers, which are polymers derived from acrylic acid (e.g., acrylic acid homopolymers) and crosslinked with polyalcohol allyl ethers, e.g., crosslinked with polyalkenyl ethers of pentaerythritol or sucrose. Carbomer polymers are hydrophilic and are not substantially soluble in water. Rather, these polymers swell when dispersed in water forming a colloidal, mucilage-like dispersion. Carboxyl groups provided by acrylic acid residues of the polymer backbone are responsible for certain behavior of the polymers. Particles of this polymer can be viewed as a network structure of polymer chains interconnected by crosslinks. The structure can swell in water by up to one thousand times of an original (dry) volume (and ten times an original diameter of polymer particles) to form a gel when exposed to a pH environment above 4-6. The pKa of these polymers can be 6±0.5. Accordingly, carboxylate groups pendant from the polymer backbone can ionize at a pH above 6, producing a repulsion between the negatively-charged particles, which adds to the swelling of the polymer if exposed to solvent at this pH range. For this reason, a dosage form as described herein can preferably include a pH adjuster in an amount and location within the dosage form to raise the pH of a carbomer polymer to at least 6, to substantially neutralize the carboxylate groups.

A suitable amount of a pH adjuster may be from about 1 to about 10 millimoles, or from about 5 to about 9 millimoles, or from about 6 to about 8 millimoles, or from about 7 to about 7.5 millimoles of the pH adjuster per gram of the carbomer polymer that is present in the dosage form. According to some embodiments, a suitable amount of a pH adjuster may be from about 50 to about 400 millimoles; or from about 50 to about 350 millimoles; or from about 50 to about 250 millimoles; or from about 50 to about 150 millimoles; or from about 50 to about 100 millimoles of the pH adjuster per gram of the carbomer polymer that is present in the dosage form. According to other embodiments, a suitable amount of a pH adjuster may be from about 200 to about 400 millimoles; or from about 300 to about 400 millimoles of the pH adjuster per gram of the carbomer polymer. According to certain embodiments, a suitable amount of a pH adjuster may be from about 50 to about 70 millimoles; or about 60 millimoles of the pH adjuster per gram of the carbomer polymer. According to certain embodiments, a suitable amount of a pH adjuster may be from about 300 to about 350 millimoles, or about 310 millimoles of the pH adjuster per gram of the carbomer polymer.

According to some embodiments, the pH adjuster is present in a dosage form according to the invention in an amount that is from about 1 to about 5 percent by weight, or from about 2 to about 4 percent by weight, or about 3 to 4 percent by weight based on the total weight of the dosage form. According to some other embodiments, the pH adjuster is present in a dosage form according to the invention in an amount that is from about 5 to about 20 percent by weight. According to some of these embodiments, the pH adjuster is present in an amount that is from about 5 to about 15 percent by weight, or from about 10 to about 15 percent by weight based on the total weight of the dosage form; or from about 9 to about 14 percent by weight. According to certain embodiments, the pH adjuster is present in an amount that is from about 9 to about 11 percent by weight; or from about 12 to about 14 percent by weight; or about 10 percent by weight, or about 13 percent by weight.

Carbomer polymers are often referred to in the art using alternative terminology such as, for example, carbomer homopolymer, acrylic acid polymers, carbomer, Carbopol, carboxy polymethylene, carboxyvinyl polymer, Pemulen, polyacrylic acid, and poly(acrylic acid), The USP-NF lists three umbrella monographs i.e. for "carbomer copolymer," for "carbomer homopolymer," and for "carbomer interpolymer."

Certain carbopol (carbomer) polymers that may be useful as a gelling polymer can have an average equivalent weight of 76 per carboxyl group. Examples of suitable commercially available carbomers include Carbopol® 934, 934P NF, Carbopol® 974P NF and Carbopol® 971P NF, Carbopol® 940, and Carbopol® 941, Carbopol® 71G, commercially available from Lubrizol. Examples of such polymers are described in U.S. Pat. Nos. 2,798,053 and 2,909,462, the entireties of which are incorporated herein by reference. Theoretical molecular weight ranges of Carbopol® products are in a range from 700,000 to 3 billion, theoretical estimation. For dosage forms as described herein, a gelling polymer (e.g., Carbopol®) can have a molecular weight and viscosity-increasing performance that will reduce or substantially inhibit an ability of an abuser to extract API from a combination of dosage form and a small volume of solvent, as described, while also being capable of being processed into a compressed dosage form.

A gelling polymer can also be characterized by viscosity of a solution prepared from the gelling polymer. Product information for commercially available Carbopol® polymers reports that viscosities of different Carbopol® polymers are as follows:

| Type of Carbomer | Viscosity specified (cP) |
| --- | --- |
| Carbomer Homopolymer Type A (compendial name for Carbopol 71G, Carbopol 971P and Carbopol 981) | 4,000-11,000 |
| Carbomer Homopolymer Type B (compendial name for Carbopol 934P, and Carbopol 934) | 25,000-45,000 |
| Carbomer Homopolymer Type C (compendial name for Carbopol 980) | 40,000-60,000 |

(Type A and Type B viscosities measured using a Brookfield RVT, 20 rpm, neutralized to pH 7.3-7.8, 0.5 weight percent mucilage, spindle #5.)

Another example of a type of preferred gelling polymer is the class of xanthan gum polymers, which includes natural polymers useful as hydrocolloids, and derived from fermentation of a carbohydrate. A molecular weight of a Xanthan gum may be approximately 1,000,000. Xanthan gum has been shown to provide particularly useful extraction resistance in a dosage form as described, and therefore may be preferred in dosage forms as described, especially if present in an amount of at least 2 or 3 weight percent based on a total weight of a dosage form.

Without limiting the scope of useful gelling polymers to any specific type or molecular weight, examples of useful gelling polymers, and useful respective molecular weights, are shown at Table below.

| Gelling Polymer | Weight Average Molecular Weight |
| --- | --- |
| Carbomer | 700,000 to 3 billion (estimated) |
| HPMC 2910 K types | 164,000-1,200,000 |
| HPMC 2910 E types | 20,000-746,000 |
| hydroxyethylcellulose | 90,000-1,300,000 |
| ethylcellulose | 75,000-215,000 |
| carboxymethylcellulose | 49,000-725,000 |
| sodium carboxymethylcellulose | 49,000-725,000 |
| povidone | 4,000-1,300,000 |
| copovidone | 47,000 |
| hydroxypropyl cellulose | 40,000-1,150,000 |
| xanthan gum | 1,000,000 |
| polyethylene oxide | Average molecular wt: 100,000-7,000,000 |

The dosage form may optionally include another abuse deterrent in the form of a wax, such as a wax/fat material as described in Applicant's co-pending United States patent application 2008/0311205, the entirety of which is incorporated herein by reference. The wax can be a solid wax material that is present in the dosage form at a location that inhibits an abuser from crushing, grinding, or otherwise forming the dosage form into a ground powder that might be abused by a nasal insufflation mode, or from which active pharmaceutical agent can be easily accessed and removed such as by dissolution or extraction using a solvent.

The wax may be present in the dosage form at a location and in an amount to also not interfere with desired uptake of the active pharmaceutical ingredient by a patient upon oral ingestion, in an immediate release dosage form. An exemplary location is at a core of a core-shell particle, especially a core that also contains gelling polymer and that either may or may not contain active pharmaceutical ingredient. Wax located at a core of a particle (e.g., a core-shell particle) that also includes active pharmaceutical ingredient (e.g., at a layer covering the core, or within the core) will become mixed with the active pharmaceutical ingredient upon crushing or grinding, etc., of the particle. As discussed previously, the dosage form may also include core shell particles that do not contain an API. Wax that is located at a core of such a particle (e.g., a core-shell particle) that does not contain API will also become mixed with the API (e.g., API present in API-containing core shell particles that are also present in the dosage form) upon crushing, grinding, etc., of the dosage form. When the wax is mixed with the active pharmaceutical ingredient, the active ingredient is inhibited or prevented from becoming thereafter dissolved in a solvent such as water, or otherwise efficiently accessed by an abuser.

A core (uncoated) of a core-shell particle can contain any useful amount of wax, up to and including 100 percent wax, e.g., from 0.1 to 85 weight percent wax based on a total weight of the core, such as from 15 to 60 or 25 to 50 weight percent wax based on total weight core. More generally, a useful amount of wax in a dosage form (e.g., with the wax located in the coated particle, e.g., in the core) may be in a range from 0.05 to 15 weight percent wax based on total weight of a dosage form, e.g., from 0.1 to 10 or from 2 to 5 weight percent wax based on total weight of the dosage form.

The wax may be a wax (e.g., fat) material that is generally hydrophobic and that may be either solid or liquid at room temperature, preferably solid at room temperature (25 degrees Celsius). Generally useful fats include those hydrophobic materials that are fatty acid-based compounds generally having a hydrophilic/lipophilic balance (HLB) of 6 or less, more preferably 4 or less, and most preferably 2 or less. A fat can have any melting temperature, with preferred fats being solid at room temperature and having a melting point that is at least 30 degrees Celsius, e.g., at least 40 degrees Celsius, e.g., at least 50 degrees Celsius. Useful fats include fatty acids and fatty esters that may be substituted or unsubstituted, saturated or unsaturated, and that have a chain length of at least 10, 12, or 14 carbons. The esters may include a fatty acid group bound to any of an alcohol, glycol, or glycerol. With regard to glycercols, for example, mono-, di-, and tri-fatty substituted glycerols can be useful as well as mixtures thereof.

Suitable wax ingredients include fatty acid esters, glycerol fatty acid esters, fatty glyceride derivatives, waxes, and fatty alcohols such as, for example, glycerol behenate (a.k.a. glyceryl behenate, glycerin behenate, glycerol docosanoate) (e.g., COMPRITOL®), glycerol palmitostearate (PRECIROL®), glycerol monostearate, stearoyl macroglycerides (GELUCIRE® 50/13). Other waxes more generally include insect and animal waxes, vegetable waxes, mineral waxes, petroleum waxes, and synthetic waxes; particularly examples include beeswax, carnauba wax, candelilla wax, montan wax, ouricury wax, rice-bran wax, jojoba wax, microcrystalline wax, cetyl ester wax, cetyl alcohol, anionic emulsifying wax, nonionic emulsifying wax and paraffin wax.

The dosage form may optionally include another abuse deterrent in the form of a filler or binder material provided in a manner to compromising abuse practices wherein an abuser crushes, grinds, or otherwise forms the dosage form into a ground powder that might be abused by a nasal insufflation mode, or from which active pharmaceutical agent can be easily accessed and removed such as by dissolution or extraction using a solvent.

The binder or filler may be present in the dosage form at a location and in an amount to also not interfere with desired uptake of the active pharmaceutical ingredient by a patient upon oral ingestion, in an immediate release dosage form. An exemplary location is at a core of a core-shell particle. Suitable filler or binder located at a core of a particle (e.g., a core-shell particle) that also includes active pharmaceutical ingredient (e.g., at a layer covering the core, or within the core) will become mixed with the active pharmaceutical ingredient upon crushing or grinding, etc., of the particle. As discussed previously, the dosage form may also include core shell particles that do not contain an API. Filler or Binder that is located at a core of such a particle (e.g., a core-shell particle) that does not contain API will also become mixed with the API (e.g., API present in API-containing core shell particles that are also present in the dosage form) upon crushing, grinding, etc., of the dosage form. When a filler or binder is mixed with the active pharmaceutical ingredient, the active pharmaceutical ingredient is inhibited or prevented from becoming thereafter dissolved in a solvent such as water or otherwise efficiently accessed by an abuser.

When present within a core or particle of a dosage form, e.g., at a core of a core-shell particle, filler or binder may be present in any useful amount, such as from 0 up to and including 100 percent filler or binder (singly or in combination) in a core of a core-shell particle, e.g., from 10 to 95 weight percent filler or binder (singly or in combination) based on total weight of the core, such as from 40 to 85 or 50 to 75 weight percent based on total weight core. Examples of cores that contain high levels of filler include spherical particles that contain 100 percent sugar, and spherical particles that contain 100 percent microcrystalline cellulose. Inert spherical filler products such as these, having useful particle sizes, are commercially available under the trade name Celphere®, and under the trade name Suglets® (sugar spheres, also containing starch), including as follows: CELPHERE SCP-100 (Particle size (μm) 75-212); CELPHERE SCP-102 (Particle size (μm) 106-212); CELPHERE SCP-203 (Particle size (μm) 150-300); CELPHERE SCP-305 (Particle size (μm) 300-500); CELPHERE SCP-507 (Particle size (μm) 500-710); CELPHERE SCP-708 (Particle size (μm) 710-850). The particle sizes of these can be considered to be useful for any core as described herein, prepared of any single filler, gelling polymer, binder, any combination thereof, or any single or combination of materials combined with API.

Another optional abuse deterrent feature that can be included in a dosage form as described is a film layer or coating as part of a core-shell particle that is located over and surrounds an API. The film layer may also be present as a layer or coating on core shell particles which do not contain an API or an API layer. The film layer can be any film layer capable of being applied as a film layer to core-shell particles, to surround API, or to core-shell particles that do not contain an API or an API layer.

The film layer may be prepared from, and will include any pharmaceutically acceptable film forming polymer material, such as one or more of a binder (e.g. as described herein, such as hydroxypropyl cellulose, poly(methyl methacrylates), ethyl cellulose, hydroxypropyl methyl cellulose, hydroxyl methyl cellulose, polyvinyl alcohol, and the like), a solvent-resistant layer, and a pH-sensitive layer (also sometimes referred to as a reverse enteric material or layer), e.g., Eudragit® E 100. The film layer may include any one of these materials alone (e.g., a film layer may include 100 percent of a single one of these types of materials), or a film layer may include a combination of two or more of these types of materials.

A solvent-resistant layer is a film layer that retards or prevent release of a drug in a solvent (e.g., one or more of water, ethanol, and methanol) while still allowing the drug to release normally in a gastrointestinal tract when ingested as an immediate release oral dosage form. This type of abuse deterrent feature, e.g., solvent-resistant film, can inhibit access to an API of a dosage form by preventing or impeding an abuser from dissolving an intact or powdered dosage form in a solvent type that is often used by an abuser (e.g., water, ethanol, methanol). At the same time, the solvent-resistant film can dissolve in a human gastrointestinal tract with sufficient rapidity to allow for an immediate release profile. As an abuse deterrent feature this type of solvent-resistant film covers and encloses API of a core-shell particle and acts as a film barrier or retardant to prevent or retard access to the API by use of solvent.

A solvent-resistant film is one that does not readily or immediately dissolve in a small volume of a solvent of the type often used by an abuser to dissolve an API, such as any one of water or a $C_1$-$C_4$ alcohol such as ethanol or methanol. A "small volume" refers to an amount of such a solvent that can contain an amount of dissolved API that is sufficiently concentrated to be useful to an abuser to realize the intended biological effect of the drug abuse, and that is also capable of being administered for abuse of the API, e.g., a volume that can contain an amount (concentration) of API that is effective to achieve a desired "high" if administered by injection or nasal insufflation, the volume also being sufficiently small to allow the volume to be administered by injection or nasal insufflation. For a dosage form to be useful for abuse as such, an API in the dosage form must be capable of being accessed and dissolved at sufficient concentration by an abuser without undue complication, into a "small volume" of solvent, which is a volume that can be administered by injection or by nasal insufflation. Generally, a "small volume" of solvent means 50 milliliters or less, or 20 milliliters or less, or 10 milliliters or less, or 5 milliliters or less (volumes which could be injected or used for nasal insufflation).

A solvent-resistant film layer can be a film placed on a core-shell particle that is difficult to dissolve in a "small volume" of water or a $C_1$-$C_4$ alcohol such as ethanol or methanol, e.g., that does not immediately dissolve in one or more of water or any one of a $C_1$-$C_4$ alcohol such as methanol or ethanol. The solvent-resistant film thereby retards or prevents an abuser from accessing an API portion of a core-shell particle if the core-shell particle is placed in one of these solvents. The solvent-resistant film need not be completely or substantially insoluble in any one of these solvents, or in all of the solvents, and it must be capable of allowing the API to be accessed with sufficient rapidity, in a gastrointestinal tract, for the dosage form to be useful as an immediate release dosage form.

A particular example of a solvent-resistant film is a film that exhibits solubility properties that depend on the pH of a solvent. An example of a solvent-resistant film may be a film that is substantially or completely insoluble at a pH that is greater than a pH condition of a human stomach, and that is sufficiently soluble at a pH condition of a stomach (and gastrointestinal tract) to allow the film to dissolve and release API with sufficient rapidity that the dosage form can be useful as an immediate release oral dosage form. A pH-sensitive layer is a type of solvent-resistant film, and can be disposed in a dosage form to surround an active pharmaceutical ingredient and inhibit or prevent access to and dissolution of the active pharmaceutical ingredient in a solvent outside of a stomach (e.g., at a neutral pH environment), while still allowing the active pharmaceutical ingredient to be efficiently released from an immediate release dosage form at a lower pH environment of a user's stomach. This type of abuse deterrent feature can prevent or significantly impede an abuser's access to an active pharmaceutical agent of a dosage form (e.g., at the core of a core-shell particle or in a layer disposed on the core, or in both the core and the layer disposed on the core) by use of a solvent that is outside of a stomach and that does not have a relatively acidic pH, such as water or a $C_1$-$C_4$ alcohol such as ethanol, methanol, etc., or a mixture thereof, having a pH that is higher than a pH found in a human stomach, for example a pH greater than 4; greater than 5; or greater than 5.5; or greater than 6.

A pH-sensitive layer may be useful as a solvent-resistant film, placed in a dosage form as a layer of a core-shell particle to surround, cover, or enclose a portion of the core-shell particle that contains active pharmaceutical ingredient. For example in a core-shell particle, an active pharmaceutical ingredient may be located as desired at a core or at a layer outside of an uncoated or coated core; a solvent-resistant film in the form of a pH-sensitive layer may be disposed as a separate layer surrounding or covering the portion of the core-shell particle that contains the active pharmaceutical ingredient. The pH-sensitive layer may be in direct contact with (adjacent to) a core or a layer that includes active pharmaceutical ingredient; alternately a core-shell particle may include one or more intermediate layers between a pH-sensitive layer and a core or layer that includes active pharmaceutical ingredient. In addition, a pH-sensitive layer may be included in the dosage form as a layer of a core-shell particle that does not contain either an API layer or any API.

A useful pH-sensitive layer may include a polymer or other material that can be placed as a layer of a particle as described herein, such as to cover a more inner layer or core that contains active pharmaceutical ingredient, to form a pH-sensitive film surrounding or covering active pharmaceutical ingredient. The pH-sensitive film can be solubilized by exposure to a liquid that exhibits a pH that may be present in a stomach of a user of the dosage form, such as a pH below 6 or below 5.5. To function as an abuse deterrent feature, i.e., to inhibit or prevent efficient access to the active pharmaceutical ingredient by exposing the dosage form (optionally ground or powdered) to an easily-available solvent, the pH-sensitive layer can contain polymer that is not easily or substantially soluble at a pH that is higher than a pH found in a human stomach, e.g., a pH greater than 6; by being insoluble at a pH greater than 6, the pH-sensitive polymer will not dissolve in many solvents easily available and commonly used by an abuser to extract a water-soluble drug from a dosage form such as water, ethanol, methanol, etc.

Examples of pH-sensitive polymer useful in a pH-sensitive layer include the class of reverse enteric polymers that contain cationic-functional groups and that exhibit pH-dependent solubility as described herein. Examples include polymers that contain basic functional groups such as amino groups, and that exhibit solubility at pH conditions found in a (human) stomach but not at relatively higher pH conditions, e.g., not above a pH of 4, 5, or 5.5, or not above a pH of 6. More specific examples of such pH-sensitive polymers include copolymers of dimethyl aminoethyl methacrylates, and neutral methacrylic acid esters; e.g., dimethyl aminoethyl methacrylate, butyl methacrylates, and methyl methacrylates, such as at a ratio of 2:1:1. Examples of such polymers are commercially available under the trade name Eudragit® E-100, Eudragit® E PO, Eudragit® E 12.5, and similar amino-functional pH-sensitive polymers. A preferred pH-sensitive polymer is the polymer Eudragit E100, but any polymer that is sufficiently hydrophilic at a low pH and hydrophobic at a higher pH to exhibit pH-dependent solubility as described, may also be effective if otherwise acceptable for use in a pharmaceutical dosage form, for example as a non-toxic ingredient of an oral dosage form. Reverse enteric compositions are also described in EP 1694724 B1, titled "pH Sensitive Polymer and Process for Preparation Thereof."

When present as a coating of a particle that contains active pharmaceutical ingredient, a solvent-resistant film layer may be present at any amount useful as an abuse deterrent feature, such as in a range from 0.1 to 90 weight percent of a total weight of a core-shell particle, e.g., from 3 to 50 or 4 to 40 weight percent solvent-resistant polymer per total weight core-shell particle. More generally, a useful amount solvent-resistant film layer or polymer in a dosage form may be in a range from 1 to 50 weight percent solvent-resistant film layer or polymer based on a total weight of a dosage form, e.g., from 2 to 30 or from 3 to 15 weight percent solvent-resistant polymer based on total weight dosage form. Similarly, when present as a coating of a particle that does not contain an API, a solvent-resistant film layer may be present at any amount useful as an abuse deterrent feature, for example in the same numerical ranges as are disclosed above for coating particles that contain API.

A dosage form as presently described can also preferably include a disintegrant, which functions to cause the dosage form to expand and break up during use, e.g., at conditions of a human stomach, to allow active pharmaceutical ingredient of the dosage form to be released in a manner to achieve an immediate release profile. Disintegrants are known ingredients of pharmaceutical dosage forms, with various examples being known and commercially available. Examples of disintegrants include compositions of or containing sodium starch glycolate, starch (e.g., maize starch, potato starch, rice starch, tapioca starch, wheat starch, corn starch and pregelatinized starch), croscarmellose sodium, crospovidone (crosslinked polyvinyl N-pyrrolidone or PVP) (polyplasdone XL-10), sodium starch glycolate (EXPLOTAB® or PRIMOJEL®), any combination of two or more of the foregoing, and other pharmaceutically acceptable materials formed into particles having a particle size, density, etc., to allow processing of the disintegrant into a useful immediate release dosage form.

The disintegrant can be present in an immediate release dosage form at any location that allows the disintegrant to function as desired, to expand within the intact dosage form, upon ingestion, to cause the ingested dosage form to break apart and allow for desired immediate release of active pharmaceutical ingredient from the dosage form, in a stomach. One useful location for a disintegrant can be as a component of an excipient used to contain core-shell particles that contain active pharmaceutical ingredient, as described herein, in a dosage form such as a compressed tablet or capsule.

When included as an excipient of a dosage form, disintegrant may be present in an amount useful to achieve immediate release of an API of a dosage form. Examples of useful amounts of disintegrant in an immediate release dosage form as described herein may be in a range from 0.5 to 50 weight percent disintegrant based on a total weight of the dosage form, e.g., from 1 to 30 weight percent disintegrant based on total weight of the dosage form. The amount of disintegrant in a matrix of a dosage form can be consistent with these amounts, e.g., disintegrant can be included in a matrix (e.g., total of a dosage form that is other than the coated particles or API) of a dosage form in an amount in a range from 0.5 to 50 weight percent disintegrant based on a total weight of the matrix, e.g., from 1 to 30 weight percent disintegrant based on total weight matrix.

A dosage form as described can also include any of various known and conventional pharmaceutical excipients that may be useful to achieve desired processing and performance properties of an immediate release dosage form. These excipients include fillers, binders, lubricants, glidants, coloring agents, pH-adjusters, etc., and can be included in core-shell particles or in a matrix (e.g., compressed matrix) of a tablet or capsule. A more detailed description of pharmaceutical excipients that may also be included in the tablets of the present invention can be found in The Handbook of Pharmaceutical Excipients, 5th ed. (2006).

A pH-adjuster can be included in an immediate release dosage form as described, for example at a location to affect pH at a specific location of the dosage form that is only a portion of a total dosage form. As an example, a pH-adjuster in the form of a base may be included at a location of a gelling polymer that contains acid functionalities, to neutralize the acid functionalities. Suitable agents that can act as a pH-adjuster are well know in the art and include for example, phosphate buffering agents such as, disodium hydrogen phosphate, sodium dihydrogen phosphate and the equivalent potassium salts; carbonate or bicarbonate salts, such as sodium bicarbonate, sodium carbonate, potassium bicarbonate, potassium carbonate, magnesium carbonate and calcium carbonate; hydroxide bases such as, sodium hydroxide, potassium hydroxide, ammonium hydroxide; and amine bases such as, triethanolamine, tromethamine, aminomethyl propanol, and tetrahydroxypropyl ethylenediamine.

The amount of pH-adjuster included at the location of the gelling polymer can be an amount effective to neutralize the acid functionalities of the gelling polymer at that location. More specifically, a component of a dosage form as described that includes an acid-functional gelling polymer such as a carbopol may include a base in an amount and location to neutralize the acid functionalities of that polymer. The pH-adjuster can be located at a location effective to cause such neutralization, e.g., at the location of the dosage form that contains the acid-functional gelling polymer, for example at a core of a core-shell particle or as part of an excipient that includes acid-functional gelling polymer and that functions to bind particles together as a dosage form.

Examples of fillers that may be useful in an immediate release dosage form as described include lactose, starch, dextrose, sucrose, fructose, maltose, mannitol, sorbitol, kaolin, microcrystalline cellulose, powdered cellulose, calcium sulfate, calcium phosphate, dicalcium phosphate, lactitol or any combination of the foregoing. As compared to non-filler ingredients such as gelling polymers, a filler will have a molecular weight that does not result in a substantial viscosity increase or formation of a gel as described herein for a gelling polymer, if combined with a solvent such as water.

A filler may be present in any portion of a dosage form as described, including a core-shell particle; the filler may be present in a core, in a layer containing an active pharmaceutical ingredient that is disposed on the core, in a solvent resistant film, in the matrix, or in two or more of these portions of the dosage form. The filler may be present at any one or more of these portions of a dosage form in an amount to provide desired processing or functional properties of a portion of the dosage form and of the entire dosage form. The amount of total filler in a dosage form can also be as desired to provide desired functionality, including an immediate release profile, for example in an amount in a range from 0 to 80 weight percent filler based upon the total weight of the dosage form, e.g. from 5 to 50 percent filler based on total weight dosage form.

Examples of binders that may be included in a dosage form as described include polymeric material such as alginic acid, sodium carboxymethylcellulose, microcrystalline cellulose, dextrin, ethylcellulose, gelatin, starch, pregelatinized starch, polyvinyl alcohol, polyethylene oxide, polyvinylpyrrolidone, polyacrylamides, polyvinyloxoazolidone, polyvinylalcohols, methylcellulose, hydroxypropyl cellulose, hydroxymethyl cellulose and any combination of two or more of these. A binder may be a water soluble material; as compared to non-binder ingredients such as a gelling polymer, a binder is of a molecular weight that does not result in formation of a gel or a highly viscous composition upon combining with a small volume of water. A binder can exhibit a relatively low molecular weight as compared to a gelling polymer, and a relatively lower viscosity (e.g., when measured in a 2% aqueous solution). Polymer useful as a binder may typically have a molecular weight of less than 50,000, e.g., less than 30,000, or less than 10,000.

A binder may be present in any portion of a dosage form as described, including a core or a film or coating of a core-shell particle, or as part of an excipient to contain or bind core-shells particles in a dosage form. Filler may be included in a core of a core-shell particle in combination with active pharmaceutical ingredient, gelling polymer or both; as part of an active pharmaceutical layer located over a core or another layer of a core-shell particle; as part of a solvent-resistant film; or within an excipient useful to bind particles into a dosage form. A binder may be present at any one or more of these portions of an immediate release dosage form as described, in an amount to provide desired processing or functional properties in each portion of the dosage form and of the overall dosage form. The amount of total binder in a dosage form can also be as desired to provide desired functionality, including immediate release functionality. For example a binder may be provided in an amount in a range from 0.1 to 10 weight percent binder based on a total weight of a dosage form, e.g., from 0.5 to 7 weight percent binder based on total weight dosage form. According to some embodiments, the binder may be provided in amounts ranging from 0.1 to 25, or 0.1 to 40 weight percent based on a total weight of a dosage form.

Examples of lubricants include inorganic materials such as talc (a hydrated magnesium silicate; polymers, such as, PEG 4000; fatty acids, such as stearic acid; fatty acid esters, such as glyceride esters (e.g., glyceryl monostearate, glyceryl tribehenate, and glyceryl dibehenate); sugar esters (e.g., sorbitan monostearate and sucrose monopalmitate); glyceryl dibehenate (Compritol® 888 ATO); and metal salts of fatty acids (e.g., magnesium stearate, calcium stearate, and zinc stearate). Accordingly, commonly used lubricants include talc, glyceryl monostearates, calcium stearate, magnesium stearate, stearic acid, glyceryl behenate, polyethylene glycol, poloxamer and combinations of the foregoing. Lubricant may be included in an immediate release dosage form as described, in any useful amount, such as an amount in a range from 0.1 to 10 weight percent lubricant based on a total weight of a dosage form, e.g., from 0.5 to 7 weight percent lubricant based on total weight dosage form.

Examples of glidants include colloidal silicon dioxide, untreated fumed silica (e.g., as available under the trade name Cab-O-Sil®), and crystalline or fused quartz. Glidant may be included in an immediate release dosage form as described, in any useful amount.

Examples of coloring agents include FD&C-type dyes and lakes, fruit and vegetable extracts, titanium dioxide, iron oxides and mixtures thereof. A coloring agent may be incorporated into a dosage form by blending (e.g., co-milling and blending) the coloring agent with any other ingredient. Alternately, coloring agent may be applied to an outer surface of a dosage form.

Any active pharmaceutical ingredient alone or in combination can be included in an immediate release dosage form as described herein. With abuse deterrent features as described herein, some being operative based on specific structural or compositional features of a core-shell particle, APIs that can be particularly useful can be those types of active pharmaceutical ingredients that can be subject to abuse, addiction, overdosing, or two or more of these; such APIs can be located in the dosage form at a location to cause the API to be subject to abuse deterrent features of the core-shell particle, e.g., at a core or inner layer of a core-shell particle.

Drugs commonly susceptible to abuse include sedative-hypnotics, stimulants (e.g., central nervous system ((CNS) stimulants), anxiolytics, antipsychotics, dissociative anesthetics, and narcotic analgesics including but not limited to drugs that can cause psychological or physical dependence on the drug. An API can include any therapeutically acceptable drug salt, drug derivative, drug analog, drug homologue, or polymorph of an active pharmaceutical ingredient.

Sedative hypnotics include, for example, barbiturates, for example phenobarbital, methobarbital, amobarbital, pentobarbital, butalbital and secobarbital and pharmaceutically acceptable salts thereof; benzodiazepines, for example diazepam, chlorodiazepoxide, lorazepam, triazolam, temazepam, alprazolam and flurazepam and pharmaceutically acceptable salts thereof; phenothiazines, such as for example, alimemazine, chlorpromazine, thioridazine, and pharmaceutically acceptable salts thereof, and sleep medications, such as for example, zolpidem, zaleplon, and eszopiclone and pharmaceutically acceptable salts thereof. Anxiolytics include, for example, benzodiazepines, for example diazepam, chlordiazepoxide, estazolam, lorazepam, triazolam, alprazolam, clonazepam and flurazepam and pharmaceutically acceptable salts thereof. CNS stimulants include, for example, amphetamines, such as for example, dextroamphetamine, levoamphetamine (benzadrine), methamphetamine (methadrine), pseudoephedrine, and Adderall (amphetamine mixed salts) and pharmaceutically acceptable salts thereof, and non-amphetamine psychostimulants such as methylphenidate, modafinil and armodafinil and pharmaceutically acceptable salts thereof. Narcotic analgesics include opioids such as, for example, buprenorphine, butorphanol, cebranopadol, codeine, dihydrocodeine, dihydromorphine, hydrocodone, hydromorphone, morphine, oxycodone, oxymorphone, methadone, fentanyl, meperidine, tramadol, propoxyphene, and pharmaceutically acceptable salts thereof. Antipsychotic agents can include, for example, phenothiazines as listed above, butyrophenones, such as, for example, droperidol and haloperidol, dibenzoxazepines such as loxapine, and atypical antipsychotic agents such as aripiprazole, clozapine, olanzapine, quetiapine, risperidone ziprasidone, paliperidone and remoxipride.

Other specific drugs which may be susceptible to abuse include for example, muscle relaxants such as for example cyclobenzaprine and pharmaceutically acceptable salts thereof, cannabinols (e.g., $\Delta^1$-cannabidiol. $\Delta^2$-cannabidiol, $\Delta^3$-cannabidiol, $\Delta^{3,7}$-cannabidiol, $\Delta^4$-cannabidiol, $\Delta^5$-cannabidiol, and $\Delta^6$-cannabidiol); cannabinoids, such as dronabinol, delta-9-tetrahydrocannabinol (THC), cannabidiol (CBD), nabilone, dexanabinol, ajulemic acid, cannabinor, rimonabant and taranabant, and pharmaceutically acceptable salts thereof; and dissociative anesthetic agents such as ketamine and Esketamine (which are also known to demonstrate activity in the treatment of depression), and pharmaceutically acceptable salts thereof.

The API's described herein as suitable for formulation according to the invention are also intended to include such API's wherein the molecular structures include isotopes of carbon, hydrogen and nitrogen atoms occurring on those structures. Isotopes include those atoms having the same atomic number but different mass numbers. For example, isotopes of hydrogen include deuterium. Isotopes of carbon include C-13. Isotopes of nitrogen include N-15.

Accordingly, within the chemical structure of any API taught in this application as suitable for the formulations disclosed herein:

any hydrogen atom or group of hydrogen atoms, could suitably be replaced by an isotope of hydrogen, i.e., deuterium;

any carbon atom or group of carbon atoms, could suitably be replaced by an isotope of carbon, i.e., $^{13}C$; and any nitrogen atom or group of nitrogen atoms, could suitably be replaced by an isotope of nitrogen, i.e., $^{15}N$.

As used herein, an API that is termed "isotopically-enriched" means that the abundance of deuterium, $^{13}C$, or $^{15}N$ at any relevant site of the compound is substantially more than the abundance of deuterium, $^{13}C$, or $^{15}N$ naturally occurring at that site in an amount of the compound. A relevant site in a compound as used above is a site which would be designated as "H" or "C" or "N" in a chemical structure representation of the compound when not enriched. The expression, "Naturally occurring," as used above refers to the abundance of the particular atom which would be present at a relevant site in a compound if the compound was prepared without any affirmative synthesis step to enrich the abundance of a different isotope. Thus, for example in a "deuterium-enriched" compound, the abundance of deuterium at any relevant site in the chemical structure of the API can range from an amount that is substantially more than the natural abundance of deuterium (about 0.0115%) all the way up to 100%, for example, from about 1% to about 100%, or from about 10% to about 100%, or from about 50% to about 100%, or from about 90% to about 100%.

Similarly, for a "$^{13}C$-enriched" compound, the abundance of $^{13}C$ at any relevant site in the chemical structure of the API can range from an amount that is substantially more than the natural abundance of $^{13}C$ (about 1.109%) all the way up to 100%, for example, from about 5% to about 100%, or from about 10% to about 100%, or from about 50% to about 100%, or from about 90% to about 100%. Similarly for a "$^{15}N$-enriched" compound, the abundance of $^{15}N$ at any relevant site in the chemical structure of the API can range from an amount that is substantially more than the natural abundance of $^{15}N$ (about 0.364%) all the way up to 100%, for example, from about 1% to about 100%, or from about 10% to about 100%, or from about 50% to about 100%, or from about 90% to about 100%.

Isotopically-enriched compounds can generally be prepared by conventional techniques known to those skilled in the art. Such isotopically-enriched compounds can also be prepared by adapting conventional processes as described in the scientific literature for synthesis of API's disclosed herein as suitable for formulation according to the invention, and using an appropriate isotopically-substituted reagent (or reagents) in place of the corresponding non isotopically-substituted reagent(s) employed in the conventional synthesis of the non isotopically-enriched compounds. Examples of ways to obtain a deuterium-enriched compound include exchanging hydrogen with deuterium or synthesizing the compound with deuterium-enriched starting materials.

The amount of active pharmaceutical ingredient included in an immediate release dosage form can be any useful amount, as is known and as may be found in relevant literature such as Goodman & Gillman's, The Pharmacological Basis of Therapeutics, 9th ed. pages 219-222, 361-396, 521-535 1996. For example, typical therapeutic amounts of oxycodone range 5 mg, 10 mg, or up to 400 mg, for the hydrochloride salt. Often, when processed into a suitable immediate release dosage form, the active pharmaceutical ingredient can be present in such dosage form in an amount normally prescribed, typically 0.5 to 25 percent on a dry weight basis, based on the total weight of the dosage form. With respect to narcotic analgesics such as opioids in a single unit dosage form, such as at a level from about 1 to about 500 mg, or from about 1 to about 250 mg, or from about 1 to about 100 mg; for example, 2.5, 5, 7.5, 10, 15, 20, or 30, milligram (mg) per dosage form unit. In other embodiments, a dosage form contains any appropriate amount of an API to provide a therapeutic effect.

The present invention is also directed to methods of treatment, comprising orally administering an effective amount of the herein described immediate release abuse deterrent dosage form. For example, provided herein is a method of treating or preventing pain or discomfort in a subject in need thereof by administering an effective amount of the herein described immediate release abuse deterrent dosage form containing an API that is a narcotic analgesic drug such as an opioid drug.

Also provided herein is a method for treating sleep disorders in a subject in need thereof by administering an effective amount of the herein described immediate release abuse deterrent dosage form containing an API that is a sedative hypnotic drug such as a barbiturate.

Also provided herein is a method for treating anxiety in a subject in need thereof by administering an effective amount of the herein described immediate release abuse deterrent dosage form containing an API that is an anxiolytic drug e.g., a benzodiazepine.

Also provided herein is a method for treating psychoses in a subject in need thereof by administering an effective amount of the herein described immediate release abuse deterrent dosage form containing an API that is an antipsychotic drug such as quetiapine.

Also provided herein is a method for treating depression in a subject in need thereof by administering an effective amount of the herein described immediate release abuse deterrent dosage form containing an API that demonstrates antidepressant activity, such as ketamine or Esketamine.

An "effective amount" of when used in connection with composition described herein is an amount sufficient to produce a therapeutic result in a subject in need thereof. For example a therapeutic result can include, but is not limited to treating or preventing pain, sleep disorders, anxiety or psychotic symptomology by a subject.

A dosage form as described can optionally include one or more additional APIs of a type that is not commonly susceptible to abuse. These additional APIs may be any suitable or desired API, such as those in the class of non-steroidal analgesic drugs. The expression "non-steroidal analgesic drugs" as used herein refers to drugs that include those commonly referred to as non-steroidal anti-inflammatory drugs, or "NSAIDS," and acetaminophen, which is non-steroidal, but does not act via an inflammation mechanism. Accordingly, the term "non-steroidal analgesic drugs" would include acetaminophen, and also include NSAIDS such as aspirin, ibuprofen, and naproxen. The dosage form also exhibits immediate release properties with respect to these not-commonly-subject-to-abuse APIs. And these APIs can be present in the dosage form at any useful level, typically 0.5 to 25, e.g., 1 to 10 weight percent of the API on a dry weight basis, based on a total weight of the dosage form, e.g., at a level of or between 5, 25, 50, 75, 100, 125, 150, 175, 200, 300, 325, 500, 750 or up to or exceeding 1000 milligram (mg) per dosage form unit. In other embodiments, a dosage form contains an appropriate amount of an API to provide a therapeutic effect.

An immediate release dosage form as described can include one or more of the described abuse deterrent features, alone or in combination; e.g., one or more of: gelling polymer as part of a core-shell particle (e.g., at a core of the core-shell particle); wax as part of a core-shell particle (e.g., at a core of the core-shell particle); binder or filler as part of a core-shell particle (e.g., at a core of the core-shell particle); a film layer that may optionally be a solvent-resistant film (e.g., pH-sensitive film) as part of a core-shell layer; or gelling polymer as a component of an excipient or binder used to hold core-shell particles together as part of in an immediate release dosage form. With these abuse deterrent features, other types of known abuse deterrent features may not be necessary and may be specifically excluded from an immediate release dosage form as described. Certain embodiments of the described dosage forms can specifically exclude other types of abuse deterrents.

In specific, some dosage forms include nasal irritant to discourage or prevent abuse by nasal insufflation. The nasal irritant can be a mucous membrane irritant or nasal passageway irritant that, if inhaled through a nasal passageway when contained in a ground or powdered dosage form, can induce pain or irritation of the abuser's nasal passageway tissue. Examples include surfactants such as sodium lauryl sulfate, poloxamer, sorbitan monoesters, and glyceryl monooleates. Certain particular embodiments of dosage forms of the present description do not require, and can specifically exclude, nasal irritant agents such as those described above.

Alternately, dosage forms can include an emetic agent, to cause vomiting. Certain particular embodiments of dosage forms of the present description do not require and can specifically exclude an emetic agent.

Alternately, some dosage forms include an effervescent agent that acts as a deterrent to abuse by nasal insufflation. The effervescent includes an acidic component and a basic component that release a gas such as oxygen or carbon dioxide when combined in the presence of an aqueous media, such as upon nasal insufflation. See, e.g., patent publication WO 2013/077851, the entirety of which is incorporated herein by reference. The acid source may be, for example, citric acid, tartaric acid, malic acid, maleic acid, lactic acid, glycolic acid, ascorbic acid, fumaric acid, adipic acid, succinic acid, salts thereof, and combinations thereof. The base may be, for example, a carbonate or bicarbonate. Dosage forms of the present description do not require, and can specifically exclude, an effervescent agent in the form of an acid and a base that can combine to a gas such as oxygen or carbon dioxide.

Still other dosage forms include a biologically active chemical compound that functions as an antagonist to an active pharmaceutical ingredient. An antagonist may prevent the potential abuse of a dosage form in a manner, including the method of consuming multiple or several or more dosage form units at once. Antagonist agents are compounds that block or negate the effect of an active pharmaceutical ingredient, and are available and known for various classes of drugs including opioids and other pharmaceutical agents. Examples of antagonist agents for opioids include compounds such as naltrexone, naloxone, nalmefene, cyclazacine, levallorphan. Specific examples of antagonist agents and methods for preparing antagonist agents for incorporation into a dosage form are provided in U.S. Pat. Nos. 7,682,633 and 7,658,939, which are incorporated herein by reference. According to the present description, an immediate release dosage form that includes an opioid and that includes one or more abuse deterrent feature as described herein (e.g., a gelling polymer, wax, solvent-resistant film, or a combination thereof), can be formulated to not contain and to specifically exclude an antagonist of an API that is also included in the dosage form, e.g., an opioid antagonist in a dosage form containing an opioid.

Referring to FIGS. 1A and 1B, a dosage form can include particles 10A that contain API. The particle (e.g., coated particle or "core-shell" particle) can include a core 12a (or "uncoated core"), which may be coated with one or more layers, films or coatings, e.g., 14a, 16a, or any additional layer or coating that is coated over, underneath, or intermediate to these. In FIGS. 1B and 1C, the layer designated 16a may be an API containing layer, and the layer designated as 14a may be a solvent resistant, e.g., a pH sensitive film layer. Particle 10A can contain one or more of the ingredients described herein, such as any one or more of API (especially an API that is susceptible to abuse), a gelling polymer, optional wax, optional solvent-resistant layer, as well as one or more additional layer or layers under, over, or intermediate to these layers or between either layer and the core. Each layer can be present in size or amount (e.g., thickness) that will result in a useful immediate release dosage form having one or more of the presently described abuse deterrent features. Other optional components of a core or layer of particle 10a can be filler, binder, other excipient, or solvent (not more than a residual amount, if any) such as water or ethanol for use in preparing the coated particle, and that is substantially removed after formation of the core, coating, or coated particle. Examples of the core 10A can include any amount of the different ingredients of: a gelling polymer (e.g. from 0 to 100 percent of a core), filler as described herein such as sugar (mannitol) or microcrystalline cellulose (e.g., from 0 to 100 percent of a core), binder (e.g., from 0 to 100 percent of a core), and wax (e.g., from 0 to 100 percent of a core).

While core-shell particles 10a are believed to be new and inventive, certain method steps useful to prepare these novel coated particles may be known. Available methods include certain methods and processing steps known to be useful for preparing particles and coated particles in the pharmaceutical arts. A core-shell particle 10a can be prepared by an initial step of mixing ingredients of core 12a with a solvent such as water or ethanol and forming the mixture into a spherical core particle by known methods. The particle may be dried and separated by size, and then one or more coating in the form of a continuous film or layer can be applied to the core, optionally successively to produce multiple layers surrounding the core. General processing to produce a multi-layer coated particle can include a series of steps such as compounding, mixing, granulation, wet milling, coating (by any method such as fluidized bed coating, spray coating, etc.), and one or more drying steps such as by use of a fluidized bed or other drying method. Intermittently between core-forming and coating steps, e.g., after a drying step, coated or uncoated particles can be sorted or separated based on size to produce a composition or a collection of particles having a desired size range and distribution. Accordingly, the coated granulate compositions according to the invention may be prepared by a process comprising:
(i) granulating a wax or a gelling polymer, or a mixture thereof, in the presence of a hydroalcoholic solution or suspension comprising a suitable binder, to form granules;
(ii) layering the granules formed in step (i) with a solution or suspension comprising an API; and
(iii) coating the layered granules formed in step (ii) with a solution or suspension comprising a film forming polymer material to form a coated layered granulate.
The process above may further comprise steps of milling and drying the granulate formed in step (i).

In instances wherein the core comprises a sugar sphere or a microcrystalline cellulose sphere, the steps of the process above would be modified as follows:
(i) providing a sugar sphere (or microcrystalline cellulose sphere);
(ii) layering the sugar sphere (or microcrystalline cellulose sphere) with a solution or suspension comprising an API; and
(iii) coating the layered sphere formed in step (ii) with a solution or suspension comprising a film forming polymer material to form a coated layered sphere.

Compressed tablets according to the invention may be prepared by a process comprising:
(i) combining the coated layered granulate (or the coated layered sphere) prepared according to either of the above processes with a second API (e.g., acetaminophen), a gelling polymer, and a disintegrant, and optionally, with at least one additional excipient selected from a filler, a colorant, and a pH adjusting agent, to form a first mixture and then blending the first mixture for a suitable time;
(ii) adding a lubricant to the blended mixture formed in step (i) to form a second mixture, and then blending the second mixture for a suitable time;
(iii) compressing the blended mixture formed in step (ii) to form compressed tablets.

A suitable time for the blending in step (i) may be, for example, from about 5 to about 90 minutes, or from about 10 to about 60 minutes, or from about 20 to about 40 minutes, or about 30 minutes. A suitable time for the blending in step (ii) may be, for example, from about 1 to about 30 minutes, or from about 5 to about 20 minutes, or about 10 minutes.

In certain embodiments as shown at FIGS. 1A, 1B, and 1C, an immediate release dosage form as described can include a core-shell particle 10A that includes a core 12A that contains only a minor amount of API or that contains an insubstantial amount of API. Core 12A may contain less than 5 weight percent, e.g., less than 1 or less than 0.5 weight percent active pharmaceutical ingredient based on a total weight of the core of the core-shell particle. Alternatively, core 12A may contain less than 5 weight percent of a total amount of pharmaceutical ingredient in a core-shell polymer, e.g., less than 5, less than 1, or less than 0.5 weight percent active pharmaceutical ingredient based on total weight of API in the core-shell particle. In these embodiments a major portion of API can be contained outside of core 12A, e.g., in an API layer 16a, which can contain at least 50, at least 75, or at least 90, or at least 95 weight percent of a total amount of the API in a core-shell polymer.

Core 12A can include binder, gelling polymer (e.g., HPMC), wax, or filler, optionally alone or in combination, each in an amount to allow the materials of the core to function as one or more abuse deterrent features as described herein. See the examples included herewith for examples of useful amounts and ranges of amounts of these ingredients.

Referring to FIG. 1A, core 12A contains gelling polymer, wax, binder, or filler, or any combination of these, and no API (meaning not more than an insignificant amount, such as less than 0.5 or less than 0.1 weight percent based on the weight of core 12A). As shown at FIGS. 1B and 1C, core 12A, not containing API, can be coated with a coating layer that contains API, e.g., an active pharmaceutical layer or API layer 16A. As shown at FIG. 1B, core-shell particle 10A includes core 12A, which does not contain any API, and API layer 16A, which contains an amount of API, such as a total amount of API (e.g., API commonly susceptible to abuse) to be contained in a dosage form prepared from particles 10A. API layer 16A can contain one or more ingredients as described herein useful to form API layer 16A as a layer over an outer surface of core 12A. (API in API layer 16A can be a type of API that is commonly susceptible to abuse, such as an opioid, and can account for all of or most of (e.g., at least 70, at least 80, at least 90, or at least 95 percent) the total amount of that type of API in the core-shell particles and in the dosage form; in this embodiment the core can contain less than 10, less than 5, or less than 1 percent of the total amount of API in the core-shell particles, and less than 10, 5, or 1 percent of the total amount of API in the dosage form.) Useful non-API ingredients in an API layer can include a binder along with the API. The API and binder can be carried in a solvent (e.g., water, ethanol, or both) and coated and dried to form a preferably continuous film layer on an outer surface of core 12A, i.e., API layer 16A. See the examples included herewith for examples of useful amounts and ranges of amounts of these ingredients.

A core-shell particle 10A can also optionally include a film layer, e.g., a solvent-resistant layer (e.g., a pH-sensitive layer) 14A as described herein.

In certain alternate embodiments a dosage form as described can include a core-shell particle 10B that includes a core 12B that does contain a useful amount of API, such as an amount of API useful in an immediate release dosage form having one or more abuse deterrent features as described herein, prepared to include particles 10B. See FIGS. 2A and 2B. According to such embodiments, core 12B of particle 10B can contain a gelling polymer, optional wax, optional binder or filler, and an amount of API.

Referring to FIG. 2A, core 12B contains gelling polymer, optional wax, optional binder, and API. Referring to FIG. 2B, core 12B, containing API, can optionally be coated with solvent-resistant layer (e.g., a pH-sensitive layer) 14B as described herein for use in an immediate release dosage form. Core 12B may also optionally be coated with a coating layer that contains API, e.g., an active pharmaceutical layer or API layer prior to application of the solvent-resistant layer. Accordingly, API containing core-shell particles as described herein may contain API of a type that is susceptible to abuse:

in an API layer surrounding the core and in a substantial amount in the core;
in an API layer surrounding the core and in an insubstantial amount in the core;
only in an API layer surrounding the core; or
only in the core.

In certain alternate embodiments, a dosage form as described can include a core-shell particle 10B, as depicted in FIG. 2B, that that does not contain an API layer, and does not contain any API. Referring to FIG. 2C, such a particle 10B, containing no API, may include core 12B containing gelling polymer, optional wax, and optional binder, which core 12B may optionally be coated with solvent-resistant layer (e.g., a pH-sensitive layer) 14B as described herein for use in an immediate release dosage form.

A coated particle 10a or 10b that includes API, and optionally, a coated particle 10B that does not include API, can be included in any of a variety of dosage forms, examples including a compressed tablet or compressed capsule, a suppository, capsule, caplet, pill, gel, soft gelatin capsule, etc. As one example, a dosage form 12 can be prepared as a compressed tablet or compressed capsule. Tablet or capsule 12 can contain core-shell particles 10 (e.g., 10A or 10B) distributed within a matrix 20, compressed to form the compressed tablet or compressed capsule 12. Core-shell particles 10A or 10B can be as described herein, generally or specifically, and can contain an amount of API suited to provide a desired dosage upon ingestion of tablet or capsule 12; e.g., matrix 20 does not include any substantial amount of API.

Matrix 20 can include ingredients useful in combination with the core-shell particles 10A, 10B, to produce an immediate release dosage form. Examples of useful excipients of an immediate release dosage form can include ingredients that allow the dosage form to break up or disintegrate upon ingestion and facilitate exposure to fluid in a stomach, such as a useful amount of disintegrant. Examples of such excipients for such a dosage form can also include one or more ingredients that act as an abuse deterrent feature, such as a gelling polymer as described herein. Other excipients can be useful for processing to form a compressed dosage form, and also may allow the compressed dosage form to function as an immediate release dosage form, with one or more abuse deterrent features.

The following non-limiting examples show various dosage forms as described herein. The described and exemplified dosage forms can be made from methods that include granulating, coating, and compressing steps as follows.

General Procedure
Granulation
1. Glyceryl behenate and hypromellose K100M are dry mixed in a high shear granulator. Hydroalcoholic solution of ethylcellulose is added. Alternatively the granulation can be produced through top spraying the hydroalcoholic solution in a fluid bed granulator. Optionally, a portion of the ethyl cellulose, for example from about 10 to about 50% by weight, or from about 10 to about 40% by weight, or from about 15 to about 30% by weight, is dry mixed with the Glyceryl behenate and hypromellose K100M prior to adding the hydroalcoholic solution containing the balance of the ethyl cellulose.
1. (alternative when API is included in the core) Glyceryl behenate and hypromellose K100M and API are dry mixed in a high shear granulator. Hydroalcoholic solution of ethylcellulose is added. Alternatively the granulation can be produced through top spraying the hydroalcoholic solution in a fluid bed granulator. Optionally, a portion of the ethyl cellulose, for example from about 10 to about 50% by weight, or from about 10 to about 40% by weight, or from about 15 to about 30% by weight, is dry mixed with the Glyceryl behenate and hypromellose K100M prior to adding the hydroalcoholic solution containing the balance of the ethyl cellulose.
2. The granules are then wet milled using a size reduction mill (Granumill) and then dried using a fluid bed, and optionally screened.

Layering
3. The polymer granules are then layered using Wurster fluid bed layering process with API (or alternatively, granulated using high shear granulation or top spray fluid bed granulation process).
3. (alternative when the coated granule will not contain API) The layering step is omitted and the coating of Step 4 below is applied to the granulate prepared in Step 1.

Coating
4. The layered granules of Step 3 (or alternatively, when the coated granule will not contain API, the granules prepared in Step 1) are then coated using a fluid bed coater equipped with a Wurster insert (bottom spray assembly) with ethanolic suspension of Eudragit E100 copolymer and magnesium stearate. Coated particles are then screened and blended.

Blending and Tablet Compression

The blending, compression and bottling process for hydrocodone and acetaminophen tablets manufactured using the coated intermediate is as follows:
1. The API-containing coated granules, APAP, crospovidone, Carbopol 71G, sodium bicarbonate, mannitol, optionally, coated granules containing no API, optionally, a glidant such as colloidal silicon dioxide, and optionally a desired colorant, are then added to the blender and mixed.
2. Magnesium stearate (and optionally colorant) is then added to the blender and mixed. The blend is compressed into tablets using a rotary tablet press.

Example 1: Preparation of Coated Granules

TABLE 1

| Components for granule formulation | |
|---|---|
| Component | % w/w |
| hypromellose | 60 |
| glyceryl behenate | 26 |
| ethyl cellulose | 14 |
| TOTAL | 100 |

Granules were manufactured in a high shear granulator, where hypromellose and glyceryl behenate were dry mixed for 3 minutes. Then, a 10% hydroalcoholic solution of ethylcellulose N10 was slowly added while maintaining the granulator impeller and chopper speed at pre-selected values that provide enough shear for granule formation and growth. Solution addition was continued until the entire amount of ethylcellulose was added. The granules were then wet milled using a size reduction mill (Granumill) and were subsequently loaded into fluid bed for drying.

TABLE 2

| Components for layered granule formulation | |
|---|---|
| Component | % w/w |
| hydrocodone bitartrate | 10 |
| polymer granules (EC, HPMC and Compritol) | 85 |
| Hypromellose 2910 | 5 |
| TOTAL | 100 |

The prepared granules were then layered in a bottom spray fluid bed coater with a 12% aqueous solution of hydrocodone bitartrate and HPMC 2910.

TABLE 3

| Components for coated granules formulation | |
|---|---|
| Component | % w/w |
| Hydrocodone bitartrate layered granules, 10% | 50 |
| Eudragit E-100 | 33 |
| magnesium stearate | 17 |
| TOTAL | 100 |

The hydrocodone bitartrate layered granules were then coated in a bottom spray fluid bed coater with 25% alcoholic suspension of Eudragit E-100 copolymer and magnesium stearate. The resulting coated granules were subsequently used for further blending and compression process.

Example 2: Hydrocodone/Acetaminophen Tablets

TABLE 4

| Hydrocodone/acetaminophen Tablet Formulation | | |
|---|---|---|
| Component | % | mg/tablet |
| Hydrocodone bitartrate coated granules, 5% | 20.0 | 200 |
| Paracetamol[1] | 33.7 | 337 |
| mannitol | 10.3 | 103 |
| carbopol | 5.0 | 50 |
| microcrystalline cellulose | 12.0 | 120 |
| crospovidone | 15.0 | 150 |
| sodium bicarbonate | 3.0 | 30 |
| magnesium stearate | 1.0 | 10 |
| Total | 100 | 1000 |

Contains 95% acetaminophen (APAP) and 5% gelatin

The coated granules were prepared according to Example 1 above and mixed with paracetamol and other excipients (carbomer, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

Example 3: Hydrocodone Bitartrate/Acetaminophen

TABLE 5

| Hydrocodone/acetaminophen Granule Formulation Core Shell composition | | |
|---|---|---|
| Component | Location | mg/tablet |
| HPMC K100M | Core | 51.1 |
| compritol | Core | 21.9 |
| Ethocel | Core | 12 |
| hydrocodone bitartrate | API layer | 10 |
| HPMC 2910 | API layer | 5 |
| Eudragit E-100 | Film | 66.7 |
| magnesium stearate | Film | 33.3 |
| Total | | 200 |

TABLE 6

| Hydrocodone/acetaminophen Tablet Formulation | |
|---|---|
| Components | mg/tablet |
| Core Shell composition (above) | 200 |
| APAP | 325 |
| gelatin | 12.1 |
| mannitol | 42.9 |
| carbopol | 50 |
| microcrystalline cellulose | 130 |
| crospovidone | 200 |
| sodium bicarbonate | 30 |
| magnesium stearate | 10 |
| Total | 1000 |

TABLE 7

Hydrocodone/acetaminophen Overall Tablet composition
Overall Tablet composition

| Components | mg/tablet |
|---|---|
| HPMC K100M | 51.1 |
| compritol | 21.9 |
| Ethocel | 12 |
| hydrocodone bitartrate | 10 |
| HPMC 2910 | 5 |
| Eudragit E-100 | 66.7 |
| APAP* | 325 |
| gelatin | 12.1 |
| mannitol | 42.9 |
| carbopol | 50 |
| microcrystalline cellulose | 130 |
| crospovidone | 200 |
| sodium bicarbonate | 30 |
| magnesium stearate | 43.3 |
| Total | 1000 |

*acetaminophen (acetyl-para-aminophenol).

Coated granules were prepared according to the procedure described in Example 1. The prepared coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

Example 4: Hydrocodone Bitartrate/Acetaminophen

TABLE 8

Hydrocodone/acetaminophen granule composition
Core Shell composition

| Component | Location | mg/tablet |
|---|---|---|
| HPMC K100M | core | 25.5 |
| compritol | core | 10.9 |
| Ethocel | core | 6 |
| hydrocodone bitartrate | API layer | 5 |
| HPMC 2910 | API layer | 2.5 |
| Eudragit E-100 | film | 33.4 |
| magnesium stearate | film | 16.7 |
| Total | | 100 |

TABLE 9

Hydrocodone/acetaminophen tablets

| Component | mg/Tab |
|---|---|
| Core Shell composition (above) | 100 |
| APAP | 325 |
| gelatin | 12.14 |
| mannitol | 34.88 |
| carbopol | 50 |
| microcrystalline cellulose | 96 |
| crospovidone | 144 |
| sodium bicarbonate | 30 |
| magnesium stearate | 8 |
| Total | 800.02 |

Coated granules were prepared according to the procedure described in Example 1. The prepared coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

TABLE 10

Hydrocodone/acetaminophen tablet composition
Overall Tablet composition

| Components | mg/tablet |
|---|---|
| HPMC K100M | 25.5 |
| compritol | 10.9 |
| ethocel | 6 |
| hydrocodone bitartrate | 5 |
| HPMC 2910 | 2.5 |
| Eudragit E-100 | 33.4 |
| APAP | 325 |
| gelatin | 12.14 |
| mannitol | 34.88 |
| carbopol | 50 |
| microcrystalline cellulose | 96 |
| crospovidone | 144 |
| sodium bicarbonate | 30 |
| magnesium stearate | 24.7 |
| Total | 800.02 |

Example 5: Hydrocodone Bitartrate/Acetaminophen

TABLE 11

Hydrocodone/acetaminophen granule composition
Core Shell composition

| Component | Location | mg/tablet |
|---|---|---|
| HPMC K100M | core | 50.1 |
| compritol | core | 21.5 |
| ethocel | core | 11.8 |
| hydrocodone bitartrate | API layer | 9.8 |
| HPMC 2910 | API layer | 4.9 |
| Eudragit E-100 | film | 65.4 |
| magnesium stearate | film | 32.7 |
| Total | | 196.2 |

TABLE 12

Hydrocodone/acetaminophen tablet composition

| Component | mg/TAB |
|---|---|
| Core Shell composition (above) | 196.1 |
| APAP | 325 |
| gelatin | 12.14 |
| mannitol | 46.2 |
| carbopol | 50 |
| microcrystalline cellulose | 130 |
| crospovidone | 200 |
| red iron oxide | 0.6 |
| sodium bicarbonate | 30 |
| magnesium stearate | 10 |
| Total | 1000 |

Coated granules were prepared according to the procedure described in Example 1. The prepared coated granules were then mixed with acetaminophen and other excipients (carbopol, crospovidone, sodium bicarbonate, mannitol, red iron oxide, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

TABLE 13

Hydrocodone/acetaminophen tablet composition
Overall Tablet composition

| Components | mg/tablet |
|---|---|
| HPMC K100M | 50.1 |
| compritol | 21.5 |
| ethocel | 11.8 |
| hydrocodone bitartrate | 9.8 |
| HPMC 2910 | 4.9 |
| Eudragit E-100 | 65.4 |
| APAP | 325 |
| gelatin | 12.14 |
| mannitol | 46.2 |
| carbopol | 50 |
| microcrystalline cellulose | 130 |
| crospovidone | 200 |
| red iron oxide | 0.6 |
| sodium bicarbonate | 30 |
| magnesium stearate | 42.7 |
| Total | 1000.14 |

Example 6: Oxycodone Hydrochloride (Single API) (Celphere Core)

TABLE 14

Oxycodone granule composition
Core Shell composition

| Components | Location | mg/tablets |
|---|---|---|
| Celphere (MCC) | core | 42 |
| oxycodone hydrochloride | API layer | 5.2 |
| HPMC 2910 | API layer | 1.7 |
| Eudragit E-100 | film | 1.9 |
| magnesium stearate | film | 0.6 |
| Total | | 51.4 |

Microcrystalline cellulose particles were layered in a bottom spray fluid bed coater with a 12% aqueous solution of oxycodone hydrochloride and HPMC 2910.

The oxycodone hydrochloride layered particles were then coated in a bottom spray fluid bed coater with 25% alcoholic suspension of Eudragit E-100 copolymer and magnesium stearate. The resulting coated particles were subsequently used for further blending and compression process.

TABLE 15

Oxycodone tablet composition

| Component | mg/TAB |
|---|---|
| Core Shell composition (above) | 51.54 |
| lactose | 96.46 |
| microcrystalline cellulose | 40 |
| crospovidone | 10 |
| magnesium stearate | 2 |
| Total | 200 |

The coated particles were mixed with other excipients (crospovidone and lactose) and blended in a V-blender for 30 minutes. Magnesium stearate was then added to lubricate the blend and the mixture was blended for an additional 5 minutes prior to compressing into oxycodone tablets.

TABLE 16

Oxycodone hydrochloride tablet composition
Overall Tablet composition

| Components | mg/tablet |
|---|---|
| microcrystalline cellulose | 82 |
| oxycodone hydrochloride | 5.2 |
| HPMC 2910 | 1.7 |
| Eudragit E-100 | 1.9 |
| lactose | 96.46 |
| crospovidone | 10 |
| magnesium stearate | 2.6 |
| Total | 199.86 |

Example 7: Hydrocodone Bitartrate/Acetaminophen (Sugar Sphere Core)

TABLE 17

Hydrocodone bitartrate granule composition
Core Shell composition

| Component | Location | mg/tablet |
|---|---|---|
| sugar sphere | core | 47.3 |
| PEO | core | 24.7 |
| EPO | core | 20.5 |
| hydrocodone bitartrate | API layer | 5 |
| HPMC 2910 | API layer | 2.5 |
| Eudragit E-100 | film | 75 |
| magnesium stearate | film | 25 |
| Total | | 200 |

Sugar sphere particles were layered in a bottom spray fluid bed coater with an aqueous solution of hydrocodone bitartrate and HPMC 2910.

The hydrocodone bitartrate layered particles were then coated in a bottom spray fluid bed coater with 25% alcoholic suspension of Eudragit E-100 copolymer and magnesium stearate. The resulting coated particles were subsequently used for further blending and compression process.

TABLE 18

Hydrocodone bitartrate tablet composition

| | mg/tablet |
|---|---|
| Core Shell composition (above) | 200 |
| APAP | 325 |
| binder | 17.8 |
| mannitol | 192.2 |
| microcrystalline cellulose | 200 |
| crospovidone | 50 |
| magnesium stearate | 15 |
| Total | 1000 |

The coated spheres were mixed with acetaminophen and other excipients (mannitol, microcrystalline cellulose, binder and crospovidone) and blended in a V-blender for 30 minutes. Magnesium stearate was then added to lubricate the blend and the mixture was blended for an additional 5 minutes prior to compressing into oxycodone tablets.

TABLE 19

Hydrocodone bitartrate tablet composition
Overall Tablet composition

| Components | mg/tablet |
| --- | --- |
| sugar | 47.3 |
| PEO(polyethylene oxide) | 24.7 |
| EPO(Eudragit E-PO) | 20.5 |
| hydrocodone bitartrate | 5 |
| HPMC 2910 | 2.5 |
| Eudragit E-100 | 75 |
| APAP | 325 |
| binder | 17.8 |
| mannitol | 192.2 |
| microcrystalline cellulose | 200 |
| crospovidone | 50 |
| magnesium stearate | 40 |
| Total | 1000 |

Example 8: Hydrocodone Bitartrate/Acetaminophen (Celphere Core)

TABLE 20

Hydrocodone bitartrate granule composition
Core Shell composition

| Component | Location | mg/tablet |
| --- | --- | --- |
| Celphere (MCC) | core | 117.5 |
| hydrocodone bitartrate | API layer | 5 |
| HPMC 2910 | API layer | 2.5 |
| Eudragit E-100 | film | 83.4 |
| magnesium stearate | film | 41.6 |
| Total | | 250 |

TABLE 21

Hydrocodone bitartrate tablet composition

| Component | mg/tablet |
| --- | --- |
| Core Shell composition (above) | 250 |
| APAP | 325 |
| gelatin | 12.14 |
| mannitol | 102.9 |
| microcrystalline cellulose | 120 |
| xanthan gum | 30 |
| crospovidone | 150 |
| magnesium stearate | 10 |
| Total | 1000.04 |

Coated spheres were prepared as in Example 7, and mixed with acetaminophen and other excipients (mannitol, microcrystalline cellulose, xanthan gum and crospovidone) and blended in a V-blender for 30 minutes. Magnesium stearate was then added to lubricate the blend and the mixture was blended for an additional 5 minutes prior to compressing into hydrocodone tablets.

TABLE 22

Hydrocodone bitartrate granule composition
Overall Tablet composition

| Component | mg/tablet |
| --- | --- |
| microcrystalline cellulose | 237.5 |
| hydrocodone bitartrate | 5 |
| HPMC 2910 | 2.5 |
| Eudragit E-100 | 83.4 |
| APAP | 325 |
| gelatin | 12.14 |
| mannitol | 102.9 |
| xanthan gum | 30 |
| crospovidone | 150 |
| magnesium stearate | 51.6 |
| Total | 1000.04 |

Example 9: Hydrocodone Bitartrate/Acetaminophen (Celphere Core)

TABLE 23

Hydrocodone bitartrate granule composition
Core Shell composition

| Component | Location | mg/tablet |
| --- | --- | --- |
| Celphere (MCC) | core | 117.5 |
| hydrocodone bitartrate | API layer | 5 |
| HPMC 2910 | API layer | 2.5 |
| Eudragit E-100 | film | 83.4 |
| magnesium stearate | film | 41.6 |
| Total | | 250 |

TABLE 24

Hydrocodone bitartrate tablet composition

| Component | mg/tablet |
| --- | --- |
| Core Shell composition (above) | 250 |
| APAP | 325 |
| gelatin | 12.14 |
| mannitol | 84.9 |
| microcrystalline cellulose | 120 |
| Carbopol | 30 |
| sodium bicarbonate | 18 |
| crospovidone | 150 |
| magnesium stearate | 10 |
| Total | 1000.04 |

Coated spheres were prepared as in Example 7, and mixed with acetaminophen and other excipients (mannitol, microcrystalline cellulose, carbopol, sodium bicarbonate and crospovidone) and blended in a V-blender for 30 minutes. Magnesium stearate was then added to lubricate the blend and the mixture was blended for an additional 5 minutes prior to compressing into tablets.

TABLE 25

Hydrocodone bitartrate tablet composition
Overall Tablet composition

| Components | mg/tablet |
| --- | --- |
| hydrocodone bitartrate | 5 |
| HPMC 2910 | 2.5 |
| Eudragit E-100 | 83.4 |

TABLE 25-continued

Hydrocodone bitartrate tablet composition
Overall Tablet composition

| Components | mg/tablet |
| --- | --- |
| APAP | 325 |
| gelatin | 12.14 |
| mannitol | 84.9 |
| microcrystalline cellulose | 237.5 |
| carbopol | 30 |
| sodium bicarbonate | 18 |
| crospovidone | 150 |
| magnesium stearate | 51.6 |
| Total | 1000.04 |

Example 10: Oxycodone Hydrochloride/Acetaminophen

TABLE 26

Oxycodone bitartrate granule composition
Core Shell composition

| Component | Location | mg/tablet |
| --- | --- | --- |
| HPMC K100M | core | 71 |
| Compritol | core | 30.5 |
| Ethocel | core | 16.8 |
| oxycodone hydrochloride | API layer | 4.5 |
| HPMC 2910 | API layer | 2.2 |
| Eudragit E-100 | film | 83.4 |
| magnesium stearate | film | 41.6 |
| Total | | 250 |

TABLE 27

Oxycodone tablet composition

| Component | mg/tablet |
| --- | --- |
| Core Shell composition (above) | 250 |
| APAP | 325 |
| gelatin | 12.14 |
| lactose | 84.9 |
| carbopol | 30 |
| microcrystalline cellulose | 120 |
| crospovidone | 150 |
| sodium bicarbonate | 18 |
| magnesium stearate | 10 |
| Total | 1000.04 |

Granules were prepared and coated as described in Example 1. The coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into oxycodone/acetaminophen tablets.

TABLE 28

Oxycodone/acetaminophen tablet composition
Overall Tablet composition

| Components | mg/tablet |
| --- | --- |
| HPMC K100M | 71 |
| compritol | 30.5 |
| ethocel | 16.8 |
| oxycodone hydrochloride | 4.5 |
| HPMC 2910 | 2.2 |
| Eudragit E-100 | 83.4 |
| APAP | 325 |
| gelatin | 12.14 |
| lactose | 84.9 |
| carbopol | 30 |
| microcrystalline cellulose | 120 |
| crospovidone | 150 |
| sodium bicarbonate | 18 |
| magnesium stearate | 51.6 |
| Total | 1000 |

Example 11: Oxycodone Hydrochloride/Acetaminophen

TABLE 29

Oxycodone hydrochloride granule composition
Core Shell composition

| Component | Location | mg/tablet |
| --- | --- | --- |
| HPMC K100M | core | 71 |
| compritol | core | 30.3 |
| ethocel | core | 16.7 |
| oxycodone hydrochloride | API layer | 5 |
| HPMC 2910 | API layer | 2.5 |
| Eudragit E-100 | film | 83.4 |
| magnesium stearate | film | 41.6 |
| Total | | 250.5 |

TABLE 30

Oxycodone/acetaminophen tablet composition

| Component | mg/tablet |
| --- | --- |
| Core Shell composition (above) | 250 |
| APAP | 325 |
| gelatin | 12.14 |
| mannitol | 82.9 |
| xanthan gum | 50 |
| microcrystalline cellulose | 120 |
| crospovidone | 150 |
| magnesium stearate | 10 |
| Total | 1000.04 |

Granules were prepared and coated as described in Example 1. The coated granules were then mixed with acetaminophen and other excipients (xanthan gum, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into oxycodone/acetaminophen tablets.

TABLE 31

Oxycodone/acetaminophen tablet composition
Overall Tablet composition

| Components | mg/tablet |
| --- | --- |
| HPMC K100M | 71 |
| Compritol | 30.3 |
| Ethocel | 16.7 |
| oxycodone hydrochloride | 5 |
| HPMC 2910 | 2.5 |
| Eudragit E-100 | 83.4 |
| APAP | 325 |
| gelatin | 12.14 |
| mannitol | 82.9 |
| xanthan gum | 50 |
| microcrystalline cellulose | 120 |
| crospovidone | 150 |
| magnesium stearate | 51.6 |
| Total | 1000.54 |

Example 12: Oxycodone Hydrochloride/Acetaminophen

TABLE 32

Oxycodone hydrochloride granule composition
Core Shell composition

| Component | Location | mg/tablet |
| --- | --- | --- |
| HPMC K100M | core | 71 |
| Compritol | core | 30.5 |
| Ethocel | core | 16.8 |
| oxycodone hydrochloride | API layer | 4.5 |
| HPMC 2910 | API layer | 2.2 |
| Eudragit E-100 | film | 83.4 |
| magnesium stearate | film | 41.6 |
| Total | | 250 |

TABLE 33

Oxycodone/acetaminophen tablet composition

| Component | mg/tablet |
| --- | --- |
| Core Shell composition (above) | 250 |
| APAP | 325 |
| gelatin | 12.14 |
| mannitol | 52.9 |
| Carbopol | 50 |
| microcrystalline cellulose | 120 |
| Crospovidone | 150 |
| sodium bicarbonate | 30 |
| magnesium stearate | 10 |
| Total | 1000.04 |

Granules were prepared and coated as described in Example 1. The coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into oxycodone/acetaminophen tablets.

TABLE 34

Oxycodone/acetaminophen tablet composition
Overall Tablet composition

| Components | mg/tablet |
| --- | --- |
| HPMC K100M | 71 |
| compritol | 30.5 |
| ethocel | 16.8 |
| oxycodone hydrochloride | 4.5 |
| HPMC 2910 | 2.2 |
| Eudragit E-100 | 83.4 |
| APAP | 325 |
| gelatin | 12.14 |
| mannitol | 52.9 |
| carbopol | 50 |
| microcrystalline cellulose | 120 |
| crospovidone | 150 |
| sodium bicarbonate | 30 |
| magnesium stearate | 51.6 |
| Total | 1000 |

Example 13: Hydrocodone Bitartrate/Acetaminophen

TABLE 35

Hydrocodone bitartrate granule composition
Core Shell composition

| Component | Location | mg/tablet |
| --- | --- | --- |
| HPMC K100M | core | 51 |
| compritol | core | 21.9 |
| ethocel | core | 12 |
| hydrocodone bitartrate | API layer | 10 |
| HPMC 2910 | API layer | 5 |
| Eudragit E-100 | film | 66.7 |
| magnesium stearate | film | 33.3 |
| Total | | 199.9 |

TABLE 36

Hydrocodone Bitartrate/APAP tablet composition

| Component | mg/TAB |
| --- | --- |
| Core Shell composition (above) | 200 |
| APAP | 325 |
| gelatin | 12.14 |
| mannitol | 74.86 |
| carbopol | 80 |
| microcrystalline cellulose | 100 |
| crospovidone | 150 |
| sodium bicarbonate | 48 |
| magnesium stearate | 10 |
| Total | 1000 |

Granules were prepared and coated as described in Example 1. The coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

TABLE 37

Hydrocodone Bitartrate/APAP tablet composition
Overall Tablet composition

| Components | mg/tablet |
| --- | --- |
| HPMC K100M | 51 |
| Compritol | 21.9 |
| Ethocel | 12 |
| hydrocodone bitartrate | 10 |
| HPMC 2910 | 5 |
| Eudragit E-100 | 66.7 |
| APAP | 325 |
| gelatin | 12.14 |
| mannitol | 74.86 |
| carbopol | 80 |
| microcrystalline cellulose | 100 |
| crospovidone | 150 |
| sodium bicarbonate | 48 |
| magnesium stearate | 43.3 |
| Total | 999.9 |

Example 14: Hydrocodone Bitartrate/Acetaminophen

TABLE 38

Hydrocodone Bitartrate granule composition
Core Shell composition

| Component | Location | mg/tablet |
| --- | --- | --- |
| HPMC K100M | core | 42 |
| compritol | core | 18.1 |
| ethocel | core | 9.9 |
| hydrocodone bitartrate | API layer | 10 |
| HPMC 2910 | API layer | 5 |
| Eudragit E-100 | film | 56.8 |
| magnesium stearate | film | 28.4 |
| Total | | 170.2 |

TABLE 39

Hydrocodone/APAP tablet composition

| Component | mg/tablet |
| --- | --- |
| Core Shell composition (above) | 170 |
| APAP | 325 |
| gelatin | 12.14 |
| mannitol | 24.905 |
| carbopol | 49.98 |
| microcrystalline cellulose | 102 |
| crospovidone | 127.5 |
| sodium bicarbonate | 30.005 |
| magnesium stearate | 8.5 |
| Total | 850.03 |

Granules were prepared and coated as described in Example 1. The coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

TABLE 40

Hydrocodone/APAP tablet composition
Overall Tablet composition

| Components | mg/tablet |
| --- | --- |
| HPMC K100M | 42 |
| compritol | 18.1 |
| ethocel | 9.9 |
| hydrocodone bitartrate | 10 |
| HPMC 2910 | 5 |
| Eudragit E-100 | 56.8 |
| APAP | 325 |
| gelatin | 12.14 |
| mannitol | 24.905 |
| carbopol | 49.98 |
| microcrystalline cellulose | 102 |
| crospovidone | 127.5 |
| sodium bicarbonate | 30.005 |
| magnesium stearate | 36.9 |
| Total | 850.23 |

Example 15: Hydrocodone Bitartrate/Acetaminophen

TABLE 41

Hydrocodone bitartrate granule composition
Core Shell composition

| Component | Location | mg/tablet |
| --- | --- | --- |
| HPMC K100M | core | 51 |
| compritol | core | 21.9 |
| ethocel | core | 12 |
| hydrocodone bitartrate | API layer | 10 |
| HPMC 2910 | API layer | 5 |
| Eudragit E-100 | film | 66.7 |
| magnesium stearate | film | 33.3 |
| Total | | 199.9 |

TABLE 42

Hydrocodone/APAP tablet composition

| Component | mg/tablet |
| --- | --- |
| Core Shell composition (above) | 200 |
| APAP | 325 |
| gelatin | 12.14 |
| mannitol | 134.9 |
| carbopol | 30 |
| microcrystalline cellulose | 120 |
| crospovidone | 150 |
| sodium bicarbonate | 18 |
| magnesium stearate | 10 |
| Total | 1000.04 |

Granules were prepared and coated as described in Example 1. The coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

TABLE 43

Hydrocodone/APAP tablet composition
Overall Tablet composition

| Component | mg/tablet |
| --- | --- |
| HPMC K100M | 51 |
| compritol | 21.9 |
| ethocel | 12 |
| hydrocodone bitartrate | 10 |
| HPMC 2910 | 5 |
| Eudragit E-100 | 66.7 |
| APAP | 325 |
| gelatin | 12.14 |
| mannitol | 134.9 |
| carbopol | 30 |
| microcrystalline cellulose | 120 |
| crospovidone | 150 |
| sodium bicarbonate | 18 |
| magnesium stearate | 43.3 |
| Total | 999.94 |

Example 16: Hydrocodone Bitartrate/Acetaminophen

TABLE 44

Hydrocodone bitartrate granule composition
Core Shell composition

| Component | Location | mg/tablet |
| --- | --- | --- |
| HPMC K100M | core | 51 |
| compritol | core | 21.9 |
| ethocel | core | 12 |
| hydrocodone bitartrate | API layer | 10 |
| HPMC 2910 | API layer | 5 |
| Eudragit E-100 | film | 66.7 |
| magnesium stearate | film | 33.3 |
| Total |  | 199.9 |

TABLE 45

Hydrocodone/APAP tablet composition

| Component | mg/tablet |
| --- | --- |
| Core Shell composition (above) | 200 |
| APAP | 325 |
| gelatin | 12.14 |
| mannitol | 102.9 |
| carbopol | 50 |
| microcrystalline cellulose | 120 |
| Crospovidone | 150 |
| sodium bicarbonate | 30 |
| magnesium stearate | 10 |
| Total | 1000.04 |

Granules were prepared and coated as described in Example 1. The coated granules were then mixed with acetaminophen and other excipients (carbopol, crospovidone, sodium bicarbonate, mannitol, microcrystalline cellulose) and blended in a V-blender for 30 minutes. Magnesium stearate was then added to lubricate the blend and the mixture was blended for an additional 5 minutes prior to compressing into hydrocodone/acetaminophen tablets.

TABLE 46

Hydrocodone/APAP tablet composition
Overall Tablet composition

| Components | mg/tablet |
| --- | --- |
| HPMC K100M | 51 |
| Compritol | 21.9 |
| Ethocel | 12 |
| hydrocodone bitartrate | 10 |
| HPMC 2910 | 5 |
| Eudragit E-100 | 66.7 |
| APAP | 325 |
| gelatin | 12.14 |
| mannitol | 102.9 |
| carbopol | 50 |
| microcrystalline cellulose | 120 |
| crospovidone | 150 |
| sodium bicarbonate | 30 |
| magnesium stearate | 43.3 |
| Total | 999.94 |

Example 17: Hydrocodone Bitartrate/Acetaminophen

TABLE 47

Hydrocodone/APAP tablet composition

| Components (mg/tab) | 5/325 mg | 7.5/325 mg | 10/325 mg |
| --- | --- | --- | --- |
| Hypromellose K100M PH | 25.5 | 38.3 | 51.1 |
| Compritol 888 ATO | 11 | 16.4 | 21.9 |
| ethyl cellulose | 6 | 9 | 12 |
| hydrocodone bitartrate | 5 | 7.5 | 10 |
| Hypromellose 2910 | 2.5 | 3.8 | 5 |
| Eudragit E-100 | 33.4 | 50 | 66.7 |
| paracetamol Dc272n** | 342.11 | 342.11 | 342.11 |
| mannitol Ez | 29.89 | 38.81 | 37.29 |
| carbopol 71g | 50 | 50 | 50 |
| microcrystalline cellulose | 96 | 108 | 130 |
| crospovidone | 144 | 171 | 200 |
| sodium bicarbonate #1 | 30 | 30 | 30 |
| FD&C Blue #2 Ht Aluminum Lake | NA | 0.54 | NA |
| Iron Oxide Yellow 510p | NA | 0.54 | NA |
| Iron Oxide Red 212p | NA | NA | 0.6 |
| magnesium stearate non-bovine | 24.6 | 34 | 43.3 |
| alcohol SDA-3A, anhydrous* | * | * | * |
| purified water* | * | * | * |
| Total Tablet Weight | 800 | 900 | 1000 |

*Removed during Processing
**Contains 95% acetaminophen (APAP) and 5% binder.

Granules were prepared and coated as described in Example 1. The coated granules were then mixed with Paracetamol and other excipients (carbopol, crospovidone, sodium bicarbonate, mannitol, microcrystalline cellulose and coloring agents) and blended in a V-blender for 30 minutes. Magnesium stearate was then added to lubricate the blend and the mixture was blended for an additional 5 minutes prior to compressing into hydrocodone/acetaminophen tablets.

TABLE 48

Hydrocodone bitartrate granule composition

|  | 5/325 mg Dose % | 7.5/325 mg Dose % | 10/325 mg Dose % |
|---|---|---|---|
| Granulation | | | |
| Hypromellose | 3.19 | 4.26 | 5.11 |
| Compritol 888 ATO | 1.37 | 1.83 | 2.19 |
| ethylcellulose | 0.75 | 1 | 1.2 |
| alcohol SDA-3A, anhydrous | * | * | * |
| purified water | * | * | * |
| TOTAL | 5.31 | 7.09 | 8.5 |
| Layering | | | |
| hydrocodone bitartrate | 0.63 | 0.83 | 1 |
| polymer granules (EC, HPMC and Compritol) | 5.31 | 7.09 | 8.5 |
| Hypromellose 2910 | 0.31 | 0.42 | 0.5 |
| purified water | * | * | * |
| TOTAL | 6.25 | 8.34 | 10 |
| Coating | | | |
| hydrocodone layered granules, 10% | 6.25 | 8.34 | 10 |
| Eudragit E-100 | 4.17 | 5.56 | 6.67 |
| magnesium stearate | 2.08 | 2.77 | 3.33 |
| alcohol, SDA-3A, anhydrous | * | * | * |
| TOTAL | 12.5 | 16.67 | 20 |

* Removed during Processing

Example 18: Armodafinil

TABLE 49

Armodafinil tablet composition
Armodafinil:

| Components (mg/tab) | 50 mg | 150 mg | 200 mg |
|---|---|---|---|
| hypromellose | 64.26 | 36 | 48 |
| Compritol 888 ATO | 17.85 | 10 | 14 |
| ethylcellulose | 10.71 | 10 | 14 |
| armodafinil | 50 | 150 | 200 |
| Eudragit E-100 | 21 | 30 | 40 |
| Mannitol Ez | 17 | 25 | 25 |
| Carbopol 71g | 50 | 50 | 50 |
| microcrystalline cellulose | 100 | 125 | 125 |
| crospovidone | 150 | 200 | 200 |
| sodium bicarbonate #1 | 30 | 30 | 30 |
| magnesium stearate non-bovine | 71 | 25 | 32 |
| Lutrol F68 (1:5) | 150 | 200 | 200 |
| sodium lauryl sulphate (3%) | 23 | 30 | 40 |
| Alcohol SDA-3A, anhydrous* | * | * | * |
| purified water* | * | * | * |
| Total Tablet Weight | 754.82 | 921 | 1018 |

*Removed during Processing

Granules are prepared and coated as described in Example 1. The coated granules are then mixed with the other excipients (carbopol, crospovidone, sodium bicarbonate, mannitol, microcrystalline cellulose) and blended in a V-blender for 30 minutes. Magnesium stearate (non-bovine) is then added to lubricate the blend and the mixture is blended for an additional 5 minutes prior to compressing into armodafinil tablets.

TABLE 50

Armodafinil granule compositions

|  | 50 mg Dose | | 150 mg Dose | | 200 mg Dose | |
|---|---|---|---|---|---|---|
|  | mg/g | mg/tab | mg/g | mg/tab | mg/g | mg/tab |
| Granulation | | | | | | |
| hypromellose | 450 | 64.26 | 175 | 36 | 175 | 48 |
| armodafinil | 350 | 49.98 | 725 | 150 | 725 | 200 |
| Compritol 888 ATO | 125 | 17.85 | 50 | 10 | 50 | 14 |
| ethylcellulose | 75 | 10.71 | 50 | 10 | 50 | 14 |
| Alcohol SDA-3A, anhydrous | * | * | * | * | * | * |
| purified water | * | * | * | * | * | * |
| TOTAL | 1000 | 142.8 | 1000 | 206 | 1000 | 276 |
| Coating | | | | | | |
| armodafinil granules, 35% | 820 | 142.84 | 820 | 207 | 820 | 276 |
| Eudragit E-100 | 120 | 20.90 | 120 | 30 | 120 | 40 |
| magnesium stearate | 60 | 10.45 | 60 | 15 | 60 | 20 |
| Alcohol, SDA-3A, anhydrous | * | * | * | * | * | * |
| TOTAL | 1000 | 174.2 | 1000 | 252 | 1000 | 336 |

* Removed during Processing

Example 19: Phenobarbital

TABLE 51

Phenobarbital Tablet compositions

| Components (mg/tab) | 15 mg | 30 mg | 60 mg | 100 mg |
|---|---|---|---|---|
| hypromellose | 19.3 | 38.6 | 77.2 | 128.52 |
| Compritol 888 ATO | 5.4 | 10.7 | 21.4 | 35.7 |
| ethylcellulose | 3.2 | 6.4 | 12.9 | 21.43 |
| phenobarbital | 15 | 30 | 60 | 100 |
| Eudragit E-100 | 6.3 | 15.5 | 25.1 | 42 |
| Mannitol EZ | 20 | 20 | 20 | 20.1 |
| Carbopol 71g | 50 | 50 | 50 | 50 |
| microcrystalline cellulose | 100 | 100 | 100 | 100 |
| crospovidone | 130 | 130 | 130 | 200 |
| sodium bicarbonate #1 | 30 | 30 | 30 | 30 |
| magnesium stearate non-bovine | 9.1 | 12.3 | 19.1 | 31 |
| Lutrol F68 (1:5) | 100 | 100 | 120 | 200 |
| sodium lauryl sulphate (3%) | 22.8 | 28 | 35 | 50 |
| Alcohol SDA-3A, anhydrous* | * | * | * | * |
| purified water* | * | * | * | * |
| Total Tablet Weight | 511.1 | 571.5 | 700.7 | 1008.7 |

*Removed during Processing

TABLE 52

Phenobarbital granule compositions

|  | 15 mg Dose | | 30 mg Dose | | 60 mg Dose | | 100 mg Dose | |
|---|---|---|---|---|---|---|---|---|
|  | mg/g | mg/tab | mg/g | mg/tab | mg/g | mg/tab | mg/g | mg/tab |
| Granulation | | | | | | | | |
| Hypromellose | 450 | 19.31 | 450 | 38.57 | 450 | 77.18 | 450 | 128.57 |
| phenobarbital | 350 | 15.02 | 350 | 30 | 350 | 60.03 | 350 | 100 |
| Compritol 888 ATO | 125 | 5.36 | 125 | 10.71 | 125 | 21.44 | 125 | 35.71 |
| ethyl cellulose | 75 | 3.22 | 75 | 6.43 | 75 | 12.86 | 75 | 21.43 |
| Alcohol SDA-3A, | * | * | * | * | * | * | * | * |
| Purified Water | * | * | * | * | * | * | * | * |
| TOTAL | 1000 | 42.91 | 1000 | 85.71 | 1000 | 171.51 | 1000 | 285.71 |
| Coating | | | | | | | | |
| phenobarbital, 35% | 820 | 42.89 | 820 | 85.69 | 820 | 171.46 | 820 | 285.69 |
| Eudragit E-100 | 120 | 6.28 | 120 | 12.54 | 120 | 25.09 | 120 | 41.81 |
| magnesium stearate | 60 | 3.14 | 60 | 6.27 | 60 | 12.55 | 60 | 20.90 |
| Alcohol, SDA-3A, | * | * | * | * | * | * | * | * |
| TOTAL | 1000 | 52.3 | 1000 | 104.5 | 1000 | 209.1 | 1000 | 348.4 |

* Removed during Processing

Granules are prepared and coated as described in Example 1. The coated granules are then mixed with the other excipients (carbopol, crospovidone, sodium bicarbonate, mannitol, microcrystalline cellulose) and blended in a V-blender for 30 minutes. Magnesium stearate (non-bovine) is then added to lubricate the blend and the mixture is blended for an additional 5 minutes prior to compressing into phenobarbital tablets.

Example 20: Diazepam

TABLE 53

Diazepam Tablet compositions

| Components | 2 mg (mg/tab) | 5 mg (mg/tab) | 10 mg (mg/tab) |
|---|---|---|---|
| Hypromellose K100M PH | 22.2 | 55.6 | 111.2 |
| Compritol 888 ATO | 9.5 | 23.8 | 47.64 |
| Ethyl cellulose N10 | 5.2 | 13.1 | 26.2 |
| diazepam | 2 | 5 | 10 |
| Hypromellose 2910 | 1 | 2.5 | 5 |
| Eudragit E-100 | 26.7 | 66.7 | 133.4 |
| mannitol Ez | 70 | 70 | 70 |
| carbopol 71g | 50 | 50 | 50 |
| microcrystalline cellulose | 95 | 95 | 94 |
| crospovidone | 90 | 95 | 150 |
| sodium bicarbonate #1 | 30 | 30 | 30 |
| magnesium stearate non- | 18.1 | 38.6 | 74.6 |
| Alcohol SDA-3A, | * | * | * |
| purified water* | * | * | * |
| Total Tablet Weight | 419.7 | 545.3 | 802.04 |

*Removed during processing

Granules are prepared and coated as described in Example 1. The coated granules are then mixed with the other excipients (carbopol, crospovidone, sodium bicarbonate, mannitol, microcrystalline cellulose) and blended in a V-blender for 30 minutes. Magnesium stearate (non-bovine) is then added to lubricate the blend and the mixture is blended for an additional 5 minutes prior to compressing into Diazepam tablets.

TABLE 54

Diazepam Coated Granule compositions

|  | 2 mg Dose | | 5 mg Dose | | 2 mg Dose | |
|---|---|---|---|---|---|---|
|  | mg/g | mg/tab | mg/g | mg/tab | mg/g | mg/tab |
| Granulation | | | | | | |
| hypromellose | 600.86 | 22.23 | 600.86 | 55.58 | 600.86 | 111.16 |
| Compritol 888 ATO | 257.51 | 9.53 | 257.51 | 23.82 | 257.51 | 47.64 |
| ethyl cellulose | 141.63 | 5.24 | 141.63 | 13.10 | 141.63 | 26.20 |
| Alcohol SDA-3A, | * | * | * | * | * | * |
| purified water | * | * | * | * | * | * |
| TOTAL Layering | 1000 | 37 | 1000 | 92.5 | 1000 | 185 |
| diazepam | 50 | 2 | 50 | 5 | 50 | 10 |
| polymer granules (EC, | 925 | 37 | 925 | 92.5 | 925 | 185 |
| Hypromellose 2910 | 25 | 1 | 25 | 2.5 | 25 | 5 |
| purified water | * | * | * | * | * | * |
| TOTAL Coated, 2.5% | 1000 | 40 | 1000 | 100 | 1000 | 200 |
| diazepam layered | 500 | 40 | 500 | 100 | 500 | 200 |
| Eudragit E-100 | 333.6 | 26.69 | 333.6 | 66.71 | 333.6 | 133.43 |
| magnesium stearate | 166.4 | 13.31 | 166.4 | 33.29 | 166.4 | 66.57 |
| Alcohol, SDA-3A, | * | * | * | * | * | * |
| TOTAL | 1000 | 80 | 1000 | 200 | 1000 | 400 |

Example 21: Hydrocodone (Single API)

Granules are prepared and coated as described in Example 1. The coated granules are then mixed with the other excipients (carbopol, crospovidone, sodium bicarbonate, mannitol, microcrystalline cellulose) and blended in a V-blender for 30 minutes. Magnesium stearate (non-bovine)

is then added to lubricate the blend and the mixture is blended for an additional 5 minutes prior to compressing into hydrocodone tablets.

Example 22: Hydrocodone (Single API)—(Continued from Example 21 Above)

TABLE 55

Hydrocodone Tablet compositions

| Components | 5 mg (mg/tab) | 10 mg (mg/tab) |
|---|---|---|
| Hypromellose K100M PH | 25.5 | 51.1 |
| Compritol 888 ATO | 11 | 21.9 |
| Ethyl cellulose N10 | 6 | 12.04 |
| hydrocodone bitartrate | 5 | 10 |
| Hypromellose 2910 | 2.5 | 5 |
| Eudragit E-100 | 33.4 | 66.7 |
| Mannitol Ez | 70 | 70 |
| Carbopol 71G | 50 | 50 |
| microcrystalline cellulose | 95 | 95 |
| Crospovidone | 100 | 120 |
| Sodium Bicarbonate #1 | 30 | 30 |
| Magnesium Stearate Non-Bovine | 21.6 | 39.3 |
| Alcohol SDA-3A, Anhydrous* | * | * |
| purified water* | * | * |
| Total Tablet Weight | 450 | 571.04 |

*Removed during processing

TABLE 56

Hydrocodone bitartrate Coated Granule compositions

| | 5 mg Dose | | 10 mg Dose | |
|---|---|---|---|---|
| | mg/g | mg/tab | mg/g | mg/tab |
| Granulation | | | | |
| Hypromellose | 600.86 | 25.54 | 600.86 | 51.07 |
| Compritol 888 ATO | 257.51 | 10.94 | 257.51 | 21.89 |
| ethyl cellulose | 141.63 | 6.02 | 141.63 | 12.04 |
| Alcohol SDA-3A, anhydrous | * | * | * | * |
| purified water | * | * | * | * |
| TOTAL | 1000 | 42.5 | 1000 | 85 |
| Layering | | | | |
| hydrocodone bitartrate | 100 | 5 | 100 | 10 |
| polymer granules (EC, HPMC and Compritol) | 850 | 42.5 | 850 | 85 |
| Hypromellose 2910 | 50 | 2.5 | 50 | 5 |
| purified water | * | * | * | * |
| TOTAL | 1000 | 50 | 1000 | 100 |
| Coating | | | | |
| hydrocodone bitartrate layered granules, 10% | 500 | 50 | 500 | 100 |
| Eudragit E-100 | 333.6 | 33.36 | 333.6 | 66.71 |
| magnesium stearate | 166.4 | 16.64 | 166.4 | 33.29 |
| Alcohol, SDA-3A, anhydrous | * | * | * | * |
| TOTAL* (removed during processing) | 1000 | 100 | 1000 | 200 |

Example 23: Hydrocodone Bitartrate/Acetaminophen

Coated granules were prepared according to the Example 1 above. The prepared coated granules were then mixed with Paracetamol and other excipients (carbomer, crospovidone, sodium bicarbonate, mannitol, microcrystalline cellulose, colorants such as FD and C blue, red iron oxide or yellow iron oxide are premixed and blended in a bin blender for 30 minutes. Magnesium stearate was then added to lubricate the blend and the resulting mixture was blended for an additional 5 minutes prior to compressing into hydrocodone/acetaminophen tablets.

TABLE 57

Hydrocodone/APAP Tablet compositions

| Component (% w/w) | 5/325 mg | 7.5/325 mg | 10/325 mg |
|---|---|---|---|
| Hydrocodone bitartrate coated | 12.5 | 16.7 | 20.0 |
| Paracetamol* | 42.76 | 38.0 | 34.21 |
| Mannitol | 3.74 | 4.3 | 3.73 |
| carbopol | 6.25 | 5.6 | 5.0 |
| microcrystalline cellulose | 12.0 | 12.0 | 13.0 |
| Crospovidone | 18.0 | 19.0 | 20.0 |
| sodium bicarbonate | 3.75 | 3.3 | 3.0 |
| FD&C Blue #2 HT Aluminum Lake | NA | 0.06 | NA |
| Iron Oxide Red 212P | NA | NA | 0.06 |
| Iron Oxide Yellow 510P | NA | 0.06 | NA |
| magnesium stearate | 1.0 | 1.0 | 1.0 |
| Total | 100 | 100 | 100 |

*Contains 95% acetaminophen (APAP) and 5% binder

Example 24: Extraction Study of Formulations According to Examples 3

The dosage form (intact and crushed) prepared according to Example 3 above (10/325 mg hydrocodone bitartrate/Acetaminophen tablet) was taken up in a small volume of water and extracted to simulate the amount of hydrocodone that was available to abusers via intravenous (IV) route. The resultant mixture was assessed for ability to draw the mixture through a filter material into a syringe for IV injection. Various needle sizes and extraction volumes were evaluated. Filtrates were assayed by HPLC for content of hydrocodone bitartrate.

TABLE 58

Amount of hydrocodone extracted from two lots of 10/325 mg hydrocodone bitartrate/Acetaminophen tablets at 100° C. and Room Temperature (RT)

| | Intact tablet (mg) | | Crushed tablet (mg) | |
|---|---|---|---|---|
| Lot # | 100° C. | RT | 100° C. | RT |
| 1 | 0 mg | 0.09 mg | 0 mg | 0 mg |
| 2 | 0 mg | 0.07 mg | 0 mg | 0 mg |

Example 25: Simulated Nasal Fluid Extraction Study of Formulations According to Example 3

The dosage form prepared according to Example 3 above (10/325 mg hydrocodone bitartrate/Acetaminophen tablets) was crushed using a pestle and mortar and placed in 10 mL of simulated nasal fluid at 37° C., with gentle agitation to simulate the amount of hydrocodone bitartrate available for abuse by nasal insufflation. Aliquots were removed at 10 and 30 minutes for analysis of hydrocodone bitartrate by HPLC. The amount of hydrocodone bitartrate extracted from crushed tablets for simulated nasal insufflation is provided in the table below.

This method is for the determination of hydrocodone bitartrate released from simulated nasal fluid extractions of hydrocodone bitartrate extended-release tablets.

A. HPLC Analysis Parameters

| Column | GL Sciences Inertsil Phenyl-3, 4.6 mm × 50 mm, 5-μm |
|---|---|
| Column Temperature | 45° C. |
| Detection | UV at 280 nm |
| Solvent A | 0.1% HFBA in water |
| Solvent B | MeOH |
| Mobile Phase | 70:30 Solvent A:Solvent B |
| Injector Flush | 50:50 MeOH:water |
| Flow Rate | 2.0 mL/min |
| Injection Volume | 50 μL |
| Run Time | 4 min |
| Peak Response | Area |
| Diluent | 0.1N HCl |

B. HPLC Solution Preparation

Solvent A (0.1% HFBA in $H_2O$): Combine 1 mL of HFBA and 1 L of HPLC grade water, and mix well. Solvent A is stable for 14 days. Proportionate volumes may be prepared. Mobile Phase (70:30 Solvent A:MeOH): Combine 700 mL of Solvent A and 300 mL of MeOH, and mix well. Prepared solutions are stable for 1 month. Proportionate volumes may be prepared. Alternatively, the HPLC pump may be used to mix the mobile phase. Diluent/Medium (0.1 N HCl): Combine 25 mL of 12 N HCl and 3 L of DI water, and mix well. 0.1N HCl is stable for 4 weeks. Proportionate volumes may be prepared. Injector Flush (50:50 MeOH:$H_2O$): Combine 500 mL of MeOH and 500 mL of HPLC grade water, and mix well. 50:50 MeOH:$H_2O$ is stable for 1 month. Proportionate volumes may be prepared.

C. Simulated Nasal Fluid (SNF) Preparation

Add 8.7 g sodium chloride (NaCl) 3.0 g potassium chloride (KCl), 0.6 g calcium chloride ($CaCl_2$), 4.4 g sodium phosphate dibasic ($Na_2HPO_4$), and 1.1 g sodium phosphate monobasic ($NaH_2PO_4$) in one liter of water. Mix well. Measure and record pH (must be between 6.0 and 7.0). Store at room temperature. SNF is stable for 2 weeks. Proportionate volumes may be prepared.

D. Hydrocodone Bitartrate Standard Solution

Stock Standard Solution: Dry a portion of hydrocodone bitartrate standard at 2 hours under vacuum at 105° C. per the USP. In duplicate, accurately weigh 30 mg±5 mg of hydrocodone bitartrate into separate 100-mL volumetric flasks. Add approximately 50 mL of 0.1 N HCl diluent. Dissolve by sonication for approximately 10 minutes. Dilute to volume with diluent, and mix well. These are the stock standard solutions of approximately 300 micrograms/mL (as anhydrous hydrocodone bitartrate) and are stable for 29 days under ambient laboratory conditions (unprotected from light). Proportionate volumes may be prepared.

Working Standard Solution: Pipette 15 mL of each stock standard solution into separate 50-mL volumetric flasks. Dilute to volume with 0.1 N HCl diluent, and mix well. These working standard solutions are approximately 90 micrograms/mL (as anhydrous hydrocodone bitartrate) and are stable for 43 days under ambient laboratory conditions (unprotected from light). Proportionate volumes may be prepared.

E. Simulated Nasal Insufflation Extraction Sample Preparation

1. Crush one tablet and transfer approximately 575 mg, accurately weighed, of the crushed material to pre-labeled 20 mL glass vial. For drug substance controls, weigh an appropriate mass of material and transfer into a pre-labeled 20 mL glass vial.

2. Heat the water bath and simulated nasal fluid to 37° C.

3. Pipette 10 mL the pre-heated 37° C. simulated nasal fluid into each vial containing crushed tablet material.

4. Cap and invert two times to wet powder. Put vial on the metal shelf inside of the water bath and shake at 100 rpm.

5. At 10 min, take the vial out of shelf.

6. Uncap and withdraw a 3-mL solution from each of the vials using a micropipette.

7. Transfer solution into a 5-mL polypropylene syringe and filter the solution through a 25-mm diameter, 1-μm porosity glass filter into a glass test tube (16×100 mm).

8. Place vial back into water bath and continue shaking.

9. At 30 min, stop the shaking, uncap and withdraw a 3-mL solution from each of the vials using a micropipette.

10. Transfer solution into a 5-mL polypropylene syringe and filter the solution through a 25-mm diameter, 1-μm porosity glass filter into a glass test tube (16×100 mm).

11. Pipette 1 mL of solution from each test tube into separate 50-mL volumetric flasks and dilute to volume with 0.1 N HCl. Mix by inverting 10 times.

12. Pass and discard a 1-mL aliquot of the sample solution through a 25-mm diameter, 1-μm porosity, glass syringe filter prior to collection of a second aliquot into a glass HPLC vial and cap.

13. Inject each sample once.

TABLE 59

Simulated nasal fluid extraction of 10/325 mg hydrocodone bitartrate/Acetaminophen tablets

| Lot | Amount extracted at 10 minutes from crushed tablets containing 10/325 mg hydrocodone bitartrate/acetaminophen | Amount extracted at 30 minutes from crushed tablets containing 10/325 mg hydrocodone bitartrate/acetaminophen |
|---|---|---|
| 1 | 14% | 45% |
| 2 | 60% | 66% |

Example 26(a): Assessment of Abuse by Multitablet Ingestion

The dosage form prepared according to Example 3 and 5 above was evaluated for multiple tablet oral abuse resistance by stirring the selected number of tablets in 300 mL of 0.1N HCl. Dissolution was performed using USP Apparatus II at 50 rpm and 37° C. One to twelve tablets were added to the vessel simultaneously and aliquots were removed after 5, 10, 15, 30, 60, 120, 240 and 360 minutes of agitation and analyzed for hydrocodone bitartrate (FIG. 4) and APAP (FIG. 5) by HPLC. The results were plotted against time and appear in FIGS. 4 and 5.

Example 26(b): Assessment of Abuse by Multitablet Ingestion

The dosage form prepared according to Example 17 above was evaluated for multiple tablet oral abuse resistance by stirring the selected number of tablets in 300 mL of 0.1N HCl. Dissolution was performed using USP Apparatus II at 50 rpm and 37° C. One to twelve tablets were added to the vessel simultaneously and aliquots were removed after 5, 10, 15, 30, 60, 120, 240 and 360 minutes of agitation and analyzed for hydrocodone bitartrate (FIG. 6) and APAP (FIG. 7) by HPLC. The results were plotted against time and appear in FIGS. 6 and 7.

Example 26(c): Assessment of Abuse by Multitablet Ingestion

The dosage form prepared according to Example 17 above was evaluated for multiple tablet oral abuse resistance by stirring the selected number of tablets in 300 mL of 0.1N HCl. Dissolution was performed using USP Apparatus II at 50 rpm and 37° C. One to twelve tablets were added to the vessel simultaneously and aliquots were removed after 5, 10, 15, 30, 60, 120, 240 and 360 minutes of agitation and analyzed for hydrocodone bitartrate and APAP by HPLC. The results were plotted against time and appear in FIG. 8 (hydrocodone bitartrate) and FIG. 9 (APAP).

Example 27: Coated Esketamine Granules

Coated esketamine granules are prepared as per the process described in Example 1 with slight variation from Example 1 in components as illustrated below.

TABLE 60

Esketamine hydrochloride granule compositions

|  | % w/w |
|---|---|
| Granulation | |
| Hypromellose | 60 |
| glyceryl behenate | 26 |
| Ethylcellulose | 14 |
| TOTAL | 100 |
| Layering | |
| esketamine hydrochloride | 5 |
| polymer granules (EC, HPMC and Compritol) | 92.5 |
| Hypromellose 2910 | 2.5 |
| TOTAL | 100 |
| Coating | |
| esketamine layered granules | 50 |
| Eudragit E-100 | 33 |
| magnesium stearate | 17 |
| TOTAL | 100 |

Example 28: Esketamine HCl Tablets

The coated granules prepared per Example 27 above are subsequently mixed with other components (carbomer, crospovidone, sodium bicarbonate, mannitol, microcrystalline cellulose) and blended in a V-blender for 30 minutes. Magnesium stearate is added to lubricate the blend and the resulting mixture was blended for additional 5 minutes prior to compressing into tablets.

TABLE 61

Esketamine hydrochloride tablet compositions

| Components mg/tab | 1 mg | 2 mg | 5 mg | 10 mg |
|---|---|---|---|---|
| Hypromellose | 11.1 | 22.2 | 55.6 | 111.2 |
| glyceryl behenate | 4.8 | 9.5 | 23.8 | 47.64 |
| Ethylcellulose | 2.6 | 5.2 | 13.1 | 26.2 |
| esketamine hydrochloride | 1 | 2 | 5 | 10 |
| Hypromellose 2910 | 0.5 | 1 | 2.5 | 5 |
| Eudragit E-100 | 13.3 | 26.7 | 66.7 | 133.4 |
| mannitol | 70 | 70 | 70 | 70 |
| carbopol | 50 | 50 | 50 | 50 |
| microcrystalline cellulose | 94 | 95 | 95 | 94 |
| Crospovidone | 90 | 90 | 95 | 150 |
| sodium bicarbonate | 30 | 30 | 30 | 30 |
| magnesium stearate | 11 | 18 | 38.6 | 74.6 |
| Total Tablet Weight | 378.3 | 419.6 | 545.3 | 802.04 |

Example 29: Coated Esketamine Granules

Coated esketamine granules are prepared as per the process described in Example 1 with slight variation from Example 1 in components as illustrated in the Table below.

TABLE 62

Esketamine hydrochloride coated granule compositions

|  | % w/w |
|---|---|
| Granulation | |
| hypromellose | 60 |
| glyceryl behenate | 26 |
| ethyl cellulose | 14 |
| TOTAL | 100 |
| Layering | |
| esketamine hydrochloride | 10 |
| polymer granules (EC, HPMC and Compritol) | 85 |
| hypromellose 2910 | 5 |
| TOTAL | 100 |
| Coating | |
| esketamine layered granules | 50 |
| Eudragit E-100 | 33 |
| magnesium stearate | 17 |
| TOTAL | 100 |

Example 30: Esketamine HCl Tablets

Coated granules prepared per Example 29 above are subsequently mixed with other components (carbomer, crospovidone, sodium bicarbonate, mannitol, microcrystalline cellulose) and blended in a V-blender for 30 minutes. Magnesium stearate is added to lubricate the blend and the resulting mixture was blended for additional 5 minutes prior to compressing into tablets.

TABLE 63

Esketamine hydrochloride tablet composition

| Components (mg/tab) | 14 mg |
|---|---|
| Hypromellose | 71.5 |
| glyceryl behenate | 30.6 |
| ethyl cellulose | 16.9 |
| esketamine hydrochloride | 14 |
| Hypromellose 2910 | 7 |
| Eudragit E-100 | 93.4 |
| mannitol | 70 |
| Carbopol | 50 |
| microcrystalline cellulose | 130 |
| Crospovidone | 150 |

TABLE 63-continued

Esketamine hydrochloride tablet composition

| Components (mg/tab) | 14 mg |
|---|---|
| sodium bicarbonate | 30 |
| magnesium stearate | 55 |
| Total Tablet Weight | 718.4 |

Example 31: Coated Esketamine Granules

Esketamine granules are manufactured using a process similar to that described in Example 1 above with some modification to the process. The active ingredient instead of being layered on the granules resides in the core where it is granulated with other excipients as per the Table below, and is subsequently coated with Eudragit E-100.
Granules are manufactured in a high shear granulator where hypromellose, Esketamine hydrochloride and glyceryl behenate are dry mixed for 3 minutes. Then a 10% hydroalcoholic solution of ethylcellulose is slowly added while maintaining the granulator impeller and chopper speed at pre-selected values that provide enough shear for granule formation and growth. Solution addition is continued until the entire amount of ethylcellulose is added. The granules are then wet milled using a size reduction mill (Granumill) and subsequently loaded into fluid bed for drying.

Esketamine hydrochloride granules are then coated in a bottom spray fluid bed coater with 25% alcoholic suspension of Eudragit E-100 copolymer and magnesium stearate (2:1). The coated granules are subsequently used in blending and compression process.

TABLE 64

Esketamine hydrochloride granule composition

| | % w/w |
|---|---|
| Granulation | |
| esketamine hydrochloride | 35 |
| hypromellose | 45 |
| glyceryl behenate | 12.5 |
| ethylcellulose | 7.5 |
| Total | 100 |
| Coating | |
| esketamine granules | 82 |
| Eudragit E-100 | 12 |
| magnesium stearate | 6 |
| TOTAL | 100 |

Example 32: Esketamine HCl Tablets

Coated granules prepared per Example 31 above are subsequently mixed with other components (carbomer, crospovidone, sodium bicarbonate, mannitol, microcrystalline cellulose) and blended in a V-blender for 30 minutes. Magnesium stearate is added to lubricate the blend and the resulting mixture was blended for additional 5 minutes prior to compressing into tablets.

TABLE 65

Esketamine hydrochloride tablet composition

| Components (mg/tablet) | 28 mg | 56 mg | 84 mg |
|---|---|---|---|
| hypromellose | 36 | 72 | 108 |
| glyceryl behenate | 10 | 20 | 30 |
| ethylcellulose | 6 | 12 | 18 |
| esketamine hydrochloride | 28 | 56 | 84 |
| Eudragit E-100 | 11.7 | 23.4 | 35.1 |
| mannitol | 17 | 17 | 20.1 |
| carbopol | 50 | 50 | 50 |
| microcrystalline cellulose | 100 | 100 | 100 |
| crospovidone | 150 | 150 | 150 |
| sodium bicarbonate | 30 | 30 | 30 |
| magnesium stearate | 12 | 20 | 30 |
| Total Tablet Weight | 450.7 | 550.4 | 655.2 |

Example 33: Coated Esketamine Granules

Esketamine granules are manufactured using a process similar to that described in Example 1 and Example 32 above with some modification to the process. The active ingredient, is granulated with other excipients per the table below, and is subsequently coated with Eudragit E-100.

Granules containing Esketamine hydrochloride are manufactured in a high shear granulator where hypromellose, esketamine hydrochloride and glyceryl behenate are dry mixed for 3 minutes. Then a 10% hydroalcoholic solution of ethylcellulose is slowly added while maintaining the granulator impeller and chopper speed at pre-selected values that provide enough shear for granule formation and growth. Solution addition is continued until the entire amount of ethylcellulose is added. The granules are then wet milled using a size reduction mill (Granumill) and then loaded into fluid bed for drying.

The granules are then coated in a bottom spray fluid bed coater with 25% alcoholic suspension of Eudragit E-100 copolymer and magnesium stearate (2:1). The resulting coated granules are subsequently used for blending and compression process.

TABLE 66

Esketamine hydrochloride granule composition

| | % w/w |
|---|---|
| Granulation | |
| esketamine hydrochloride | 72.5 |
| Hypromellose | 17.5 |
| glyceryl behenate | 5 |
| Ethylcellulose | 5 |
| TOTAL | 100 |
| Coating | |
| esketamine granules | 82 |
| Eudragit E-100 | 12 |
| magnesium stearate | 6 |
| Total | 100 |

Example 34: Esketamine HCl Tablets

The coated granules prepared per Example 33 above are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 67

Esketamine hydrochloride tablet compositions

| Components (mg/tab) | 200 mg | 300 mg | 400 mg |
|---|---|---|---|
| Hypromellose | 48 | 72 | 96.4 |
| glyceryl behenate | 14 | 21 | 27.6 |
| ethyl cellulose | 14 | 21 | 27.6 |
| esketamine hydrochloride | 200 | 300 | 400 |
| Eudragit E-100 | 40 | 61 | 81 |
| Mannitol | 25 | 25 | 25 |
| Carbopol | 75 | 75 | 75 |
| microcrystalline cellulose | 125 | 125 | 125 |
| Crospovidone | 300 | 300 | 300 |
| sodium bicarbonate | 45 | 45 | 45 |
| magnesium stearate | 140 | 150 | 160 |
| Total Tablet Weight | 1026 | 1195 | 1362.6 |

Example 35: Coated Zolpidem Granules

Coated Zolpidem tartrate granules are prepared as per the process described in Example 1 as per the composition illustrated in the Table below.

TABLE 68

Zolpidem tartrate granule compositions

|  | % w/w |
|---|---|
| Granulation |  |
| Hypromellose | 60 |
| glyceryl behenate | 26 |
| ethylcellulose | 14 |
| TOTAL | 100 |
| Layering |  |
| zolpidem tartrate | 10 |
| polymer granules (EC, HPMC and Compritol) | 85 |
| Hypromellose 2910 | 5 |
| TOTAL | 100 |
| Coating |  |
| zolpidem layered granules | 50 |
| Eudragit E-100 | 33 |
| magnesium stearate | 17 |
| TOTAL | 100 |

Example 36: Zolpidem Tartrate Tablets

Coated zolpidem granules are prepared as per the process described in Example 35 above. The coated granules are mixed with other components (carbomer, crospovidone, sodium bicarbonate, mannitol, microcrystalline cellulose and blended in a V-blender for 30 minutes. Magnesium stearate is added to lubricate the blend and blended for additional 5 minutes prior to compressing into tablets.

TABLE 69

Zolpidem tartrate tablet compositions

| Components (mg/tab) | 5 mg | 10 mg |
|---|---|---|
| hypromellose | 25.5 | 51.1 |
| glyceryl behenate | 11 | 21.9 |
| ethylcellulose | 6 | 12 |
| zolpidem tartrate | 5 | 10 |
| Hypromellose 2910 | 2.5 | 5 |
| Eudragit E-100 | 33.4 | 66.7 |
| mannitol | 70 | 70 |
| carbopol | 50 | 50 |
| microcrystalline cellulose | 95 | 94 |
| crospovidone | 100 | 100 |
| sodium bicarbonate | 30 | 30 |
| magnesium stearate | 21.6 | 39.3 |
| Total Tablet Weight | 450 | 550 |

Example 37: Coated Quetiapine Fumarate Granules

Quetiapine granules are manufactured using a process similar to that described in Example 1 above with some modification to the process. The Quetiapine fumarate, instead of being layered on the granules, resides in the core where it granulated along with other excipients per Table 70 (Granulation) and is subsequently coated with Eudragit E-100 and magnesium stearate.

Granules are manufactured in a high shear granulator where hypromellose, Quetiapine fumarate, a portion of the Lutrol, sodium lauryl sulphate and glyceryl behenate are dry mixed for 3 minutes. Then a 10% hydroalcoholic solution of ethylcellulose is slowly added while maintaining the granulator impeller and chopper speed at pre-selected values that provide enough shear for granule formation and growth. Solution addition is continued until the entire amount of ethylcellulose is added. The granules are then wet milled using a size reduction mill (Granumill) and then loaded into fluid bed for drying.

The quetiapine fumarate granules are then coated in a bottom spray fluid bed coater with alcoholic suspension of Eudragit E-100 copolymer and magnesium stearate. The resulting coated granules are then used in blending and compression process.

TABLE 70

Quetiapine fumarate coated granule composition

|  | % w/w |
|---|---|
| Granulation |  |
| quetiapine fumarate | 23.7 |
| Hypromellose | 37.6 |
| glyceryl behenate | 13.4 |
| ethyl cellulose | 8.1 |
| sodium lauryl sulphate | 9.1 |
| Lutrol | 8.1 |
| TOTAL | 100 |
| Coating |  |
| quetiapine granules | 62.5 |
| Eudragit E-100 | 25 |
| magnesium stearate | 12.5 |
| TOTAL | 100 |

Example 38: Quetiapine Fumarate Tablets

The coated granules prepared per Example 37 above are subsequently mixed with other components (carbomer, crospovidone, remaining portion of Lutrol, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 71

Quetiapine fumarate tablet compositions

| Components (mg/tablet) | 25 mg (mg/tablet) | 50 mg (mg/tablet) | 100 mg (mg/tablet) |
| --- | --- | --- | --- |
| hypromellose | 16 | 32 | 63 |
| glyceryl behenate | 9 | 18 | 36 |
| Ethylcellulose | 5 | 11 | 22 |
| quetiapine fumarate | 25 | 50 | 100 |
| Eudragit E-100 | 27 | 53 | 107 |
| Mannitol | 17 | 17 | 20.1 |
| Carbopol | 50 | 50 | 50 |
| microcrystalline cellulose | 100 | 100 | 100 |
| Crospovidone | 150 | 150 | 200 |
| sodium bicarbonate | 30 | 30 | 30 |
| magnesium stearate | 18 | 31 | 63 |
| Lutrol | 45 | 51 | 62 |
| sodium lauryl sulphate | 6 | 12 | 24 |
| Total Tablet Weight | 498 | 605 | 877.1 |

Example 39: Coated Quetiapine Granules

Quetiapine granules are manufactured using a process similar to that described in Example 1 and with some modification to the process. The Quetiapine fumarate, instead of being layered on the granules, resides in the core where it is granulated along with other excipients per Table 72 and is subsequently coated with Eudragit E-100.

Granules are manufactured in a high shear granulator where hypromellose, Quetiapine fumarate, sodium lauryl sulphate, portion of Lutrol and glyceryl behenate are dry mixed for 3 minutes. Then a 10% hydroalcoholic solution of ethylcellulose is slowly added while maintaining the granulator impeller and chopper speed at pre-selected values that provide enough shear for granule formation and growth. Solution addition is continued until the entire amount of ethylcellulose is added. The granules are then wet milled using a size reduction mill (Granumill) and then loaded into fluid bed for drying.

Quetiapine Fumarate granules are then coated in a bottom spray fluid bed coater with alcoholic suspension of Eudragit E-100 copolymer and magnesium stearate. The resultant coated granules are subsequently used for blending and compression process.

TABLE 72

Quetiapine fumarate granule compositions

| | % w/w |
| --- | --- |
| Granulation | |
| quetiapine fumarate | 14.3 |
| Hypromellose | 59.2 |
| glyceryl behenate | 4.1 |
| Ethylcellulose | 4.1 |

TABLE 72-continued

Quetiapine fumarate granule compositions

| | % w/w |
| --- | --- |
| sodium lauryl sulphate | 10.1 |
| Lutrol | 8.2 |
| TOTAL | 100 |
| Coating | |
| quetiapine granules | 82 |
| Eudragit E-100 | 12 |
| magnesium stearate | 6 |
| TOTAL | 100 |

Example 40: Quetiapine Fumarate Tablets

The coated granules prepared as per Example 39 above are subsequently mixed with other components (carbomer, crospovidone, sodium bicarbonate, mannitol, microcrystalline cellulose, and remaining portion of Lutrol) and blended in a V-blender for 30 minutes. Magnesium stearate is added to lubricate the blend and blended for additional 5 minutes prior to compressing into tablets.

TABLE 73

Quetiapine fumarate tablet compositions

| Components (mg/tab) | 200 mg | 300 mg | 400 mg |
| --- | --- | --- | --- |
| hypromellose | 48 | 72.5 | 97 |
| glyceryl behenate | 14 | 20.8 | 28 |
| ethyl cellulose | 14 | 20.8 | 28 |
| quetiapine fumarate | 200 | 300 | 400 |
| Eudragit E-100 | 40 | 74 | 99 |
| mannitol | 25 | 25 | 25 |
| carbopol | 50 | 65 | 65 |
| microcrystalline cellulose | 125 | 125 | 125 |
| crospovidone | 200 | 275 | 275 |
| sodium bicarbonate | 45 | 45 | 45 |
| magnesium stearate | 36 | 48 | 64 |
| Lutrol | 78 | 91.6 | 105 |
| sodium lauryl sulphate | 34 | 51.2 | 69 |
| Total Tablet Weight | 909 | 1213.9 | 1425 |

Example 41: Coated Hydromorphone Granules

Coated hydromorphone granules are prepared as per the process described in Example 1 with slight variation from Example 1 in components as illustrated below.

TABLE 74

Hydromorphone hydrochloride granule composition

| | % w/w |
| --- | --- |
| Granulation | |
| Hypromellose | 60 |
| glyceryl behenate | 26 |
| ethyl cellulose | 14 |
| TOTAL | 100 |

TABLE 74-continued

Hydromorphone hydrochloride granule composition

| | % w/w |
|---|---|
| Layering | |
| hydromorphone hydrochloride | 5 |
| polymer granules (EC, HPMC and Compritol) | 92.5 |
| Hypromellose 2910 | 2.5 |
| TOTAL | 100 |
| Coating | |
| hydromorphone layered granules | 50 |
| Eudragit E-100 | 33 |
| magnesium stearate | 17 |
| TOTAL | 100 |

Example 42: Hydromorphone Hydrochloride Tablets

Coated hydromorphone granules are prepared as per the process described in Example 1 and Example 41 above. The coated granules are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 75

Hydromorphone hydrochloride tablet compositions

| Components (mg/tablet) | 2 mg | 4 mg | 8 mg |
|---|---|---|---|
| hypromellose | 22.2 | 44.4 | 88.9 |
| glyceryl behenate | 9.5 | 19.1 | 38.1 |
| ethyl cellulose | 5.2 | 10.5 | 21 |
| hydromorphone hydrochloride | 2 | 4 | 8 |
| Hypromellose 2910 | 1 | 2 | 4 |
| Eudragit E-100 | 26.7 | 53.4 | 106.7 |
| mannitol | 70 | 70 | 70 |
| carbopol | 50 | 50 | 50 |
| microcrystalline cellulose | 95 | 95 | 94 |
| crospovidone | 90 | 95 | 150 |
| sodium bicarbonate | 30 | 30 | 30 |
| magnesium stearate | 18.1 | 58.3 | 60.4 |
| Total Tablet Weight | 419.7 | 531.7 | 721.1 |

Example 43: Coated Methamphetamine Granules

Coated methamphetamine granules are prepared according to the process described in Example 1.

TABLE 76

Methamphetamine hydrochloride granule composition

| | % w/w |
|---|---|
| Granulation | |
| Hypromellose | 60 |
| glyceryl behenate | 26 |
| ethyl cellulose | 14 |
| TOTAL | 100 |

TABLE 76-continued

Methamphetamine hydrochloride granule composition

| | % w/w |
|---|---|
| Layering | |
| methamphetamine hydrochloride | 5 |
| polymer granules (EC, HPMC and Compritol) | 92.5 |
| Hypromellose 2910 | 2.5 |
| TOTAL | 100 |
| Coating | |
| methamphetamine layered granules | 50 |
| Eudragit E-100 | 33 |
| magnesium stearate | 17 |
| TOTAL | 100 |

Example 44: Methamphetamine Hydrochloride Tablets

Coated methamphetamine granules are prepared as per the process described in Example 1 and Example 43 above. The coated granules are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 77

Methamphetamine hydrochloride tablet composition

| Components (mg/tablet) | 5 mg |
|---|---|
| hypromellose | 55.6 |
| glyceryl behenate | 23.8 |
| ethyl cellulose | 13.1 |
| methamphetamine hydrochloride | 5 |
| Hypromellose 2910 | 2.5 |
| Eudragit E-100 | 66.7 |
| mannitol | 70 |
| Carbopol | 50 |
| microcrystalline cellulose | 95 |
| Crospovidone | 100 |
| sodium bicarbonate | 30 |
| magnesium stearate | 39 |
| Total Tablet Weight | 550.7 |

Example 45: Coated Oxymorphone Granules

Coated oxymorphone granules are prepared as per the process described in Example 1.

TABLE 78

Oxymorphone hydrochloride granule composition

| | % w/w |
|---|---|
| Granulation | |
| Hypromellose | 60 |
| glyceryl behenate | 26 |
| ethyl cellulose | 14 |
| TOTAL | 100 |

TABLE 78-continued

Oxymorphone hydrochloride granule composition

|  | % w/w |
|---|---|
| Layering | |
| oxymorphone hydrochloride | 10 |
| polymer granules (EC, HPMC and Compritol) | 85 |
| Hypromellose 2910 | 5 |
| TOTAL | 100 |
| Coating | |
| oxymorphone layered granules | 50 |
| Eudragit E-100 | 33 |
| magnesium stearate | 17 |
| TOTAL | 100 |

Example 46: Oxymorphone Hydrochloride Tablets

Coated oxymorphone granules are prepared as per the process described in Example 1 and Example 45 above. The coated granules are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 79

Oxymorphone hydrochloride tablet compositions

| Components (mg/tablet) | 5 mg | 10 mg |
|---|---|---|
| Hypromellose | 25.5 | 51.1 |
| glyceryl behenate | 11 | 21.9 |
| ethyl cellulose | 6 | 12 |
| oxymorphone hydrochloride | 5 | 10 |
| Hypromellose 2910 | 2.5 | 5 |
| Eudragit E-100 | 33.4 | 66.7 |
| Mannitol | 70 | 70 |
| carbopol | 45 | 45 |
| microcrystalline cellulose | 95 | 94 |
| Crospovidone | 100 | 100 |
| sodium bicarbonate | 27 | 27 |
| magnesium stearate | 21.6 | 39.3 |
| Total Tablet Weight | 442 | 542 |

Example 47: Coated Oxycodone Granules

Coated oxycodone granules are prepared as per the process described in Example 1.

The composition for the coated oxycodone granules is provided in Table 80 below.

TABLE 80

Oxycodone hydrochloride granule composition

|  | % w/w |
|---|---|
| Granulation | |
| Hypromellose | 60 |
| glyceryl behenate | 26 |
| Ethylcellulose | 14 |
| TOTAL | 100 |

TABLE 80-continued

Oxycodone hydrochloride granule composition

|  | % w/w |
|---|---|
| Layering | |
| oxycodone hydrochloride | 10 |
| polymer granules (EC, HPMC and Compritol) | 85 |
| Hypromellose 2910 | 5 |
| TOTAL | 100 |
| Coating | |
| oxycodone layered granules | 50 |
| Eudragit E-100 | 33 |
| magnesium stearate | 17 |
| TOTAL | 100 |

Example 48: Oxycodone Hydrochloride Tablets

Coated oxycodone granules are prepared as per the process described in Example 1 and Example 47 above. The coated granules are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 81

Oxycodone hydrochloride tablet compositions

| Components (mg/tablet) | 5 mg | 15 mg | 30 mg |
|---|---|---|---|
| hypromellose | 25.5 | 76.6 | 153.3 |
| glyceryl behenate | 11 | 32.8 | 65.7 |
| ethyl cellulose | 6 | 18.1 | 36.1 |
| oxycodone hydrochloride | 5 | 15 | 30 |
| Hypromellose 2910 | 2.5 | 7.5 | 15 |
| Eudragit E-100 | 33.4 | 100.1 | 200.1 |
| mannitol | 70 | 37.29 | 70 |
| carbopol | 45 | 50 | 50 |
| microcrystalline cellulose | 95 | 130 | 94 |
| crospovidone | 100 | 150 | 200 |
| sodium bicarbonate | 27 | 30 | 30 |
| magnesium stearate | 21.6 | 57 | 110 |
| Total Tablet Weight | 442 | 704.39 | 1054.2 |

Example 49: Coated Morphine Sulphate Granules

Coated morphine granules are prepared as per the process described in Example 1.

TABLE 82

Morphine Sulfate tablet compositions

|  | % w/w |
|---|---|
| Granulation | |
| hypromellose | 60 |
| glyceryl behenate | 26 |
| ethyl cellulose | 14 |
| TOTAL | 100 |

TABLE 82-continued

Morphine Sulfate tablet compositions

|  | % w/w |
|---|---|
| Layering | |
| morphine sulphate | 10 |
| polymer granules (EC, HPMC and Compritol) | 85 |
| Hypromellose 2910 | 5 |
| TOTAL | 100 |
| Coating | |
| morphine layered granules | 50 |
| Eudragit E-100 | 33 |
| magnesium stearate | 17 |
| TOTAL | 100 |

Example 50: Morphine Sulphate Tablets

Coated morphine granules are prepared as per the process described in Example 1 and Example 49 above. The coated granules are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 83

Morphine sulphate tablet compositions

| Components (mg/tablet) | 6 mg | 15 mg | 30 mg |
|---|---|---|---|
| hypromellose | 30.6 | 76.6 | 153.3 |
| glyceryl behenate | 13.1 | 32.8 | 65.7 |
| ethyl cellulose | 7.2 | 18.1 | 36.1 |
| morphine sulphate | 6 | 15 | 30 |
| Hypromellose 2910 | 3 | 7.5 | 15 |
| Eudragit E-100 | 40.02 | 100.1 | 200.1 |
| mannitol | 70 | 70 | 70 |
| carbopol | 45 | 50 | 50 |
| microcrystalline cellulose | 95 | 130 | 94 |
| Crospovidone | 100 | 150 | 200 |
| sodium bicarbonate | 27 | 30 | 30 |
| magnesium stearate | 24.5 | 57 | 110 |
| Total Tablet Weight | 461.42 | 737.1 | 1054.2 |

Example 51: Coated Mixed Amphetamine Salts Granules

Coated granules containing mixed amphetamine salts (dextroamphetamine saccharate, amphetamine aspartate, dextroamphetamine sulfate, amphetamine sulfate) are prepared as per the process described in Example 1.

TABLE 84

Mixed amphetamine salt granule formulation

|  | % w/w |
|---|---|
| Granulation | |
| Hypromellose | 60 |
| glyceryl behenate | 26 |
| ethyl cellulose | 14 |
| TOTAL | 100 |
| Layering | |
| Mixed amphetamine salts (*Dextroamphetamine saccharate, amphetamine aspartate) | 10 |
| polymer granules (EC, HPMC and Compritol) | 85 |
| Hypromellose 2910 | 5 |
| TOTAL | 100 |
| Coating | |
| mixed amphetamine salt layered granules | 50 |
| Eudragit E-100 | 33 |
| magnesium stearate | 17 |
| TOTAL | 100 |

Example 52: Mixed Amphetamine Salt Tablets

Coated granules containing mixed amphetamine salts are prepared as per the process described in Example 1 and Example 51 above. The coated granules are subsequently mixed with other components such as carbomer, crospovidone, sodium bicarbonate, mannitol, microcrystalline cellulose and blended in a V-blender for 30 minutes. Magnesium stearate is added to lubricate the blend and blended for additional 5 minutes prior to compressing into tablets.

TABLE 85

Mixed amphetamine salt tablet formulation

| | Total Amphetamine/Base Equivalence | | | | | | |
|---|---|---|---|---|---|---|---|
| Components (mg/tablet) | 3.13 mg / 5 mg | 4.7 mg / 7.5 mg | 6.3 mg / 10 mg | 7.8 mg / 12.5 mg | 9.4 mg / 15 mg | 12.6 mg / 20 mg | 18.8 mg / 30 mg |
| hypromellose | 25.5 | 38.3 | 51.1 | 63.8 | 76.6 | 102.15 | 153.3 |
| glyceryl behenate | 10.9 | 16.4 | 21.9 | 27.4 | 32.8 | 43.8 | 65.7 |
| ethyl cellulose | 6.02 | 9.03 | 12.04 | 15.05 | 18.1 | 24.1 | 36.1 |
| Mixed amphetamine salts* | 5 | 7.5 | 10 | 12.5 | 15 | 20 | 30 |
| Hypromellose 2910 | 2.5 | 3.75 | 5 | 6.25 | 7.5 | 10 | 15 |
| Eudragit E-100 | 33.4 | 50.04 | 66.7 | 83.4 | 100.1 | 133.4 | 200.1 |
| mannitol | 70 | 70 | 70 | 70 | 70 | 70 | 70 |
| carbopol | 45 | 45 | 45 | 50 | 50 | 50 | 50 |
| microcrystalline cellulose | 95 | 95 | 95 | 130 | 130 | 130 | 150 |

TABLE 85-continued

Mixed amphetamine salt tablet formulation

| Components (mg/tablet) | Total Amphetamine/Base Equivalence | | | | | | |
|---|---|---|---|---|---|---|---|
| | 3.13 mg 5 mg | 4.7 mg 7.5 mg | 6.3 mg 10 mg | 7.8 mg 12.5 mg | 9.4 mg 15 mg | 12.6 mg 20 mg | 18.8 mg 30 mg |
| crospovidone | 100 | 100 | 100 | 150 | 150 | 160 | 200 |
| sodium bicarbonate | 27 | 27 | 27 | 30 | 30 | 30 | 30 |
| magnesium stearate | 21.5 | 30 | 38.6 | 48 | 57 | 75 | 110 |
| Total Tablet Weight | 441.82 | 492.02 | 542.34 | 686.4 | 737.1 | 848.45 | 1110.2 |

*dextroamphetamine saccharate, amphetamine aspartate monohydrate equivalent, dextroamphetamine sulfate, amphetamine sulfate.

Example 53: Codeine Phosphate Granules

Coated granules containing Codeine phosphate are prepared as per the process described in Example 1 with some modifications to the composition as described below.

TABLE 86

Codeine phosphate granule formulation

| | % w/w |
|---|---|
| Granulation | |
| Hypromellose | 60 |
| glyceryl behenate | 26 |
| ethyl cellulose | 14 |
| TOTAL | 100 |
| Layering | |
| codeine phosphate. | 20 |
| polymer Granules (EC, HPMC and Compritol) | 70 |
| Hypromellose 2910 | 10 |
| TOTAL | 100 |
| Coating | |
| codeine phosphate layered granules | 70 |
| Eudragit E-100 | 20 |
| magnesium stearate | 10 |
| TOTAL | 100 |

Example 54: Codeine Phosphate Tablets

Coated granules containing codeine phosphate are prepared as per the process described in Example 1 and Example 53 above. The coated granules are subsequently mixed with other active ingredient (paracetamol), and other components (carbomer, crospovidone, sodium bicarbonate, mannitol, colorant, microcrystalline cellulose), and blended in a V-blender for 30 minutes. Magnesium stearate is added to lubricate the blend and blended for additional 5 minutes prior to compressing into tablets.

TABLE 87

Codeine phosphate/APAP tablet formulation

| Components (mg/tablet) | 30/300 mg | 60/300 mg |
|---|---|---|
| hypromellose | 63.1 | 126.2 |
| glyceryl behenate | 27 | 54.1 |
| ethyl cellulose | 14.9 | 29.7 |
| codeine phosphate | 30 | 60 |

TABLE 87-continued

Codeine phosphate/APAP tablet formulation

| Components (mg/tablet) | 30/300 mg | 60/300 mg |
|---|---|---|
| Hypromellose 2910 | 15 | 30 |
| Eudragit E-100 | 42.9 | 85.7 |
| paracetamol* | 315.8 | 315.8 |
| mannitol | 29.4 | 29.4 |
| Carbopol | 50 | 50 |
| microcrystalline cellulose | 180 | 180 |
| Crospovidone | 200 | 200 |
| sodium bicarbonate | 30 | 30 |
| FD&C blue # 2 | NA | 0.6 |
| Iron Oxide Yellow 510P | 0.5 | NA |
| magnesium stearate | 31.5 | 57 |
| Total Tablet Weight | 1030.1 | 1248.5 |

*The paracetamol grade Contains 300 mg of APAP and 15.8 mg of gelatin

Example 55: Methylphenidate Hydrochloride Granules

Coated granules containing methylphenidate hydrochloride are prepared as per the process described in Example 1.

TABLE 88

Methylphenidate hydrochloride granule formulation

| | % w/w |
|---|---|
| Granulation | |
| Hypromellose | 60 |
| glyceryl behenate | 26 |
| ethyl cellulose | 14 |
| TOTAL | 100 |
| Layering | |
| methylphenidate hydrochloride | 10 |
| polymer granules (EC, HPMC and Compritol) | 85 |
| Hypromellose 2910 | 5 |
| TOTAL | 100 |
| Coating | |
| methylphenidate hydrochloride layered granules | 50 |
| Eudragit E-100 | 33 |
| magnesium stearate | 17 |
| TOTAL | 100 |

Example 56: Methylphenidate Hydrochloride Tablets

Coated granules containing methylphenidate hydrochloride are prepared as per the process described in Example 1 and Example 55 above. The coated granules are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 89

Methylphenidate hydrochloride tablet formulation

| Components (mg/tablet) | 5 mg | 20 mg |
|---|---|---|
| hypromellose | 25.5 | 102.15 |
| glyceryl behenate | 10.9 | 43.8 |
| ethyl cellulose | 6.02 | 24.1 |
| methylphenidate hydrochloride | 5 | 20 |
| Hypromellose 2910 | 2.5 | 10 |
| Eudragit E-100 | 33.4 | 133.4 |
| Mannitol | 70 | 70 |
| Carbopol | 45 | 50 |
| microcrystalline cellulose | 95 | 150 |
| Crospovidone | 100 | 160 |
| sodium bicarbonate | 27 | 30 |
| magnesium stearate | 21.5 | 75 |
| Total Tablet Weight | 441.82 | 868.45 |

Example 57: Oxycodone Hydrochloride Granules

Coated granules containing oxycodone hydrochloride were prepared and coated as per the process described in Example 1.

TABLE 90

Oxycodone hydrochloride granule formulation

| | % w/w |
|---|---|
| Granulation | |
| Hypromellose | 60 |
| glyceryl behenate | 26 |
| ethyl cellulose | 14 |
| TOTAL | 100 |
| Layering | |
| oxycodone hydrochloride | 10 |
| polymer granules (EC, HPMC and Compritol) | 85 |
| Hypromellose 2910 | 5 |
| TOTAL | 100 |
| Coating | |
| oxycodone layered granules, 10% | 50 |
| Eudragit E-100 | 33 |
| magnesium stearate | 17 |
| TOTAL | 100 |

Granules were manufactured in a high shear granulator where Hypromellose and glyceryl behenate were dry mixed for 3 minutes. Then a 10% hydroalcoholic solution of ethylcellulose N10 was slowly added while maintaining the granulator impeller and chopper speed at pre-selected values that provide enough shear for granule formation and growth. Solution addition was continued until the entire amount of ethylcellulose was added. The granules were then wet milled using a size reduction mill (Granumill) and were subsequently loaded into fluid bed for drying. The prepared granules were then layered in a bottom spray fluid bed coater with a 12% aqueous solution of oxycodone hydrochloride and HPMC 2910 (2:1).

The oxycodone hydrochloride layered granules were then coated in a bottom spray fluid bed coater with 25% alcoholic suspension of Eudragit E-100 copolymer and magnesium stearate (2:1). The resulting coated granules were subsequently used for further blending and compression process.

Example 58: Oxycodone/Acetaminophen Tablets

The coated granules prepared according to the example 57 above were mixed with another active agent, Paracetamol, and other excipients (carbomer, crospovidone, sodium bicarbonate, mannitol, FD&C blue, microcrystalline cellulose), and blended in a V-blender for 30 minutes. Magnesium stearate was then added to lubricate the blend and blended for additional 5 minutes prior to compressing into oxycodone/APAP tablets.

TABLE 91

Oxycodone hydrochloride tablet formulation

| Component | % w/w |
|---|---|
| oxycodone coated granules | 20.0 |
| paracetamol* | 33.7 |
| Mannitol | 4.2 |
| carbopol | 5.0 |
| microcrystalline cellulose | 13.0 |
| Crospovidone | 20.0 |
| sodium bicarbonate | 3.0 |
| FD&C blue | 0.06 |
| magnesium stearate | 1.0 |
| Total | 100 |

*Contains 95% acetaminophen and 5% gelatin

Example 59: Oxycodone/Acetaminophen Tablets

The coated granules prepared according to the example 57 above were mixed with another active agent, Paracetamol, and other excipients (carbomer, crospovidone, sodium bicarbonate, mannitol, FD&C blue, microcrystalline cellulose), and blended in a V-blender for 30 minutes. Magnesium stearate was then added to lubricate the blend and blended for additional 5 minutes prior to compressing into oxycodone/APAP tablets.

TABLE 92

Oxycodone/acetaminophen tablet formulations

| Component (% w/w) | 5/325 mg | 7.5/325 mg | 10/325 mg |
|---|---|---|---|
| oxycodone coated granules | 12.5 | 16.7 | 20.0 |
| paracetamol* | 42.8 | 38.0 | 34.2 |
| Mannitol | 3.7 | 4.37 | 3.79 |
| carbopol | 6.25 | 5.6 | 5 |
| microcrystalline cellulose | 12 | 12 | 13 |
| Crospovidone | 18 | 19 | 20 |
| sodium bicarbonate | 3.75 | 3.3 | 3 |
| Iron Oxide yellow | 0.06 | NA | NA |

TABLE 92-continued

Oxycodone/acetaminophen tablet formulations

| Component (% w/w) | 5/325 mg | 7.5/325 mg | 10/325 mg |
|---|---|---|---|
| FD&C Blue # 2 | NA | 0.06 | NA |
| magnesium stearate | 1.0 | 1.0 | 1.0 |
| Total | 100 | 100 | 100 |

*Contains 95% acetaminophen and 5% gelatin

Example 60: Armodafinil Granules

Armodafinil granules are manufactured using a process similar to that described in Example 1 and with some modification to the process. The active ingredient, Armodafinil, instead of being layered on the granules, resides in the core where it is granulated along with other excipients as per Table 93, and is subsequently coated with Eudragit E-100.

Granules are manufactured in a high shear granulator where hypromellose, Armodafinil, povidone and glyceryl behenate are dry mixed for 3 minutes. Then a 10% hydroalcoholic solution of ethylcellulose is slowly added while maintaining the granulator impeller and chopper speed at pre-selected values that provide enough shear for granule formation and growth. Solution addition is continued until the entire amount of ethylcellulose is added. The granules are then wet milled using a size reduction mill (Granumill) and subsequently loaded into fluid bed for drying.

Armodafinil granules are then coated in a bottom spray fluid bed coater with alcoholic suspension of Eudragit E-100 copolymer and magnesium stearate. The resultant coated granules are subsequently used for blending and compression process.

TABLE 93

Armodafinil granule formulations

| | % w/w |
|---|---|
| Granulation | |
| Armodafinil | 66.99 |
| Hypromellose | 16.75 |
| glyceryl behenate | 3.83 |
| ethyl cellulose | 3.83 |
| Povidone | 8.61 |
| TOTAL | 100 |
| Coating | |
| armodafinil granules | 70 |
| Eudragit E-100 | 20 |
| magnesium stearate | 10 |
| TOTAL | 100 |

Example 61: Armodafinil Tablets

The coated granules prepared as per Example 60 above are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 94

Armodafinil tablet formulations

| Components (mg/tablet) | 50 mg (mg/tablet) | 150 mg (mg/tablet) | 200 mg (mg/tablet) |
|---|---|---|---|
| hypromellose | 12.5 | 37.5 | 50 |
| glyceryl behenate | 2.9 | 8.6 | 11 |
| ethyl cellulose | 2.9 | 8.6 | 11 |
| armodafinil | 50 | 150 | 200 |
| Eudragit E-100 | 21.3 | 64 | 85 |
| mannitol | 17 | 25 | 25 |
| carbopol | 50 | 50 | 50 |
| microcrystalline cellulose | 100 | 125 | 125 |
| crospovidone | 150 | 200 | 200 |
| sodium bicarbonate | 30 | 30 | 30 |
| magnesium stearate | 16 | 40 | 52 |
| povidone | 6.4 | 19.3 | 26 |
| Total Tablet Weight | 459 | 758 | 865 |

Example 62: Phenobarbital Granules

Phenobarbital granules are manufactured using a process similar to that described in Example 1 and with some modification to the process. The active ingredient, Phenobarbital, instead of being layered on the granules, resides in the core where it is granulated along with other excipients per the Table below, and is subsequently coated with Eudragit E-100.

Granules are manufactured in a high shear granulator where hypromellose, phenobarbital, povidone and glyceryl behenate are dry mixed for 3 minutes. Then a 10% hydroalcoholic solution of ethylcellulose is slowly added while maintaining the granulator impeller and chopper speed at pre-selected values that provide enough shear for granule formation and growth. Solution addition is continued until the entire amount of ethylcellulose is added. The granules are then wet milled using a size reduction mill (Granumill) and subsequently loaded into fluid bed for drying.

The phenobarbital granules are then coated in a bottom spray fluid bed coater with alcoholic suspension of Eudragit E-100 copolymer and magnesium stearate. The resultant coated granules are subsequently used for blending and compression process.

TABLE 95

Phenobarbital granule formulations

| | % w/w |
|---|---|
| Granulation | |
| Phenobarbital | 66.99 |
| Hypromellose | 16.75 |
| glyceryl behenate | 3.83 |
| ethyl cellulose | 3.83 |
| Povidone | 8.61 |
| TOTAL | 100 |
| Layering | |
| phenobarbital granules | 50 |
| Eudragit E-100 | 33 |
| magnesium stearate | 17 |
| TOTAL | 100 |

Example 63: Phenobarbital Tablets

The coated granules prepared as per Example 62 above are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 96

Phenobarbital tablet formulations

| Components | 15 mg (mg/tablet) | 30 mg (mg/tablet) | 60 mg (mg/tablet) | 100 mg (mg/tablet) |
|---|---|---|---|---|
| hypromellose | 3.8 | 7.5 | 15 | 25.01 |
| glyceryl behenate | 1 | 2 | 3.4 | 5.72 |
| ethyl cellulose | 1 | 2 | 3.4 | 5.72 |
| phenobarbital | 15 | 30 | 60 | 100 |
| Eudragit E-100 | 15 | 30 | 59 | 98.5 |
| mannitol | 20 | 20 | 20 | 20 |
| carbopol | 50 | 50 | 50 | 50 |
| microcrystalline cellulose | 75 | 100 | 100 | 100 |
| crospovidone | 130 | 130 | 200 | 200 |
| sodium bicarbonate | 30 | 30 | 30 | 30 |
| magnesium stearate | 12 | 20 | 36 | 59 |
| povidone | 2 | 4 | 7.7 | 12.9 |
| Total Tablet Weight | 354.8 | 425.5 | 584.5 | 706.85 |

Example 64: Diazepam Granules

Coated diazepam granules are prepared as per the process described in Example 1 with slight variation from Example 1 in components as illustrated in the Table below.

TABLE 97

Diazepam granule formulations

| | % w/w |
|---|---|
| Granulation | |
| Hypromellose | 60 |
| glyceryl behenate | 26 |
| ethyl cellulose | 14 |
| TOTAL | 100 |
| Layering | |
| diazepam | 5 |
| polymer granules (EC, HPMC and Compritol) | 92.5 |
| Hypromellose 2910 | 2.5 |
| TOTAL | 100 |
| Coating | |
| diazepam layered granules | 50 |
| Eudragit E-100 | 33 |
| magnesium stearate | 17 |
| TOTAL | 100 |

Example 65: Diazepam Tablets

Coated diazepam granules are prepared as per the process described in Example 1 and Example 64 above. The coated granules are subsequently mixed with other components (carbomer, crospovidone, sodium bicarbonate, mannitol, microcrystalline cellulose), and blended in a V-blender for 30 minutes. Magnesium stearate is added to lubricate the blend and blended for additional 5 minutes prior to compressing into tablets.

TABLE 98

Diazepam tablet formulations

| Components (mg/tablet) | 2 mg | 5 mg | 10 mg |
|---|---|---|---|
| Hypromellose | 22.2 | 55.6 | 111.2 |
| glyceryl behenate | 9.5 | 23.8 | 47.64 |
| ethyl cellulose | 5.2 | 13.1 | 26.2 |
| Diazepam | 2 | 5 | 10 |
| Hypromellose 2910 | 1 | 2.5 | 5 |
| Eudragit E-100 | 26.7 | 66.7 | 133.4 |
| mannitol | 70 | 70 | 70 |
| carbopol | 50 | 50 | 50 |
| microcrystalline cellulose | 95 | 95 | 94 |
| Crospovidone | 120 | 120 | 150 |
| sodium bicarbonate | 30 | 30 | 30 |
| magnesium stearate | 18.1 | 38.6 | 74.6 |
| Total Tablet Weight | 449.7 | 570.3 | 802.04 |

Example 66: Hydrocodone Bitartrate Granules

Coated granules containing hydrocodone bitartrate are prepared as per the process described in Example 1.

TABLE 99

Hydrocodone bitartrate granule formulations

| | % w/w |
|---|---|
| Granulation | |
| Hypromellose | 60 |
| glyceryl behenate | 26 |
| ethyl cellulose | 14 |
| TOTAL | 100 |
| Layering | |
| hydrocodone bitartrate | 10 |
| polymer granules (EC, HPMC and Compritol) | 85 |
| Hypromellose 2910 | 5 |
| TOTAL | 100 |
| Coating | |
| hydrocodone bitartrate layered granules | 50 |
| Eudragit E-100 | 33 |
| magnesium stearate | 17 |
| TOTAL | 100 |

Example 67: Hydrocodone Bitartrate Tablets

Coated granules containing hydrocodone bitartrate are prepared as per the process described in Example 1 and Example 66 above. The coated granules are subsequently mixed with other components (carbomer, crospovidone, sodium bicarbonate, mannitol, microcrystalline cellulose) and blended in a V-blender for 30 minutes. Magnesium stearate is added to lubricate the blend and blended for additional 5 minutes prior to compressing into tablets.

TABLE 100

Hydrocodone Tablet Formulations

| Components | 5 mg (mg/tablet) | 10 mg (mg/tablet) |
|---|---|---|
| hypromellose | 25.5 | 51.1 |
| glyceryl behenate | 11 | 21.9 |
| ethyl cellulose | 6 | 12.04 |
| hydrocodone bitartrate | 5 | 10 |
| Hypromellose 2910 | 2.5 | 5 |
| Eudragit E-100 | 33.4 | 66.7 |
| Mannitol | 70 | 70 |
| Carbopol | 50 | 50 |
| microcrystalline cellulose | 95 | 95 |
| Crospovidone | 100 | 120 |
| sodium bicarbonate | 30 | 30 |
| magnesium stearate | 21.6 | 39.3 |
| Total Tablet Weight | 450 | 571.04 |

Example 68: Oxycodone Hydrochloride Coated Granules

TABLE 201

Granule Formulation

| Component | % w/w |
|---|---|
| Hypromellose K100M | 60 |
| glyceryl behenate | 26 |
| ethyl cellulose (10 cps) | 14 |
| TOTAL | 100 |

TABLE 102

Layered Granule Formulation

| Component | % w/w |
|---|---|
| oxycodone hydrochloride | 10 |
| polymer granules (EC, HPMC and Compritol) | 85 |
| Hypromellose 2910 E3 | 5 |
| TOTAL | 100 |

TABLE 103

Coated Granules Formulation

| Component | % w/w |
|---|---|
| oxycodone hydrochloride layered granules, 10% | 50 |
| Eudragit E-100 | 33 |
| magnesium stearate | 17 |
| TOTAL | 100 |

Granules were manufactured in a high shear granulator, where hypromellose, glyceryl behenate, and a portion (67%) of the ethylcellulose were dry mixed for 3 minutes. Then, a hydroalcoholic (~28 parts of water and ~72 parts of alcohol) solution of ethylcellulose (10% wt/wt) was slowly added while maintaining the granulator impeller and chopper speed at pre-selected values that provide enough shear for granule formation and growth. Solution addition was continued until the entire amount of ethylcellulose was added. The granules were then wet milled using a size reduction mill (Granumill) and were subsequently loaded into fluid bed for drying.

The prepared granules were then layered in a bottom spray fluid bed coater with a 12% wt/wt aqueous solution of oxycodone hydrochloride and HPMC.

The oxycodone bitartrate layered granules were then coated in a bottom spray fluid bed coater with 25% alcoholic suspension of Eudragit E-100 copolymer and magnesium stearate. The resulting coated granules were subsequently blended for homogeneity and used for further blending and compression process.

Example 69: Oxycodone Acetaminophen Tablet Formation

Coated granules were prepared according to the Example 68 above, and mixed with Paracetamol (manufactured using acetaminophen and gelatin) and other excipients (as listed in Table 104 below), and blended for approximately 270 revolutions. Magnesium stearate was then added to lubricate the blend and blended for additional 45 revolutions. The blend was then compressed into oxycodone/acetaminophen tablets.

TABLE 104

Tablet Formulation

| Component | % w/w | mg/tablet |
|---|---|---|
| Oxycodone hydrochloride coated granules, 5% | 20.0 | 200 |
| Paracetamol | 33.7 | 337* |
| Mannitol | 10.3 | 103 |
| Carbopol | 5.0 | 50 |
| microcrystalline cellulose | 12.0 | 120 |
| Crospovidone | 15.0 | 150 |
| sodium bicarbonate | 3.0 | 30 |
| magnesium stearate | 1.0 | 10 |
| Total | 100 | 1000 |

*contains 325 mg of acetaminophen

Example 70: Coated Oxycodone Granules, 5%

Granules were prepared, layered with API and subsequently coated. These coated particles were then blended with other components and compressed into tablets.

TABLE 305

Granules Formulation

| Component | % w/w |
|---|---|
| Hypromellose K100M | 60 |
| Glyceryl behenate | 26 |
| Ethyl cellulose (10 cP) | 14 |
| TOTAL | 100 |

TABLE 106

Layered Granules Formulation

| Component | % w/w |
|---|---|
| Oxycodone Hydrochloride | 10 |
| Polymer granules (EC, HPMC and Compritol) | 85 |
| Hypromellose 2910 (HPMC 2910 E3) | 5 |
| TOTAL | 100 |

TABLE 107

Coated Granules Formulation

| Component | % w/w |
|---|---|
| Oxycodone hydrochloride layered granules, 10% | 50 |
| Eudragit E-100 | 33 |
| Magnesium stearate | 17 |
| TOTAL | 100 |

Granules were manufactured in a high shear granulator, where hypromellose, a portion of ethyl cellulose and glyceryl behenate were dry mixed for 3 minutes. Then a 10% w/w hydroalcoholic (~28 parts of water and ~72 parts of ethanol) solution of ethyl cellulose 10 cP was slowly added while maintaining the granulator impeller and chopper speed at pre-selected values that provide enough shear for granule formation and growth. Solution addition was continued until the entire amount of ethyl cellulose was added. The granules were then wet milled using a size reduction mill (Granumill) and were subsequently loaded into fluid bed for drying.

The prepared granules were then layered in a bottom spray fluid bed coater with a 12% w/w aqueous solution of oxycodone hydrochloride and HPMC 2910 E3.

The oxycodone hydrochloride layered granules were then coated in a bottom spray fluid bed coater with 25% alcoholic suspension of Eudragit E-100 copolymer and magnesium stearate. The resulting coated granules were subsequently blended for homogeneity and used for further blending and compression process.

Example 71: Coated Polymer Granules

Granules were manufactured in a high shear granulator, where hypromellose, a portion of ethyl cellulose and glyceryl behenate were dry mixed for 3 minutes. Then a 10% w/w hydroalcoholic (~28 parts of water and ~72 parts of ethanol) solution of ethyl cellulose 10 cP was slowly added while maintaining the granulator impeller and chopper speed at pre-selected values that provide enough shear for granule formation and growth. Solution addition was continued until the entire amount of ethyl cellulose was added. The granules were then wet milled using a size reduction mill (Granumill) and were subsequently loaded into fluid bed for drying.

The granules were then coated in a bottom spray fluid bed coater with 25% alcoholic suspension of Eudragit E-100 copolymer and magnesium stearate.

TABLE 108

Granules Formulation

| Component | % w/w |
|---|---|
| Hypromellose K100M | 60 |
| Glyceryl behenate | 26 |
| Ethyl cellulose (10 cP) | 14 |
| TOTAL | 100 |

TABLE 109

Coated Polymer Granules Formulation

| Component | % w/w |
|---|---|
| Polymer granules | 50 |
| Eudragit E-100 | 33 |
| Magnesium stearate | 17 |
| TOTAL | 100 |

Example 72A and Example 72B

The oxycodone hydrochloride coated granules were prepared according to the Example 70 and mixed with coated polymer granules prepared according to Example 71. Another active agent i.e. Paracetamol (manufactured using acetaminophen and gelatin) and other excipients such as carbomer, crospovidone, sodium bicarbonate, mannitol and microcrystalline cellulose were added and blended for approximately 270 revolutions. Magnesium stearate was then added to lubricate the blend and blended for additional 45 revolutions prior to compressing into oxycodone/acetaminophen tablets.

TABLE 110

Tablet Formulation

| | Example 72A | | Example 72B | |
|---|---|---|---|---|
| Component | % w/w | mg/tablet | % w/w | mg/tablet |
| Oxycodone hydrochloride coated granules, 5% | 10.87 | 108.7 | 16.3 | 163 |
| Coated Polymer granules | 9.13 | 91.3 | 3.7 | 37 |
| Paracetamol | 33.7 | 337* | 33.71 | 337.1* |
| Mannitol | 4.29 | 42.9 | 4.29 | 42.9 |
| Carbopol | 5.0 | 50.0 | 5.0 | 50 |
| Microcrystalline cellulose | 13.0 | 130.0 | 13.0 | 130 |
| Crospovidone | 20.0 | 200. | 20.0 | 200 |
| Sodium bicarbonate | 3.0 | 30 | 3.0 | 30 |
| Magnesium stearate | 1.0 | 10 | 1.0 | 10 |
| Total | 100 | 1000 | 100 | 1000 |

*contains 325 mg of acetaminophen

Example 73: In Vitro Analysis of Multiple Tablet Oral Abuse Resistance

Figure 10:
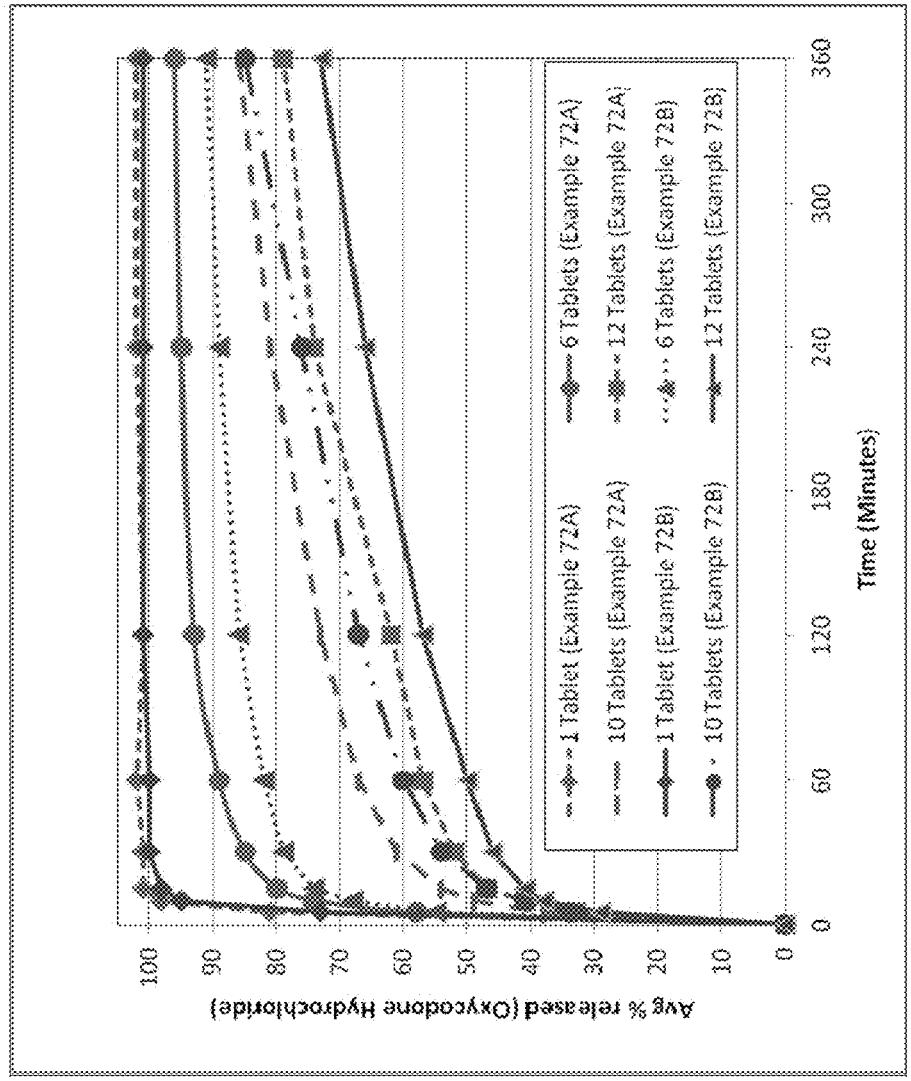
FIG. 10 shows a plot of multiple tablet oral abuse resistance (supratherapeutic dosing)—dissolution of oxycodone hydrochloride from oxycodone hydrochloride/acetaminophen tablets (5/325 mg/tablet and 7.5/325 mg/tablet of oxycodone hydrochloride/acetaminophen) in 0.1N HCl media as a function of time.
Figure 11:
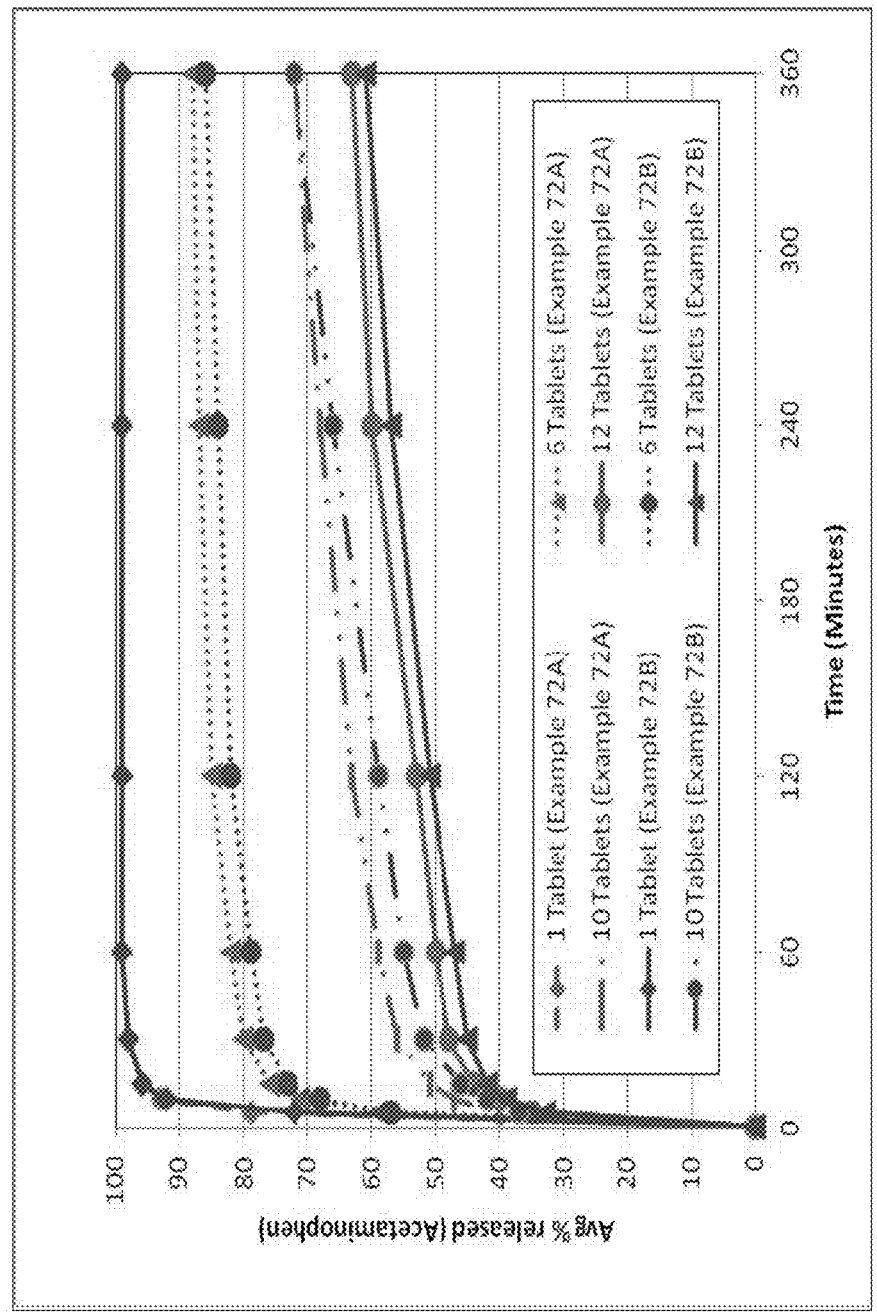
FIG. 11 shows a plot of multiple tablet oral abuse resistance (supratherapeutic dosing)—dissolution of acetaminophen from oxycodone hydrochloride/acetaminophen tablets (5/325 mg/tablet and 7.5/325 mg/tablet of oxycodone hydrochloride/acetaminophen) in 0.1N HCl media as a function of time.

The dosage form prepared according to Example 72A and Example 72B was evaluated for in vitro multiple tablet oral abuse resistance by stirring the selected number of tablets in 300 mL of 0.1N HCl. Dissolution was performed using USP apparatus II at 50 RPM and 37° C. One to twelve tablets were added to the vessel simultaneously and aliquots were removed periodically and analyzed for oxycodone hydrochloride (FIG. 10) and Acetaminophen (APAP) [FIG. 11] by HPLC. The results were plotted against time and appear in FIG. 10 and FIG. 11.

Example 74: Polymer Granules

TABLE 111

Granules Formulation

| Component | % w/w |
|---|---|
| Hypromellose K100M | 60 |
| Glyceryl behenate | 26 |
| Ethyl cellulose (10 cP) | 14 |
| TOTAL | 100 |

Granules were manufactured in a high shear granulator, where hypromellose, a portion of ethyl cellulose and glyceryl behenate were dry mixed for 3 minutes. Then a 10% w/w hydroalcoholic (~28 parts of water and ~72 parts of ethanol) solution of ethyl cellulose 10 cP was slowly added while maintaining the granulator impeller and chopper speed at pre-selected values that provide enough shear for granule formation and growth. Solution addition was continued until the entire amount of ethyl cellulose was added. The granules were then wet milled using a size reduction mill (Granumill) and were subsequently loaded into fluid bed for drying.

Example 75: Hydrocodone Bitartrate Coated Granules, 5%

The granules prepared according to Example 74 were then layered in a bottom spray fluid bed coater with a 12% w/w aqueous solution of hydrocodone bitartate and HPMC 2910 E3. The hydrocodone bitartrate layered granules were then coated in a bottom spray fluid bed coater with 25% alcoholic suspension of Eudragit E-100 copolymer and magnesium stearate.

TABLE 112

Layered Granules Formulation

| Component | % w/w |
|---|---|
| Hydrocodone bitartrate | 10 |
| Polymer granules (EC, HPMC and Compritol) | 85 |
| Hypromellose 2910 | 5 |
| TOTAL | 100 |

TABLE 113

Coated Granules Formulation

| Component | % w/w |
|---|---|
| Hydrocodone bitartrate layered granules, 10% | 50 |
| Eudragit E-100 | 33 |
| Magnesium stearate | 17 |
| TOTAL | 100 |

Example 76: Hydrocodone Bitartrate Tablets

The hydrocodone bitartrate coated granules were prepared according to the Example 75 above and mixed with polymer granules prepared according to Example 74. Another active agent i.e. Paracetamol (manufactured using acetaminophen and gelatin) and other excipients such as carbomer, crospovidone, sodium bicarbonate, mannitol, microcrystalline cellulose were added and blended for approximately 270 revolutions. Magnesium stearate was then added to lubricate the blend and blended for additional 45 revolutions prior to compressing into hydrocodone/acetaminophen tablets.

TABLE 114

Tablet Formulation

| Component | % w/w | mg/tablet |
|---|---|---|
| Hydrocodone bitartrate coated granules, 5% | 9.62 | 96.2 |
| Polymer granules | 5.38 | 53.8 |
| Paracetamol | 33.71 | 337.1* |
| Mannitol | 9.29 | 92.9 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 77A and Example 77B: Hydrocodone Bitartrate Tablets

The hydrocodone bitartrate coated granules, 5% were prepared according to the Example 75 above and mixed with coated polymer granules prepared according to Example 71. Another active agent i.e. Paracetamol (manufactured using acetaminophen and gelatin) and other excipients such as carbomer, crospovidone, sodium bicarbonate, mannitol, microcrystalline cellulose were added to the blender and blended for approximately 270 revolutions. Magnesium stearate was then added to lubricate the blend and blended for additional 45 revolutions prior to compressing into hydrocodone/acetaminophen tablets.

TABLE 115

Tablet Formulation

| | Example 77A | | Example 77B | |
|---|---|---|---|---|
| Component | % w/w | mg/tab | % w/w | mg/tab |
| Hydrocodone bitartrate coated granules, 5% | 9.62 | 96.2 | 14.42 | 144.2 |
| Coated Polymer granules | 10.38 | 103.8 | 5.58 | 55.8 |
| Paracetamol | 33.71 | 337.1* | 33.71 | 337.1* |
| Mannitol | 4.29 | 42.9 | 4.29 | 42.9 |
| Carbopol | 5.0 | 50 | 5.0 | 50 |
| Microcrystalline cellulose | 13.0 | 130 | 13.0 | 130 |
| Crospovidone | 20.0 | 200 | 20.0 | 200 |
| Sodium bicarbonate | 3.0 | 30 | 3.0 | 30 |
| Magnesium stearate | 1.0 | 10 | 1.0 | 10 |
| Total | 100 | 1000 | 100 | 1000 |

*contains 325 mg of acetaminophen

Example 78: In Vitro Analysis of Multiple Tablet Oral Abuse Resistance

Figure 12:
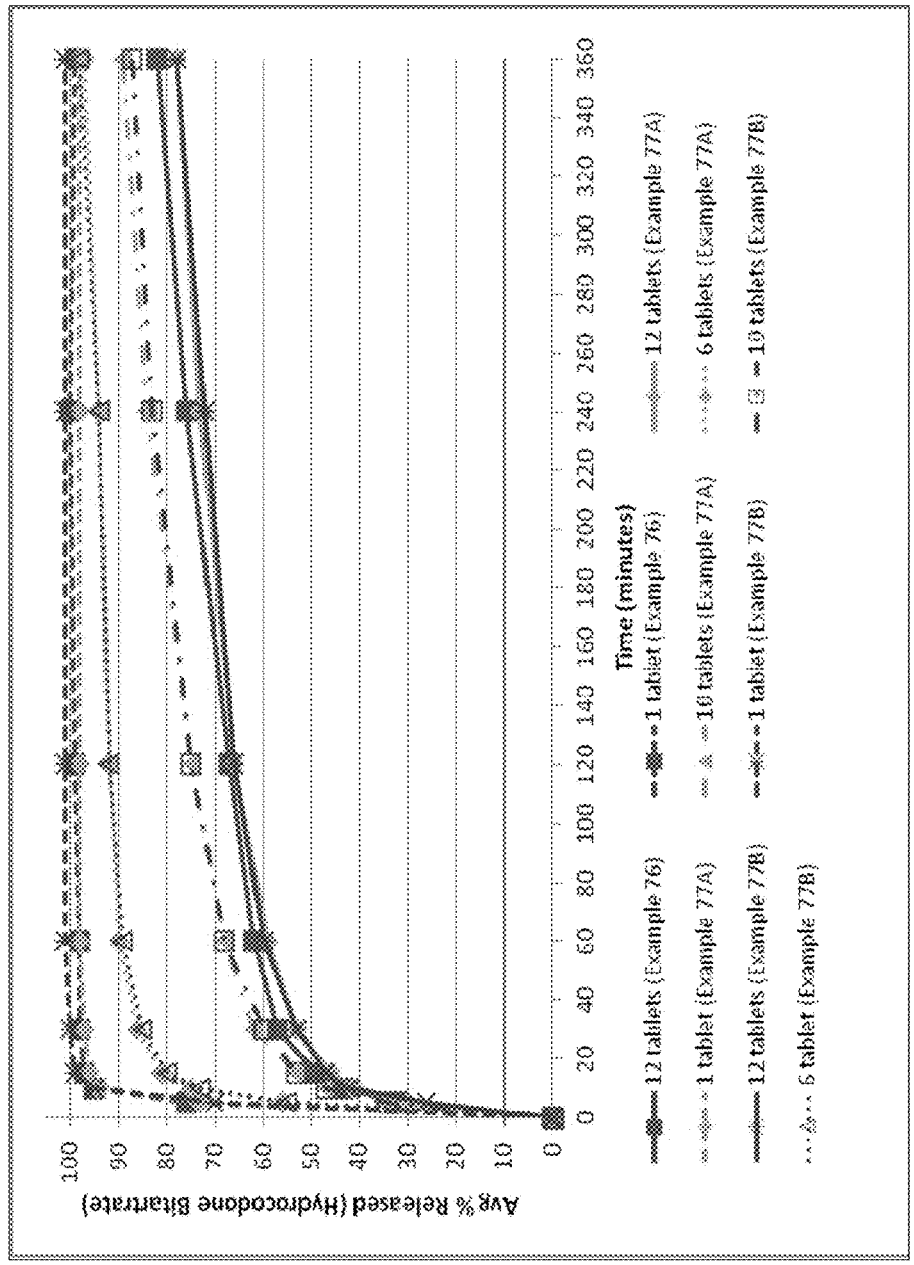
FIG. 12 shows a plot of multiple tablet oral abuse resistance (supratherapeutic dosing)—dissolution of hydrocodone bitartrate from hydrocodone bitartrate/acetaminophen tablets (5/325 mg/tablet and 7.5/325 mg/tablet of hydrocodone bitartrate/acetaminophen) in 0.1N HCl media as a function of time.
Figure 13:
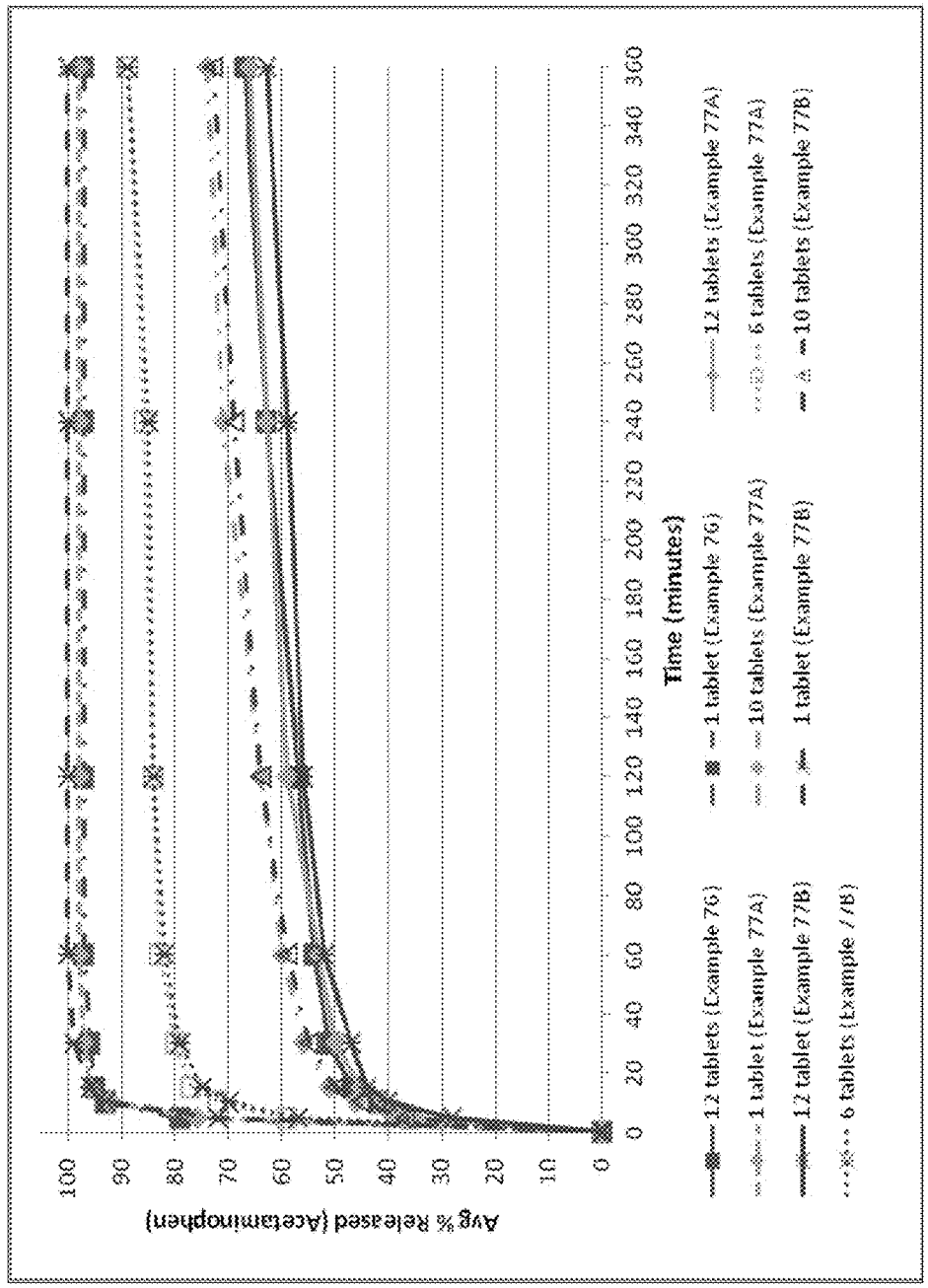
FIG. 13 shows a plot of multiple tablet oral abuse resistance (supratherapeutic dosing)—dissolution of acetaminophen from hydrocodone bitartrate/acetaminophen tablets (5/325 mg/tablet and 7.5/325 mg/tablet of hydrocodone bitartrate/acetaminophen) in 0.1N HCl media as a function of time.

The dosage form prepared according to Example 76 and Example 77A and Example 77B was evaluated for in vitro multiple tablet oral abuse resistance by stirring the selected number of tablets in 300 mL of 0.1N HCl. Dissolution was performed using USP apparatus II at 50 RPM and 37° C. One to twelve tablets were added to the vessel simultaneously and aliquots were removed periodically and analyzed for hydrocodone bitartrate (FIG. 12) and APAP (FIG. 13) by HPLC. The results were plotted against time and appear in FIG. 12 and FIG. 13.

Example 79: Coated Oxycodone Granules, 5%

Granules are prepared and subsequently coated. These coated particles are then blended with other components and compressed into tablets.

TABLE 116

Granules Formulation

| Component | % w/w |
|---|---|
| Hypromellose K100M | 54 |
| Glyceryl behenate | 23 |
| Ethyl cellulose (10 cP) | 13 |
| Oxycodone Hydrochloride | 10 |
| TOTAL | 100 |

TABLE 117

Coated Granules Formulation

| Component | % w/w |
|---|---|
| Oxycodone hydrochloride granules, 10% | 50 |
| Eudragit E-100 | 33 |
| Magnesium stearate | 17 |
| TOTAL | 100 |

Granules are manufactured in a high shear granulator, where oxycodone hydrochloride, hypromellose, a portion of ethyl cellulose and glyceryl behenate is dry mixed for 3 minutes. Then a hydroalcoholic solution of ethyl cellulose 10 cP is slowly added while maintaining the granulator impeller and chopper speed at pre-selected values that provide enough shear for granule formation and growth. Solution addition is continued until the entire amount of ethyl cellulose is added. The granules are then wet milled using a size reduction mill (Granumill) and subsequently loaded into fluid bed for drying. The oxycodone hydrochloride granules are then coated in a bottom spray fluid bed coater with 25% alcoholic suspension of Eudragit E-100 copolymer and magnesium stearate.

Example 80: Oxycodone/Acetaminophen Tablets

The oxycodone hydrochloride coated granules, 5% are prepared according to the Example 79 above and mixed with another active agent i.e. Paracetamol (manufactured using acetaminophen and gelatin) and other excipients such as carbomer, crospovidone, sodium bicarbonate, mannitol, microcrystalline cellulose and blended for approximately 270 revolutions. Magnesium stearate is then added to lubricate the blend and blended for additional 45 revolutions prior to compressing into oxycodone/acetaminophen tablets.

TABLE 118

Tablet Formulation

| Component | % w/w | mg/tablet |
|---|---|---|
| Oxycodone hydrochloride coated granules, 5% | 20 | 200 |
| Paracetamol | 34.2 | 342* |
| Mannitol | 3.8 | 38 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 81: Coated Oxycodone Granules

Oxycodone hydrochloride granules are prepared and subsequently coated. These coated particles are then blended with other components and compressed into tablets.

TABLE 119

Granules Formulation

| Component | % w/w |
|---|---|
| Hypromellose K100M | 56 |
| Glyceryl behenate | 25 |
| Ethyl cellulose (10 cP) | 14 |
| Oxycodone Hydrochloride | 5 |
| TOTAL | 100 |

TABLE 120

Coated Granules Formulation

| Component | % w/w |
|---|---|
| Oxycodone hydrochloride granules, 5% | 50 |
| Eudragit E-100 | 33 |
| Magnesium stearate | 17 |
| TOTAL | 100 |

Granules are manufactured in a high shear granulator, where oxycodone hydrochloride, hypromellose, a portion of ethyl cellulose and glyceryl behenate is dry mixed for 3 minutes. Then a hydroalcoholic solution of ethyl cellulose 10 cP is slowly added while maintaining the granulator impeller and chopper speed at pre-selected values that provide enough shear for granule formation and growth. Solution addition is continued until the entire amount of ethyl cellulose is added. The granules are then wet milled using a size reduction mill (Granumill) and subsequently loaded into fluid bed for drying. The oxycodone hydrochloride granules are then coated in a bottom spray fluid bed coater with 25% alcoholic suspension of Eudragit E-100 copolymer and magnesium stearate.

Example 82: Oxycodone/Acetaminophen Tablets

The oxycodone hydrochloride coated granules, 2.5% are prepared according to the Example 81 above and mixed with another active agent i.e. Paracetamol (manufactured using acetaminophen and gelatin) and other excipients such as carbomer, crospovidone, sodium bicarbonate, mannitol, microcrystalline cellulose and blended for approximately 270 revolutions. Magnesium stearate is then added to lubricate the blend and blended for additional 45 revolutions prior to compressing into oxycodone/acetaminophen tablets.

TABLE 121

Tablet Formulation

| Component | % w/w | mg/tablet |
|---|---|---|
| Oxycodone hydrochloride coated granules, 2.5% | 20 | 200 |
| Paracetamol | 34.2 | 342 |
| Mannitol | 3.8 | 38 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 83: Coated Oxycodone Granules

Oxycodone hydrochloride granules are prepared and subsequently coated. These coated particles are then blended with other components and compressed into tablets.

TABLE 122

Granules Formulation

| Component | % w/w |
|---|---|
| Hypromellose K100M | 54.5 |
| Glyceryl behenate | 24 |
| Ethyl cellulose (10 cP) | 14 |
| Oxycodone Hydrochloride | 7.5 |
| TOTAL | 100 |

TABLE 123

Coated Granules Formulation

| Component | % w/w |
|---|---|
| Oxycodone hydrochloride granules, 7.5% | 50 |
| Eudragit E-100 | 33 |
| Magnesium stearate | 17 |
| TOTAL | 100 |

Granules are manufactured in a high shear granulator, where oxycodone hydrochloride, hypromellose, a portion of ethyl cellulose and glyceryl behenate is dry mixed for 3 minutes. Then a hydroalcoholic solution of ethyl cellulose 10 cP is slowly added while maintaining the granulator impeller and chopper speed at pre-selected values that provide enough shear for granule formation and growth. Solution addition is continued until the entire amount of ethyl cellulose is added. The granules are then wet milled using a size reduction mill (Granumill) and subsequently loaded into fluid bed for drying. The oxycodone hydrochloride granules are then coated in a bottom spray fluid bed coater with 25% alcoholic suspension of Eudragit E-100 copolymer and magnesium stearate.

Example 84: Oxycodone/Acetaminophen Tablets

The oxycodone HCl coated granules, 3.75% are prepared according to Example 83 above and mixed with another active agent i.e. Paracetamol (manufactured using acetaminophen and gelatin) and other excipients such as carbomer, crospovidone, sodium bicarbonate, mannitol, microcrystalline cellulose and blended for approximately 270 revolutions. Magnesium stearate is then added to lubricate the blend and blended for additional 45 revolutions prior to compressing into oxycodone/acetaminophen tablets.

TABLE 124

Tablet Formulation

| Component | % w/w | mg/tablet |
|---|---|---|
| Oxycodone hydrochloride coated granules, 3.75% | 20 | 200 |
| Paracetamol | 34.2 | 342* |
| Mannitol | 3.8 | 38 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 85: Coated Oxycodone Hydrochloride Granules

Oxycodone hydrochloride granules are prepared and subsequently coated. These coated particles are then blended with other components and compressed into tablets.

TABLE 125

Granules Formulation

| Component | % w/w |
|---|---|
| Hypromellose K100M | 54 |
| Glyceryl behenate | 23 |
| Ethyl cellulose (10 cP) | 13 |
| Oxycodone Hydrochloride | 10 |
| TOTAL | 100 |

TABLE 126

Coated Granules Formulation

| Component | % w/w |
|---|---|
| Oxycodone hydrochloride granules, 10% | 40 |
| Eudragit E-100 | 40 |
| Magnesium stearate | 20 |
| TOTAL | 100 |

Granules are manufactured in a high shear granulator, where oxycodone hydrochloride, hypromellose, a portion of ethylcellulose and glyceryl behenate is dry mixed for 3 minutes. Then a hydroalcoholic solution of ethyl cellulose 10 cP is slowly added while maintaining the granulator impeller and chopper speed at pre-selected values that provide enough shear for granule formation and growth. Solution addition is continued until the entire amount of ethyl cellulose is added. The granules are then wet milled using a size reduction mill (Granumill) and subsequently loaded into fluid bed for drying. The oxycodone hydrochloride granules are then coated in a bottom spray fluid bed coater with 25% alcoholic suspension of Eudragit E-100 copolymer and magnesium stearate.

Example 86: Oxycodone/Acetaminophen Tablets

The oxycodone hydrochloride coated granules, 4% are prepared according to Example 85 above and mixed with another active agent i.e. Paracetamol (manufactured using acetaminophen and gelatin) and other excipients such as carbomer, crospovidone, sodium bicarbonate, mannitol, microcrystalline cellulose and blended for approximately 270 revolutions. Magnesium stearate is then added to lubricate the blend and blended for additional 45 revolutions prior to compressing into oxycodone/acetaminophen tablets.

TABLE 127

Tablet Formulation

| Component | % w/w | mg/tablets |
|---|---|---|
| Oxycodone hydrochloride coated granules, 4% | 18.8 | 188 |
| Paracetamol | 34.2 | 342* |
| Mannitol | 5 | 50 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 87: Coated Oxycodone Granules

Oxycodone granules are prepared, and subsequently coated. These coated particles are then blended with other components and compressed into tablets.

TABLE 128

Granules Formulation

| Component | % w/w |
|---|---|
| Hypromellose K100M | 54 |
| Glyceryl behenate | 23 |
| Ethyl cellulose (10 cP) | 13 |
| Oxycodone Hydrochloride | 10 |
| TOTAL | 100 |

TABLE 129

Coated Granules Formulation

| Component | % w/w |
|---|---|
| Oxycodone hydrochloride granules, 10% | 30 |
| Eudragit E-100 | 47 |
| Magnesium stearate | 23 |
| TOTAL | 100 |

Granules are manufactured in a high shear granulator, where oxycodone hydrochloride, hypromellose, a portion of ethyl cellulose and glyceryl behenate is dry mixed for 3 minutes. Then a hydroalcoholic solution of ethyl cellulose 10 cP is slowly added while maintaining the granulator impeller and chopper speed at pre-selected values that provide enough shear for granule formation and growth. Solution addition is continued until the entire amount of ethyl cellulose is added. The granules are then wet milled using a size reduction mill (Granumill) and subsequently loaded into fluid bed for drying. The oxycodone hydrochloride granules are then coated in a bottom spray fluid bed coater with 25% alcoholic suspension of Eudragit E-100 copolymer and magnesium stearate.

Example 88: Oxycodone/Acetaminophen Tablets

The oxycodone hydrochloride coated granules (3%) are prepared according to Example 87 above and mixed with another active agent i.e. Paracetamol (manufactured using acetaminophen and gelatin) and other excipients such as carbomer, crospovidone, sodium bicarbonate, mannitol, microcrystalline cellulose and blended for approximately 270 revolutions. Magnesium stearate is then added to lubricate the blend and blended for additional 45 revolutions prior to compressing into oxycodone/acetaminophen tablets.

TABLE 130

Tablet Formulation

| Component | % w/w | mg/tablet |
|---|---|---|
| Oxycodone hydrochloride coated granules, 3% | 16.7 | 167 |
| Paracetamol | 34.2 | 342* |
| Mannitol | 7.1 | 71 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 89: Coated Oxycodone Granules

Oxycodone granules are prepared and subsequently coated. These coated particles are then blended with other components and compressed into tablets.

TABLE 131

Granules Formulation

| Component | % w/w |
|---|---|
| Hypromellose K100M | 56 |
| Glyceryl behenate | 25 |
| Ethyl cellulose (10 cP) | 14 |
| Oxycodone Hydrochloride | 5 |
| TOTAL | 100 |

TABLE 132

Coated Granules Formulation

| Component | % w/w |
|---|---|
| Oxycodone hydrochloride granules, 5% | 70 |
| Eudragit E-100 | 20 |
| Magnesium stearate | 10 |
| TOTAL | 100 |

Granules are manufactured in a high shear granulator, where oxycodone hydrochloride, hypromellose, a portion of ethyl cellulose and glyceryl behenate is dry mixed for 3 minutes. Then a hydroalcoholic solution of ethyl cellulose 10 cP is slowly added while maintaining the granulator impeller and chopper speed at pre-selected values that provide enough shear for granule formation and growth. Solution addition is continued until the entire amount of ethyl cellulose is added. The granules are then wet milled using a size reduction mill (Granumill) and subsequently loaded into fluid bed for drying. The oxycodone hydrochloride granules are then coated in a bottom spray fluid bed coater with 25% alcoholic suspension of Eudragit E-100 copolymer and magnesium stearate.

Example 90: Oxycodone/Acetaminophen Tablets

The oxycodone hydrochloride coated granules, 3.5% are prepared according to the Example 89 above and mixed with another active agent i.e. Paracetamol (manufactured using acetaminophen and gelatin) and other excipients such as carbomer, crospovidone, sodium bicarbonate, mannitol, microcrystalline cellulose and blended for approximately 270 revolutions. Magnesium stearate is then added to lubricate the blend and blended for additional 45 revolutions prior to compressing into oxycodone/acetaminophen tablets.

TABLE 133

Tablet Formulation

| Component | % w/w | mg/tab |
|---|---|---|
| Oxycodone hydrochloride coated granules, 3.5% | 21.4 | 214 |
| Paracetamol | 34.2 | 342* |
| Mannitol | 2.4 | 24 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 91: Coated Oxycodone Granules

Oxycodone hydrochloride granules are prepared and subsequently coated. These coated particles are then blended with other components and compressed into tablets.

TABLE 134

Granules Formulation

| Component | % w/w |
|---|---|
| Hypromellose K100M | 54.5 |
| Glyceryl behenate | 24 |
| Ethyl cellulose (10 cP) | 14 |
| Oxycodone Hydrochloride | 7.5 |
| TOTAL | 100 |

TABLE 135

Coated Granules Formulation

| Component | % w/w |
|---|---|
| Oxycodone hydrochloride granules, 7.5% | 70 |
| Eudragit E-100 | 20 |
| Magnesium stearate | 10 |
| TOTAL | 100 |

Granules are manufactured in a high shear granulator, where oxycodone hydrochloride, hypromellose, a portion of ethyl cellulose and glyceryl behenate is dry mixed for 3 minutes. Then a hydroalcoholic solution of ethyl cellulose 10 cP is slowly added while maintaining the granulator impeller and chopper speed at pre-selected values that provide enough shear for granule formation and growth. Solution addition is continued until the entire amount of ethyl cellulose is added. The granules are then wet milled using a size reduction mill (Granumill) and subsequently loaded into fluid bed for drying. The oxycodone hydrochloride granules are then coated in a bottom spray fluid bed coater with 25% alcoholic suspension of Eudragit E-100 copolymer and magnesium stearate.

Example 92: Oxycodone/Acetaminophen Tablets

The oxycodone hydrochloride coated granules, 5.25% are prepared according to the Example 91 above and mixed with another active agent i.e. Paracetamol (manufactured using acetaminophen and gelatin) and other excipients such as carbomer, crospovidone, sodium bicarbonate, mannitol, microcrystalline cellulose and blended for approximately 270 revolutions. Magnesium stearate is then added to lubricate the blend and blended for additional 45 revolutions prior to compressing into oxycodone/acetaminophen tablets.

TABLE 136

Tablet Formulation

| Component | % w/w | mg/tablet |
|---|---|---|
| Oxycodone hydrochloride coated granules, 5.25% | 19.05 | 190.5 |
| Paracetamol | 34.2 | 342* |
| Mannitol | 4.75 | 47.5 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Total | 100 | 1000 |

*contains 325 mg of acetaminophen

Example 93: Hydrocodone/Acetaminophen Tablets

The hydrocodone bitartrate coated granules were prepared according to the Example 75 and mixed with another active agent i.e. Paracetamol (manufactured using acetaminophen and gelatin) along with other excipients such as carbomer, crospovidone, sodium bicarbonate, mannitol, microcrystalline cellulose (blended for approximately 270 revolutions). Magnesium stearate was then added to lubricate the blend and blended for additional 45 revolutions prior to compressing into hydrocodone/acetaminophen tablets.

TABLE 137

Tablet Formulation

| Component | % w/w | mg/tablet |
|---|---|---|
| Hydrocodone bitartrate coated granules, 5% | 20.0 | 200 |
| Paracetamol | 34.21 | 342.1* |
| Mannitol | 3.73 | 37.3 |
| Carbopol | 5.0 | 50 |
| Microcrystalline cellulose | 13.0 | 130 |
| Crospovidone | 20.0 | 200 |
| Sodium bicarbonate | 3.0 | 30 |
| Magnesium stearate | 1.0 | 10 |
| Iron Oxide Red | 0.06 | 0.6 |
| Total | 100 | 1000 |

*contains 325 mg of acetaminophen

Example 94: In Vitro Analysis of Multiple Tablet Oral Abuse Resistance—Crushed and Intact Tablets The dosage form (crushed or intact) prepared according to Example 93 was evaluated for in vitro multiple tablet oral abuse resistance by conducting dissolution experiments in 300 mL or 900 mL of 0.1N HCl. Dissolution was performed using USP apparatus II at 50 RPM and 37° C. Twelve tablets (crushed or intact) were added to the vessel simultaneously or sequentially and aliquots were removed periodically and were analyzed for hydrocodone bitartrate and APAP by HPLC. Crushing of the tablets was carried out using a morter and pestle (twelve strokes). The results were plotted against time and appear in FIG. 14 and FIG. 15.

Example 95: Esketamine HCl Tablets

Coated granules prepared per Example 31 are subsequently mixed with coated polymer granules prepared according to Example 71, and other components (carbomer, crospovidone, sodium bicarbonate, mannitol, microcrystalline cellulose) and blended for 270 revolutions. Magnesium stearate is added to lubricate the blend and the resulting mixture was blended for additional 45 revolutions prior to compressing into tablets.

TABLE 138

Tablet Formulation

| Components | mg/tablet | mg/tablet | mg/tablet | mg/tablet |
|---|---|---|---|---|
| Esketamine hydrochloride coated granules, 28.7% | 87.1 | 87.1 | 348.4 | 348.4 |
| Coated polymer granules | 50 | 31 | 50 | 31 |
| Mannitol | 37 | 37 | 37 | 37 |
| Carbopol | 50 | 50 | 50 | 50 |
| Microcrystalline cellulose | 130 | 130 | 130 | 130 |
| Crospovidone | 200 | 200 | 200 | 200 |
| Sodium bicarbonate | 30 | 30 | 30 | 30 |
| Magnesium stearate | 6 | 6 | 9 | 8.5 |
| Total | 590.1 | 571.1 | 854.4 | 834.9 |

Example 96: Esketamine HCl Tablets

Coated granules prepared per Example 31 are subsequently mixed with polymer granules prepared according to Example 74, and other components (carbomer, crospovidone, sodium bicarbonate, mannitol, microcrystalline cellulose) and blended for 270 revolutions. Magnesium stearate is added to lubricate the blend and the resulting mixture was blended for additional 45 revolutions prior to compressing into tablets.

TABLE 139

Tablet Formulation

| Components | mg/tablet | mg/tablet | mg/tablet | mg/tablet |
|---|---|---|---|---|
| Esketamine hydrochloride coated granules, 28.7% | 87.1 | 87.1 | 348.4 | 348.4 |
| Polymer granules | 50 | 27 | 50 | 27 |
| Mannitol | 37 | 37 | 37 | 37 |
| Carbopol | 50 | 50 | 50 | 50 |
| Microcrystalline cellulose | 130 | 130 | 130 | 130 |
| Crospovidone | 200 | 200 | 200 | 200 |
| Sodium bicarbonate | 30 | 30 | 30 | 30 |
| Magnesium stearate | 6 | 6 | 9 | 8.5 |
| Total | 590.1 | 567.1 | 854.4 | 830.9 |

Example 97: Esketamine HCl Tablets

The coated granules prepared per Example 27 are subsequently mixed with coated polymer granules prepared according to Example 71 and other components (carbomer, crospovidone, sodium bicarbonate, mannitol, microcrystalline cellulose) and blended for 270 revolutions. Magnesium stearate is added to lubricate the blend and the resulting mixture was blended for additional 45 revolutions prior to compressing into tablets.

TABLE 140

Esketamine hydrochloride tablet compositions

| Components mg/tab | 1 mg | 2 mg |
|---|---|---|
| Esketamine hydrochloride coated granules, 2.5% | 40 | 80 |
| Coated polymer granules | 160 | 120 |
| mannitol | 70 | 70 |
| carbopol | 50 | 50 |
| microcrystalline cellulose | 94 | 95 |
| Crospovidone | 200 | 200 |
| sodium bicarbonate | 30 | 30 |
| magnesium stearate | 11 | 18 |
| Total Tablet Weight | 655 | 663 |

Example 98: Esketamine HCl Tablets

The coated granules prepared per Example 27 above are subsequently mixed with polymer granules prepared according to Example 74 and other components (carbomer, crospovidone, sodium bicarbonate, mannitol, microcrystalline cellulose) and blended for 270 revolutions. Magnesium stearate is added to lubricate the blend and the resulting mixture was blended for additional 45 revolutions prior to compressing into tablets.

TABLE 141

Esketamine hydrochloride tablet compositions

| Components mg/tab | 1 mg | 2 mg |
|---|---|---|
| Esketamine hydrochloride coated granules, 2.5% | 40 | 80 |
| polymer granules | 80 | 60 |
| mannitol | 70 | 70 |
| carbopol | 50 | 50 |
| microcrystalline cellulose | 94 | 95 |
| Crospovidone | 150 | 150 |
| sodium bicarbonate | 30 | 30 |
| magnesium stearate | 11 | 18 |
| Total Tablet Weight | 525 | 553 |

Example 99: Preparation of Oxycodone HCl Coated Granules for Oxycodone/Acetaminophen Tablets A. Preparation of Polymer Granules The polymer granules used in the manufacturing of coated oxycodone HCl intermediate, 5.0% were manufactured using a high shear wet granulation process. The polymer granules batch formula is provided in Table 142, below. The polymer granules manufactured were used in subsequent layering and coated intermediate batch manufacturing.

TABLE 142

Components for Polymer Granule Formulation

| Component | % w/w |
|---|---|
| Hypromellose | 60.09 |
| Glyceryl behenate | 25.75 |
| Ethyl cellulose | 14.16 |
| Alcohol* | N.A. |
| Purified Water* | N.A. |
| TOTAL | 100.00 |

*Alcohol and water were removed from the polymer granules during processing.

Granules were manufactured in a high shear granulator, where hypromellose, glyceryl behenate, and a portion of ethylcellulose were dry mixed. Then, a hydroalcoholic solution of ethylcellulose (10% wt/wt) was slowly added while maintaining the granulator impeller and chopper speed at pre-selected values that provide enough shear for granule formation and growth. Solution addition was continued until the entire amount of ethylcellulose was added and granules formed. The granules were then wet milled using a size reduction mill (Granumill) and were subsequently loaded into fluid bed for drying.

B. Manufacturing of Oxycodone Hydrochloride Layered Granules, 10%.

The polymer granules prepared in Part A above were layered with an aqueous solution of HPMC 2910 and oxycodone hydrochloride. The polymer granules were layered in a bottom spray fluid bed coater with a 12% aqueous solution of oxycodone HCl and HPMC 2910.

Using polymer granules prepared in Part A above, the oxycodone HCl layered granules, 10% were manufactured per composition shown in Table 143, below.

TABLE 143

Components for Oxycodone Hydrochloride Layered Granule, 10% Formulation

| Component | % w/w |
|---|---|
| Oxycodone Hydrochloride | 10.00 |
| Polymer granules (Example 99, Part A, Table 142) | 85.00 |
| Hypromellose 2910 | 5.00 |
| Purified Water* | NA |
| TOTAL | 100.00 |

*Water was removed from the layered granules during processing.

C. Manufacturing of Coated Oxycodone Hydrochloride Intermediate, 5%.

The oxycodone HCl layered granules, 10%, prepared in Part B above, were coated in a bottom spray fluid bed coater with 25% alcoholic suspension of Eudragit E-100 copolymer and magnesium stearate. The resulting coated granules were blended for homogeneity and subsequently used for further blending and compression process.

The oxycodone HCl layered granules, 10% was used in the coating process which resulted in a coated oxycodone HCl granule intermediate, 5%, as shown in Table 144 below.

TABLE 144

Components for Coated Oxycodone HCl Intermediate, 5% Formulation

| Component | % w/w |
|---|---|
| Oxycodone Hydrochloride Layered Granules, 10% | 50.00 |
| Eudragit E-100 | 33.35 |
| Magnesium stearate | 16.65 |
| Alcohol* | NA |
| TOTAL | 100.00 |

*Alcohol was removed from the intermediate during processing

Example 100: Manufacturing of Oxycodone HCl and Acetaminophen Tablets

Oxycodone HCl and acetaminophen tablets were manufactured by blending the coated oxycodone HCl intermediate, 5% (Example 99, manufactured parts A, B and C above) with acetaminophen and other excipients prior to compressing into tablets. The composition for Oxycodone HCl and acetaminophen tablets is shown in Table 145.

TABLE 145

Oxycodone HCl and Acetaminophen Tablets

| | 10/325 mg Tablets | |
|---|---|---|
| Component | % w/w | mg/tablet |
| Coated Oxycodone HCl Intermediate, 5% | 20.00 | 200.0 |
| Paracetamol* | 34.21 | 342.1 |
| Crospovidone | 20.00 | 200.0 |
| Microcrystalline Cellulose | 9.00 | 90.0 |
| Carbopol 71G | 2.00 | 20.0 |
| Sodium Bicarbonate | 10.00 | 100.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 101: Manufacturing of Oxycodone HCl and Acetaminophen Tablets

Oxycodone HCl and acetaminophen tablets are manufactured by blending the coated oxycodone HCl intermediate, 5% (Example 99, manufactured parts A, B and C above) with acetaminophen, coated polymer granules intermediate (prepared according to Example 71) and other excipients prior to compressing into tablets. The composition for Oxycodone HCl and acetaminophen tablets is shown in Table 146.

TABLE 146

Oxycodone HCl and Acetaminophen Tablets

| Component | 5/325 mg Tablets | |
|---|---|---|
| | % w/w | mg/tablet |
| Coated Oxycodone HCl Intermediate, 5% | 10.00 | 100.0 |
| Coated Polymer Granules Intermediate | 10.00 | 100.0 |
| Paracetamol* | 34.21 | 342.1 |
| Crospovidone | 20.00 | 200.0 |
| Microcrystalline Cellulose | 9.00 | 90.0 |
| Carbopol 71G | 2.00 | 20.0 |
| Sodium Bicarbonate | 10.00 | 100.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder

Example 102: Manufacturing of Oxycodone HCl and Acetaminophen Tablets

Oxycodone HCl and acetaminophen tablets are manufactured by blending the coated oxycodone HCl intermediate, 5% (Example 99, manufactured parts A, B and C above) with acetaminophen, coated polymer granules intermediate (prepared according to Example 71) and other excipients prior to compressing into tablets. The composition for Oxycodone HCl and acetaminophen tablets is shown in Table 147.

TABLE 147

Oxycodone HCl and Acetaminophen Tablets

| Component | 7.5/325 mg Tablets | |
|---|---|---|
| | % w/w | mg/tablet |
| Coated Oxycodone HCl Intermediate, 5% | 15.00 | 150.0 |
| Coated Polymer Granules Intermediate | 5.00 | 50.0 |
| Paracetamol* | 34.21 | 342.1 |
| Crospovidone | 20.00 | 200.0 |
| Microcrystalline Cellulose | 9.00 | 90.0 |
| Carbopol 71G | 2.00 | 20.0 |
| Sodium Bicarbonate | 10.00 | 100.0 |
| Mannitol | 3.59 | 35.9 |
| Magnesium Stearate | 1.00 | 10.0 |
| Colloidal silicon dioxide | 0.20 | 2.0 |
| Total | 100 | 1000.0 |

*Equivalent to 32.5% w/w of acetaminophen per tablet based on composition of 95.0% acetaminophen and 5% binder.

Example 103: Manufacturing of Oxycodone HCl and Acetaminophen Tablets

Oxycodone HCl and acetaminophen tablets were manufactured by blending the coated oxycodone HCl intermediate, 5% (Example 99, manufactured parts A, B and C above) with acetaminophen and other excipients prior to compressing into tablets. The composition for Oxycodone HCl and acetaminophen tablets is shown in Table 148 below.

TABLE 148

Oxycodone HCl and Acetaminophen Tablets

| Component | 10/325 mg Tablets | |
|---|---|---|
| | % w/w | mg/tablet |
| Coated Oxycodone HCl Intermediate, 5% | 20.00 | 200.0 |
| Paracetamol* | 34.21 | 342.1 |
| Crospovidone | 18.50 | 185.0 |
| Microcrystalline Cellulose | 9.00 | 90.0 |
| Carbopol 71G | 0.50 | 5.0 |
| Sodium Bicarbonate | 13.00 | 130.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder

Example 104: Manufacturing of Oxycodone HCl and Acetaminophen Tablets

Oxycodone HCl and acetaminophen tablets are manufactured by blending the coated oxycodone HCl intermediate, 5% (Example 99, manufactured parts A, B and C above) with coated polymer granules intermediate (prepared according to Example 71), acetaminophen and other excipients prior to compressing into tablets. The composition for Oxycodone HCl and acetaminophen tablets is shown in Table 149 below.

TABLE 149

Oxycodone HCl and Acetaminophen Tablets

| Component | 5/325 mg Tablets | |
|---|---|---|
| | % w/w | mg/tablet |
| Coated Oxycodone HCl Intermediate, 5% | 10.00 | 100.0 |
| Coated Polymer Granules Intermediate | 10.00 | 100.0 |
| Paracetamol* | 34.21 | 342.1 |
| Crospovidone | 18.50 | 185.0 |
| Microcrystalline Cellulose | 9.00 | 90.0 |
| Carbopol 71G | 0.50 | 5.0 |
| Sodium Bicarbonate | 13.00 | 130.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 105: Manufacturing of Oxycodone HCl and Acetaminophen Tablets

Oxycodone HCl and acetaminophen tablets are manufactured by blending the coated oxycodone HCl intermediate, 5% (Example 99, manufactured parts A, B and C above) with coated polymer granules intermediate (prepared according to Example 71), acetaminophen and other excipients prior to compressing into tablets. The composition for Oxycodone HCl and acetaminophen tablets is shown in Table 150 below.

TABLE 150

Oxycodone HCl and Acetaminophen Tablets

|  | 7.5/325 mg Tablets | |
|---|---|---|
| Component | % w/w | mg/tablet |
| Coated Oxycodone HCl Intermediate, 5% | 15.00 | 150.0 |
| Coated Polymer Granules Intermediate | 5.00 | 50.0 |
| Paracetamol* | 34.21 | 342.1 |
| Crospovidone | 18.50 | 185.0 |
| Microcrystalline Cellulose | 9.00 | 90.0 |
| Carbopol 71G | 0.50 | 5.0 |
| Sodium Bicarbonate | 13.00 | 130.0 |
| Mannitol | 3.59 | 35.9 |
| Magnesium Stearate | 1.00 | 10.0 |
| Colloidal silicon dioxide | 0.20 | 2.0 |
| Total | 100 | 1000.0 |

*Equivalent to 32.5% w/w of acetaminophen per tablet based on composition of 95.0% acetaminophen and 5% binder.

Example 106: Preparation of Hydrocodone Bitartrate Coated Granules for Hydrocodone/Acetaminophen Tablets A. Preparation of Polymer Granules The polymer granules used in the manufacturing of coated hydrocodone bitartrate intermediate, 5.0% were manufactured using a high shear wet granulation process. The polymer granules batch formula is provided in Table 151, below. The polymer granules manufactured were used in subsequent layering and coated intermediate batch manufacturing.

TABLE 151

Components for Polymer Granule Formulation

| Component | % w/w |
|---|---|
| Hypromellose | 60.09 |
| Glyceryl behenate | 25.75 |
| Ethyl cellulose | 14.16 |
| Alcohol* | N.A. |
| Purified Water* | N.A. |
| TOTAL | 100.00 |

*Alcohol and water were removed from the polymer granules during processing.

Granules were manufactured in a high shear granulator, where hypromellose, glyceryl behenate, and a portion of ethylcellulose were dry mixed. Then, a hydroalcoholic solution of ethylcellulose (10% wt/wt) was slowly added while maintaining the granulator impeller and chopper speed at pre-selected values that provide enough shear for granule formation and growth. Solution addition was continued until the entire amount of ethylcellulose was added and granules formed. The granules were then wet milled using a size reduction mill (Granumill) and were subsequently loaded into fluid bed for drying.

B. Manufacturing of Hydrocodone Bitartrate Layered Granules, 10%.

The polymer granules prepared in Part A above were layered with an aqueous solution of HPMC 2910 and hydrocodone bitartrate. The polymer granules were layered in a bottom spray fluid bed coater with a 12% aqueous solution of hydrocodone bitartrate and HPMC 2910.

Using polymer granules prepared in Part A above, the hydrocodone bitartrate layered granules, 10% were manufactured per composition shown in Table 152 below.

TABLE 152

Components for Hydrocodone Bitartrate Layered Granule, 10% Formulation

| Component | % w/w |
|---|---|
| Hydrocodone Bitartrate | 10.00 |
| Polymer granules (Example 106, Part A, Table 151) | 85.00 |
| Hypromellose 2910 | 5.00 |
| Purified Water* | NA |
| TOTAL | 100.00 |

*Water was removed from the layered granules during processing.

C. Manufacturing of Coated Hydrocodone Bitartrate Intermediate, 5%.

The hydrocodone bitartrate layered granules, 10%, prepared in Part B above, were coated in a bottom spray fluid bed coater with 25% alcoholic suspension of Eudragit E-100 copolymer and magnesium stearate. The resulting coated granules were blended for homogeneity and subsequently used for further blending and compression process.

The hydrocodone bitartrate layered granules, 10% was used in the coating process which resulted in a coated hydrocodone bitartrate coated intermediate, 5%, as shown in Table 153, below.

TABLE 153

Components for Coated Hydrocodone Bitartrate Intermediate, 5% Formulation

| Component | % w/w |
|---|---|
| Hydrocodone Bitartrate Layered Granules, 10% | 50.00 |
| Eudragit E-100 | 33.35 |
| Magnesium stearate | 16.65 |
| Alcohol* | NA |
| TOTAL | 100.00 |

*Alcohol was removed from the intermediate during processing

Example 107: Manufacturing of Hydrocodone Bitartrate and Acetaminophen Tablets Hydrocodone bitartrate and acetaminophen tablets were manufactured by blending the coated hydrocodone bitartrate intermediate, 5% (Example 106, manufactured parts A, B and C above) with acetaminophen and other excipients prior to compressing into tablets. The composition for hydrocodone bitartrate and acetaminophen tablets is shown in Table 154.

TABLE 154

Hydrocodone Bitartrate and Acetaminophen Tablets

|  | 10/325 mg Tablets | |
|---|---|---|
| Component | % w/w | mg/tablet |
| Coated Hydrocodone Bitartrate Intermediate, 5% | 20.00 | 200.0 |
| Paracetamol* | 34.21 | 342.1 |
| Crospovidone | 20.00 | 200.0 |
| Microcrystalline Cellulose | 9.00 | 90.0 |
| Carbopol 71G | 2.00 | 20.0 |
| Sodium Bicarbonate | 10.00 | 100.0 |
| Mannitol | 3.59 | 35.9 |

TABLE 154-continued

Hydrocodone Bitartrate and Acetaminophen Tablets

| Component | 10/325 mg Tablets | |
|---|---|---|
| | % w/w | mg/tablet |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 108: Manufacturing of Hydrocodone Bitartrate and Acetaminophen Tablets Hydrocodone bitartrate and acetaminophen tablets are manufactured by blending the coated hydrocodone bitartrate intermediate, 5% (Example 106, manufactured parts A, B and C above) with acetaminophen, coated polymer granules intermediate (prepared according to Example 71) and other excipients prior to compressing into tablets. The composition for hydrocodone bitartrate and acetaminophen tablets is shown in Table 155.

TABLE 155

Hydrocodone Bitartrate and Acetaminophen Tablets

| Component | 5/325 mg Tablets | |
|---|---|---|
| | % w/w | mg/tablet |
| Coated Hydrocodone Bitartrate Intermediate, 5% | 10.00 | 100.0 |
| Coated Polymer Granules Intermediate | 10.00 | 100.0 |
| Paracetamol* | 34.21 | 342.1 |
| Crospovidone | 20.00 | 200.0 |
| Microcrystalline Cellulose | 9.00 | 90.0 |
| Carbopol 71G | 2.00 | 20.0 |
| Sodium Bicarbonate | 10.00 | 100.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 109: Manufacturing of Hydrocodone Bitartrate and Acetaminophen Tablets Hydrocodone bitartrate and acetaminophen tablets are manufactured by blending the coated hydrocodone bitartrate intermediate, 5% (Example 106, manufactured parts A, B and C above) with acetaminophen, coated polymer granules intermediate (prepared according to Example 71) and other excipients prior to compressing into tablets. The composition for hydrocodone bitartrate and acetaminophen tablets is shown in Table 156 below.

TABLE 156

Hydrocodone bitartrate and Acetaminophen Tablets

| Component | 7.5/325 mg Tablets | |
|---|---|---|
| | % w/w | mg/tablet |
| Coated Hydrocodone Bitartrate Intermediate, 5% | 15.00 | 150.0 |
| Coated Polymer Granules Intermediate | 5.00 | 50.0 |

TABLE 156-continued

Hydrocodone bitartrate and Acetaminophen Tablets

| Component | 7.5/325 mg Tablets | |
|---|---|---|
| | % w/w | mg/tablet |
| Paracetamol* | 34.21 | 342.1 |
| Crospovidone | 20.00 | 200.0 |
| Microcrystalline Cellulose | 9.00 | 90.0 |
| Carbopol 71G | 2.00 | 20.0 |
| Sodium Bicarbonate | 10.00 | 100.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 110: Manufacturing of Hydrocodone Bitartrate and Acetaminophen Tablets Hydrocodone bitartrate and acetaminophen tablets were manufactured by blending the coated hydrocodone bitartrate intermediate, 5% (Example 106, manufactured parts A, B and C above) with acetaminophen and other excipients prior to compressing into tablets. The composition for hydrocodone bitartrate and acetaminophen tablets is shown in Table 157, below.

TABLE 157

Hydrocodone Bitartrate and Acetaminophen Tablets

| Component | 10/325 mg Tablets | |
|---|---|---|
| | % w/w | mg/tablet |
| Coated Hydrocodone Bitartrate Intermediate, 5% | 20.00 | 200.0 |
| Paracetamol* | 34.21 | 342.1 |
| Crospovidone | 18.50 | 185.0 |
| Microcrystalline Cellulose | 9.00 | 90.0 |
| Carbopol 71G | 0.50 | 5.0 |
| Sodium Bicarbonate | 13.00 | 130.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 111: Manufacturing of Hydrocodone Bitartrate and Acetaminophen Tablets Hydrocodone bitartrate and acetaminophen tablets are manufactured by blending the coated hydrocodone bitartrate intermediate, 5% (Example 106, manufactured parts A, B and C above) with coated polymer granules intermediate (prepared according to Example 71), acetaminophen and other excipients prior to compressing into tablets. The composition for hydrocodone bitartrate and acetaminophen tablets is shown in Table 158 below.

TABLE 158

Hydrocodone Bitartrate and Acetaminophen Tablets

| | 5/325 mg Tablets | |
|---|---|---|
| Component | % w/w | mg/tablet |
| Coated Hydrocodone Bitartrate Intermediate, 5% | 10.00 | 100.0 |
| Coated Polymer Granules Intermediate | 10.00 | 100.0 |
| Paracetamol* | 34.21 | 342.1 |
| Crospovidone | 18.50 | 185.0 |
| Microcrystalline Cellulose | 9.00 | 90.0 |
| Carbopol 71G | 0.50 | 5.0 |
| Sodium Bicarbonate | 13.00 | 130.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 112: Manufacturing of Hydrocodone Bitartrate and Acetaminophen Tablets Hydrocodone bitartrate and acetaminophen tablets are manufactured by blending the coated hydrocodone bitartrate intermediate, 5% (Example 106, manufactured parts A, B and C above) with coated polymer granules intermediate (prepared according to Example 71), acetaminophen and other excipients prior to compressing into tablets. The composition for hydrocodone bitartrate and acetaminophen tablets is shown in Table 159 below.

TABLE 159

Hydrocodone Bitartrate and Acetaminophen Tablets

| | 7.5/325 mg Tablets | |
|---|---|---|
| Component | % w/w | mg/tablet |
| Coated Hydrocodone Bitartrate Intermediate, 5% | 15.00 | 150.0 |
| Coated Polymer Granules Intermediate | 5.00 | 50.0 |
| Paracetamol* | 34.21 | 342.1 |
| Crospovidone | 18.50 | 185.0 |
| Microcrystalline Cellulose | 9.00 | 90.0 |
| Carbopol 71G | 0.50 | 5.0 |
| Sodium Bicarbonate | 13.00 | 130.0 |
| Mannitol | 3.59 | 35.9 |
| Magnesium Stearate | 1.00 | 10.0 |
| Colloidal silicon dioxide | 0.20 | 2.0 |
| Total | 100.00 | 1000.0 |

*Equivalent to 32.5% w/w of acetaminophen per tablet based on composition of 95.0% acetaminophen and 5% binder.

Example 113: Preparation of Esketamine Coated Granules for Esketamine HCl Tablets A. Preparation of Polymer Granules The polymer granules used in the manufacturing of Coated Esketamine HCl, Intermediate, 37% were manufactured using a high shear wet granulation process. The polymer granules batch formula is provided in Table 160, below. The polymer granules manufactured were used in a subsequent layering and coated intermediate batch manufacturing.

TABLE 160

Components for Polymer Granule formulation

| Component | % w/w |
|---|---|
| Hypromellose | 60.09 |
| Glyceryl behenate | 25.75 |
| Ethyl cellulose | 14.16 |
| Alcohol* | N.A. |
| Purified Water* | N.A. |
| TOTAL | 100.00 |

*Alcohol and water were removed from the polymer granules during processing.

Granules were manufactured in a high shear granulator, where hypromellose, glyceryl behenate, and a portion of ethylcellulose were dry mixed. Then, a hydroalcoholic solution of ethylcellulose (10% wt/wt) was slowly added while maintaining the granulator impeller and chopper speed at pre-selected values that provide enough shear for granule formation and growth. Solution addition was continued until the entire amount of ethylcellulose was added and granules formed. The granules were then wet milled using a size reduction mill (Granumill) and were subsequently loaded into fluid bed for drying.

B. Manufacturing of Esketamine Hydrochloride Layered Granules, 45%.

The polymer granules prepared in Part A above were layered with an aqueous solution of HPMC 2910 and esketamine hydrochloride. The polymer granules were layered in a bottom spray fluid bed coater with a 18% aqueous solution of esketamine HCl and HPMC 2910.

Using polymer granules prepared in Part A above, the esketamine HCl layered granules, 45% were manufactured per composition shown in Table 161 below.

TABLE 161

Components for Esketamine HCl Layered Granule, 45% formulation

| Component | % w/w |
|---|---|
| Esketamine Hydrochloride | 45.07 |
| Polymer granules (Example 113, Part A, Table 160) | 37.60 |
| Hypromellose 2910 | 17.33 |
| Purified Water* | NA |
| TOTAL | 100.00 |

*Water was removed from the layered granules during processing.

C. Manufacturing of Coated Esketamine Hydrochloride Intermediate, 37%.

The Esketamine HCl layered granules, 45%, prepared in Part B above, were coated in a bottom spray fluid bed coater with 25% alcoholic suspension of Eudragit E-100 copolymer and magnesium stearate.

The esketamine HCl layered granules, 45% was used in the coating process which resulted in a coated esketamine HCl coated intermediate, 37%, as shown in Table 162 below.

TABLE 162

Components for Esketamine HCl Coated Intermediate, 37% formulation

| Component | % w/w |
|---|---|
| Esketamine Hydrochloride Layered Granules, 45% | 81.99 |
| Eudragit E-100 | 12.00 |

TABLE 162-continued

Components for Esketamine HCl Coated Intermediate, 37% formulation

| Component | % w/w |
|---|---|
| Magnesium stearate | 6.00 |
| Alcohol* | NA |
| TOTAL | 100.0 |

*Alcohol was removed from the intermediate during processing

Example 114A, 114B and 114C: Manufacturing of Esketamine HCl Tablets

Esketamine HCl tablets were manufactured by blending the coated esketamine HCl intermediate, 37% (Example 113, manufactured parts A, B and C above) with coated polymer granules (prepared according to Example 71) and other excipients prior to compressing into tablets. The composition for Esketamine HCl tablets is shown in Table 163.

TABLE 163

Esketamine HCl Tablets

| | 100 mg Tablets | | | | | |
|---|---|---|---|---|---|---|
| | Example 114A | | Example 114B | | Example 114C | |
| Component | % w/w | mg/tab | % w/w | mg/tab | % w/w | mg/tab |
| Coated Esketamine HCl Intermediate, 37% | 27.03 | 270.30 | 27.03 | 270.30 | 27.03 | 270.30 |
| Coated Polymer Granule | 20.00 | 200.00 | 20.00 | 200.00 | 20.00 | 200.00 |
| Mannitol | 10.97 | 109.70 | 6.97 | 69.70 | 6.97 | 69.70 |
| Crospovidone | 20.00 | 200.00 | 20.00 | 200.00 | 18.50 | 185.00 |
| Microcrystalline Cellulose | 13.00 | 130.00 | 13.00 | 130.00 | 13.00 | 130.00 |
| Sodium Bicarbonate | 3.00 | 30.00 | 10.00 | 100.00 | 13.00 | 130.00 |
| Carbopol 71G | 5.00 | 50.00 | 2.00 | 20.00 | 0.50 | 5.00 |
| Magnesium Stearate | 1.00 | 10.00 | 1.00 | 10.00 | 1.00 | 10.00 |
| Total | 100.00 | 1000.00 | 100.00 | 1000.00 | 100.00 | 1000.00 |

What is claimed is:

1. An immediate release abuse deterrent dosage form comprising:
   core-shell particles comprising
      a core comprising a gelling polymer, wherein the core does not include microcrystalline cellulose, a sugar sphere, or an active pharmaceutical agent;
      an active pharmaceutical layer surrounding the core, the active pharmaceutical layer comprising a narcotic analgesic; and
      at least one layer surrounding the active pharmaceutical layer, the at least one layer comprising a pH-sensitive film comprising a pH-sensitive polymer that is insoluble in water at a pH greater than 5 and is soluble in water at a pH below 5;
   wherein the dosage form demonstrates an immediate release profile of the narcotic analgesic when administered to a human in therapeutic doses and an extended release profile of the narcotic analgesic when administered to a human in supratherapeutic doses.

2. The dosage form according to claim 1, wherein the supratherapeutic dose is five or more tablets.

3. The dosage form according to claim 1, wherein the dosage form is in a compressed tablet form.

4. The dosage form according to claim 1, wherein at least 90 percent of the total amount of the narcotic analgesic in the core shell particles is contained in the active pharmaceutical layer.

5. The dosage form according to claim 1, further comprising a second type of core-shell particles that do not contain an active pharmaceutical layer, the second type of core-shell particles comprising:
   a core, the core comprising a gelling polymer, wherein the gelling polymer in the core is selected from a natural starch, a synthetic starch, a natural cellulose, a synthetic cellulose, an acrylate, a polyalkylene oxide, a carbomer and combinations thereof; and
   at least one layer surrounding the core, the at least one layer comprising a pH-sensitive film comprising pH-sensitive polymer that is insoluble at a pH greater than 5 and is soluble at a pH below 5.

6. The dosage form according to claim 1, wherein the narcotic analgesic is an opioid.

7. The dosage form according to claim 6, wherein the dosage form further comprises a nonsteroidal analgesic drug.

8. The dosage form according to claim 6, wherein the opioid is selected from buprenorphine, codeine, dihydrocodeine, dihydromorphine, hydrocodone, hydromorphone, morphine, oxycodone, oxymorphone, and pharmaceutically acceptable salts thereof.

9. The dosage form according to claim 7, wherein the nonsteroidal analgesic drug is selected from acetaminophen, aspirin, ibuprofen and naproxen.

10. The dosage form according to claim 1, wherein the gelling polymer in the core is selected from ethylcellulose, cellulose acetate, cellulose acetate propionate, cellulose acetate butyrate, cellulose acetate phthalate, cellulose triacetate, cellulose ether, cellulose ester, cellulose ester ether, cellulose, hydroxypropyl methyl cellulose, hydroxy methyl cellulose, methyl cellulose, hydroxyethylmethyl cellulose, sodium carboxymethyl cellulose, a carbomer polymer, polyethylene oxide, and combinations thereof.

11. The dosage form according to claim 1, further comprising a matrix.

12. The dosage form according to claim 11, wherein the matrix comprises a gelling polymer.

13. The dosage form according to claim 12, wherein the gelling polymer in the matrix is selected from a synthetic cellulose, a polyalkylene oxide, a carbomer, and combinations thereof.

14. The dosage form according to claim 12, wherein the gelling polymer in the matrix is a carbomer.

15. The dosage form according to claim 12, wherein, wherein the gelling polymer in the matrix is present in an amount from 0.5 to 15 weight percent based on the total weight of the dosage form.

16. The dosage form according to claim 1, wherein the pH-sensitive polymer is a copolymer of dimethyl aminoethyl methacrylate, butyl methacrylate, and methyl methacrylate monomers.

17. The dosage form according to claim 1, wherein the dosage form excludes an emetic, a nasal irritant, an opioid antagonist, and an effervescent.

18. The dosage form according to claim 1, wherein the dosage form reduces the risk of an overdose of the narcotic analgesic by simultaneous oral ingestion of multiple units of the oral dosage form.

19. A method of reducing the potential for abuse by a human of a narcotic analgesic drug by simultaneous oral ingestion of multiple dosage units of said narcotic analgesic drug, the method comprising providing an immediate release abuse deterrent dosage form according to claim 1.

20. The method according to claim 19, wherein at least 90 percent of the total amount of the narcotic analgesic in the core shell particles is contained in the active pharmaceutical layer.

21. The method according to claim 19, wherein the dosage form further comprises a second type of core-shell particles that do not contain an active pharmaceutical layer, the second type of core-shell particles comprising:
   a core, the core comprising a gelling polymer, wherein the gelling polymer in the core is selected from a natural starch, a synthetic starch, a natural cellulose, a synthetic cellulose, an acrylate, a polyalkylene oxide, a carbomer and combinations thereof; and
   at least one layer surrounding the core, the at least one layer comprising a pH-sensitive film comprising pH-sensitive polymer that is insoluble at a pH greater than 5 and is soluble at a pH below 5.

22. The method according to claim 19, wherein the narcotic analgesic is an opioid.

23. The method according to claim 22, wherein the dosage form further comprises a nonsteroidal analgesic drug.

24. The method according to claim 22, wherein the opioid is selected from buprenorphine, codeine, dihydrocodeine, dihydromorphine, hydrocodone, hydromorphone, morphine, oxycodone, oxymorphone, and pharmaceutically acceptable salts thereof.

25. The method according to claim 23, wherein the nonsteroidal analgesic drug is selected from acetaminophen, aspirin, ibuprofen and naproxen.

26. The method according to claim 19, wherein the gelling polymer in the core is selected from ethylcellulose, cellulose acetate, cellulose acetate propionate, cellulose acetate butyrate, cellulose acetate phthalate, cellulose triacetate, cellulose ether, cellulose ester, cellulose ester ether, cellulose, hydroxypropyl methyl cellulose, hydroxy methyl cellulose, methyl cellulose, hydroxyethylmethyl cellulose, sodium carboxymethyl cellulose, a carbomer polymer, polyethylene oxide, and combinations thereof.

27. The method according to claim 19, wherein the dosage form further comprises a matrix comprising a gelling polymer, and wherein the gelling polymer in the matrix is a carbomer polymer.

28. The method according to claim 27, wherein, wherein the gelling polymer in the matrix is present in an amount from 0.5 to 15 weight percent based on the total weight of the dosage form.

29. The method according to claim 19, wherein the pH-sensitive polymer is a copolymer of dimethyl aminoethyl methacrylate, butyl methacrylate, and methyl methacrylate monomers.

30. The method according to claim 19, wherein the dosage form excludes an emetic, a nasal irritant, an opioid antagonist, and an effervescent.

31. The method according to claim 19, wherein the dosage form reduces the risk of an overdose of the narcotic analgesic by simultaneous oral ingestion of multiple units of the oral dosage form.

32. The method according to claim 19, wherein the dosage form that demonstrates an immediate release profile when administered in therapeutic doses, but which demonstrates an extended release profile when administered in supratherapeutic doses.

33. The method according to claim 32, wherein the supratherapeutic dose is five or more tablets.

* * * * *